US010071186B2

(12) United States Patent
James et al.

(10) Patent No.: US 10,071,186 B2
(45) Date of Patent: Sep. 11, 2018

(54) GLYCOSAMINOGLYCAN AND SYNTHETIC POLYMER MATERIAL FOR BLOOD-CONTACTING APPLICATIONS

(71) Applicant: Colorado State University Research Foundation, Fort Collins, CO (US)

(72) Inventors: Susan P. James, Bellvue, CO (US); Harold Dean, IV, Ventura, CA (US); Lakshmi Prasad Dasi, Fort Collins, CO (US); Marcio H. Forleo, Fort Collins, CO (US); Ketul C. Popat, Fort Collins, CO (US); Nicole R. Lewis, Fort Collins, CO (US); David Alois Prawel, Loveland, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 561 days.

(21) Appl. No.: 14/381,332

(22) PCT Filed: Mar. 11, 2013

(86) PCT No.: PCT/US2013/030230
§ 371 (c)(1),
(2) Date: Aug. 27, 2014

(87) PCT Pub. No.: WO2013/138240
PCT Pub. Date: Sep. 19, 2013

(65) Prior Publication Data
US 2015/0196688 A1    Jul. 16, 2015

Related U.S. Application Data

(60) Provisional application No. 61/609,818, filed on Mar. 12, 2012.

(51) Int. Cl.
| | | |
|---|---|---|
| A61L 27/48 | (2006.01) | |
| A61F 2/24 | (2006.01) | |
| A61L 27/18 | (2006.01) | |
| A61L 27/20 | (2006.01) | |
| A61L 27/54 | (2006.01) | |
| A61L 27/16 | (2006.01) | |
| A61L 27/50 | (2006.01) | |
| A61L 29/12 | (2006.01) | |
| A61L 29/14 | (2006.01) | |
| A61L 31/12 | (2006.01) | |
| A61L 31/14 | (2006.01) | |
| A61L 17/10 | (2006.01) | |

(52) U.S. Cl.
CPC ............... *A61L 27/48* (2013.01); *A61F 2/24* (2013.01); *A61L 17/10* (2013.01); *A61L 27/16* (2013.01); *A61L 27/18* (2013.01); *A61L 27/20* (2013.01); *A61L 27/50* (2013.01); *A61L 27/54* (2013.01); *A61L 29/126* (2013.01); *A61L 29/14* (2013.01); *A61L 31/129* (2013.01); *A61L 31/14* (2013.01); *A61L 2300/236* (2013.01); *A61L 2300/42* (2013.01); *A61L 2300/62* (2013.01); *A61L 2430/20* (2013.01)

(58) Field of Classification Search
CPC .. C08L 5/08; A61L 17/10; A61L 27/48; A61L 29/126; A61L 31/129; A61L 2300/236; A61L 2300/42; A61L 2300/62; A61L 2430/20; A61L 27/16; A61L 27/18; A61L 27/20; A61L 27/50; A61L 27/54; A61L 29/01
See application file for complete search history.

(56) References Cited

U.S. PATENT DOCUMENTS

| | | | |
|---|---|---|---|
| 3,983,581 A | 10/1976 | Angell et al. | |
| 4,500,676 A | 2/1985 | Balazs et al. | |
| 5,458,826 A | 10/1995 | Bhuvaneshwar et al. | |
| 6,517,571 B1 | 2/2003 | Brauker et al. | |
| 7,081,133 B2 * | 7/2006 | Chinn | A61F 2/2409 623/2.41 |
| 7,662,954 B2 | 1/2010 | James et al. | |
| 8,293,890 B2 | 10/2012 | Hossainy et al. | |
| 8,303,972 B2 | 11/2012 | Michal | |
| 8,524,886 B2 | 8/2013 | James et al. | |

(Continued)

FOREIGN PATENT DOCUMENTS

| | | |
|---|---|---|
| GB | 2151244 A | 7/1985 |
| WO | WO 2000/69930 A1 | 11/2000 |

OTHER PUBLICATIONS

Zhang et al. (Journal of Biomedical materials Research Part A; 86-96; 2006).*
International Search Report and Written Opinion, PCT/US2013/030230, dated May 30, 2013.
Hoare, R. et al., "Hydrogels in drug delivery: Progress and challenges." *Polymer*, 49:1993-2007 (2008).
Ibrahim, S. et al., "A surface-tethered model to assess size-specific effects of hyaluronan (HA) on endothelial cells," *Biomaterials*, 28:825-835 (2007).
Ibrahim, S. et al., "Hyaluronic acid cues for functional endothelialization of vascular constructs." *J Tissue Eng Regen Med*, 2:22-32 (2008).
Marmur, "Hydro- hygro- oleo- omni-phobic? Terminology of wettability classification," *Soft Matter*, 8:6867 (2012).

(Continued)

*Primary Examiner* — Anna Falkowitz
(74) *Attorney, Agent, or Firm* — Polsinelli PC

(57) ABSTRACT

Provided herein is a composite, comprising: a polymer host selected from the group consisting of low-density polyethylene (LDPE), linear low-density polyethylene (LLDPE), polyethylene terephthalate (PET), polytetrafluoroethylene (PTFE), and polypropylene (PP), polyurethane, polycaprolactone (PCL), polydimethylsiloxane (PDMS), polymethylmethacrylate (PMMA), and polyoxymethylene (POM); and a guest molecule comprising hyaluronic acid; wherein the guest molecule is disposed within the polymer host, and wherein the guest molecule is covalently bonded to at least one other guest molecule. Also provided herein are methods for forming the composite, and blood-contacting devices made from the composite, such as heart valves and vascular grafts.

16 Claims, 27 Drawing Sheets

(56) References Cited

U.S. PATENT DOCUMENTS

| | | |
|---|---|---|
| 8,524,884 B2 | 9/2013 | James et al. |
| 2003/0181976 A1 | 9/2003 | Vyavahare et al. |
| 2005/0053642 A1* | 3/2005 | Ulbricht ................. A61L 27/34 424/443 |
| 2007/0244558 A1 | 10/2007 | Machiraju |
| 2010/0082101 A1 | 4/2010 | Muratoglu et al. |
| 2011/0166659 A1 | 7/2011 | Luginbuhl et al. |
| 2011/0189475 A1 | 8/2011 | Rizk et al. |
| 2014/0093717 A1 | 4/2014 | James et al. |
| 2014/0094568 A1 | 4/2014 | James et al. |

OTHER PUBLICATIONS

Sperling, "Interpenetrating Polymer Networks: An Overview," in *Interpenetrating Polymer Networks*, Klempner D., et al.,: Advances in Chemistry; American Chemical Society: Washington, DC, pp. 3-38 (1994).

vandeWal, H. et al. "Autologous tissue cardiac valve: Implantation in children." *Journal of Thoracic and Cardiovascular Surgery*, 112:846-848 (1996).

Zhang, M. et al. "A Novel Ultra High Molecular Weight Polyethylene-Hyaluronan Microcomposite for Use in Total Joint Replacements: Synthesis and Physical/Chemical Characterization." *J Biomed Mater Res Part A*. Apr. 6, 2006. vol. 78, No. 1, pp. 86-96. DOI: 10.1002/jbm.A.30701.

Zhang, M. et al. "A Novel Ultra High Molecular Weight Polyethylene-Hyaluronan Microcomposite for Use in Total Joint Replacements: Mechanical and Tribological Property Evaluation." *J Biomed Mater Res Part A*. Jan. 30, 2007. vol. 82, No. 1, pp. 18-26, DOI:10.1002/jbm.a.31141.

Extended European Search Report, EP13760533.3, dated Sep. 16, 2015.

\* cited by examiner

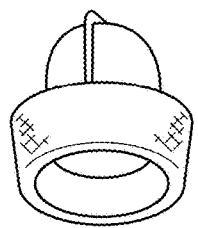 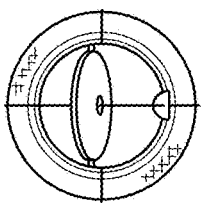 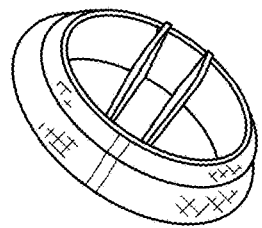
FIG.1A    FIG.1B    FIG.1C
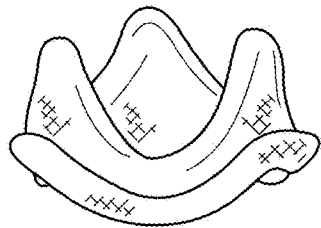 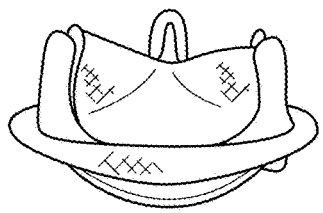 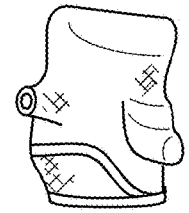
FIG.2A    FIG.2B    FIG.2C

GLYCOSAMINOGLYCAN AND SYNTHETIC POLYMER MATERIAL FOR BLOOD-CONTACTING APPLICATIONS

CROSS-REFERENCE TO RELATED APPLICATIONS

This application claims the benefit under 35 U.S.C. § 119(e) of U.S. Provisional Application Ser. No. 61/609,818 filed Mar. 12, 2012, and is the national stage entry under 35 U.S.C. § 371 of PCT/US2013/30230, filed Mar. 11, 2013, entitled "Glycosaminoglycan and Synthetic Polymer Materials for Blood-Contacting Applications," the discloses of which are which incorporated herein by reference in their entireties.

FIELD OF THE INVENTION

Aspects of the present invention relate to biocompatible materials and medical apparatus and methods. More specifically, the present invention relates to a biocompatible composite, such as an interpenetrating polymer network (IPN), and apparatuses made from those composites, such as heart valves and other devices that contact blood.

BACKGROUND OF THE INVENTION

Heart valve (HV) replacements of diseased cardiac valves by prostheses are common and often lifesaving for patients with significant valvular lesions, stenosis, or regurgitation. Depending on the severity of the condition, HV replacement is an expensive yet critical procedure used to restore proper valve function with an increasing number of replacements each year. For example, in 2012 over 290,000 HV procedures were performed worldwide. That number is estimated to triple to over 850,000 by 2050. Thus, the demand for artificial HVs is expanding at a rate of 10-12% per year. With changing demographics and lifestyle choices, demand for a more durable and biocompatible prosthesis is rising. Factors supporting the need to increase research efforts on HV replacements include, but are not limited to, an increasing United States population over the age of 65 years old, an increasing life expectancy and an increasing occurrence of valvular heart disease.

Mechanical heart valves, which have no biologic component, are thrombogenic, causing thrombus formation and thromboemboli. For this reason, anticoagulation must be robust for mechanical HVs. Bioprosthetic heart valves, made from fixed porcine aortic leaflets or bovine pericardium do not have long-term thrombogenicity problems in patients without other risk factors, but have a shorter lifespan due to poor fatigue characteristics used on the natural tissues. HV replacements are frequently revised due to this tendency for mechanical heart valves to form thrombus and bioprosthetic heart valves lack of durability. The need for improved biomaterials in HV therapy has recently intensified with the advent of minimally invasive approaches, which presently use bioprosthetic HVs in a deployable stent or frame, but suffer from the same drawbacks that plague traditional bioprosthetic HVs. Thus, there is a need to increase the longevity and reduce thrombogenicity of HVs and to reduce the number of revision surgeries performed each year. In particular, an improved hemocompatibility of polymeric heart valve leaflets is needed, which is easy and inexpensive to produce and to surgically implement. Also there is a need for HVs engineered specifically for future minimally invasive HV configuration, and for small-diameter vascular grafts that do not suffer from poor patency due to intimal hyperplasia, and thrombus formation.

BRIEF SUMMARY OF THE INVENTION

The surface chemistry of the polymer is improved for long-term use in vivo. Commercial production of hyaluronan-containing materials is feasible and affordable. The high molecular weight enables production of a composite between hyaluronan and synthetic polymers, maintaining the desirable physical properties of the host polymer, such as its strength and durability, with the added biocompatibility and hydrophilicity of the hyaluronan in a form much more durable than mere surface grafting or coating.

In some embodiments, this disclosure provides a composite, comprising: a polymer host selected from the group consisting of low-density polyethylene (LDPE), linear low-density polyethylene (LLDPE), polyethylene terephthalate (PET), polytetrafluoroethylene (PTFE), and polypropylene (PP), polyurethane, polycaprolactone (PCL), polydimethylsiloxane (PDMS), polymethylmethacrylate (PMMA), and polyoxymethylene (POM); and a guest molecule comprising a glycosaminoglycan (GAG); wherein the guest molecule is disposed within the polymer host, and wherein the guest molecule is covalently bonded to at least one other guest molecule. In particular, the GAG is hyaluronic acid.

The PET may be a fabric. The PTFE may be expanded PTFE (ePTFE). The polymer host may be a film with a thickness of 25 μm to 100 μm, such as 50 μm. The percentage of crystallinity of the composite may be 10% to 65%, such as 25% to 40%.

The percentage of cross-linked guest molecules within the composite is 0.2% to 3.5% or higher. The concentration of guest molecule in the composite may be greater near the surface of the polymer host than at the core of the polymer host, or it may be uniformly distributed throughout the polymer host. The modulus of the composite may be 70 MPA to 100 MPA, or may be substantially similar to the modulus of the polymer host. The elongation to failure of the composite may be 100% to 1000%, such as 450% to 900%. The aqueous contact angle of the composite may be 10° to 90°, such as 40° to 80°. The average molecular weight of the guest molecule may be 0.75 kDa to 1,500 kDa, such as 1 kDa to 10 kDa.

In another embodiment, this disclosure provides A method for preparing a composite, comprising: providing a polymer host selected from the group consisting of low-density polyethylene (LDPE), linear low-density polyethylene (LLDPE), polyethylene terephthalate (PET), and polytetrafluoroethylene (PTFE); protecting a guest molecule comprising hyaluronic with a protecting group before the soaking step; soaking the polymer host in a solution of a protected guest molecule, whereby the guest molecule is disposed within the polymer host; exposing the soaked polymer host to a cross-linking agent, whereby the protected guest molecule is covalently bonded to at least one other protected guest molecule; and deprotecting the protected guest molecule to remove the protecting group. The method may further comprise removing solvent from the soaked polymer host. The method may also further comprise dipping the composite in a second solution of a guest molecule.

The protecting group may be a trialkylsilyl group, such as a trimethylsilyl group. The solvent may be xylenes. The soaking step may occur at a temperature of 25° C. to 100° C., such as 45° C. to 65° C. The soaking step may occur for 10 minutes to 90 minutes, such as for 60 minutes. The concentration of guest molecule in the solution may be 0.5 mg/mL to 250 mg/mL, such as 1.5 mg/mL to 150 mg/mL, or 2.5 mg/mL to 50 mg/mL. The cross-linking agent may be a diisocyanate, such as poly(hexamethylene diisocyanate). The drying step may occur under vacuum.

In still other embodiments, this disclosure provides a blood-contacting device formed from a composite comprising: a polymer host selected from the group consisting of low-density polyethylene (LDPE), linear low-density polyethylene (LLDPE), polyethylene terephthalate (PET), and polytetrafluoroethylene (PTFE); and a guest molecule comprising hyaluronic acid; wherein the guest molecule is disposed within the polymer host, and wherein the guest molecule is covalently bonded to at least one other guest molecule.

The device may be selected from the group consisting of heart valve, vascular graft, intravascular catheter, sensor, stent, annulus, insulator for electrical leads, extracorporeal blood-loop circuit, implantable cardiac assist device for prolonged circulatory support, left ventricular assist device (LVAD), polyethylene braid, artificial cord, tether, suture, peripherally inserted central catheter (PICC) line, fistula plug, membrane, blood bag; blood processing, transportation and storage equipment and materials; Luer connector, aneurysm patch, conduit, coil, roller pump, patent foramen ovale (PFO), reconstruction patch, transapical device, angioplasty tool, cannula, and annuloplasty ring. In a particular embodiment, the device is a heart valve.

The composite, upon contact with blood, may substantially reduce thrombogenesis or substantially improve endothelialization compared to the polymer host without a guest molecule disposed therein. The device may be a vascular graft, particularly wherein polymer host is expanded PTFE (ePTFE) and the vascular graft is a small-diameter vascular graft.

In another embodiment, this disclosure provides a heart valve, comprising: a leaflet formed from a first composite comprising a first polymer host selected from the group consisting of low-density polyethylene (LDPE), linear low-density polyethylene (LLDPE) film and polyethylene terephthalate (PET) fabric, and a first guest molecule comprising hyaluronic acid; wherein the first guest molecule is disposed within the second polymer host, and wherein the first guest molecule is covalently bonded to at least one other guest molecule. The heart valve may further comprise a sewing cuff made from a second composite, comprising a second polymer host comprising PET fabric, and a second guest molecule comprising hyaluronic acid; wherein the second guest molecule is disposed within the second polymer host, and wherein the second guest molecule is covalently bonded to at least one other second guest molecule.

The first polymer host may have a thickness of 25 µm to 100 µm, such as 50 µm. The percentage of crystallinity of the composite may be 10% to 65%, such as 25% to 40%. The percentage of cross-linked guest molecules within the first composite may be 0.2% to 3.5%, or higher. The concentration of first guest molecule in the first composite may be greater at the surface of the first polymer host than at the core of the first polymer host. The modulus of the first composite may be 70 MPA to 100 MPA. The elongation to failure of the first composite may be 450% to 900%. The aqueous contact angle of the first composite may be 40° to 80°. The average molecular weight of the first guest molecule may be 1 kDa to 10 kDa.

In yet another embodiment, this disclosure provides a vascular graft formed from a composite comprising a polymer host comprising polytetrafluoroethylene (PTFE); and a guest molecule comprising hyaluronic acid; wherein the guest molecule is disposed within the polymer host, and wherein the guest molecule is covalently bonded to at least one other guest molecule. In particular, the PTFE may be expanded PTFE, and the vascular graft may be a small diameter vascular graft.

In another embodiment, this disclosure provides a heart valve, comprising: a leaflet formed from first composite comprising a first polymer host selected from the group consisting of low-density polyethylene (LDPE), linear low-density polyethylene (LLDPE) film and polyethylene terephthalate (PET) fabric, and a first guest molecule comprising hyaluronic acid; wherein the first guest molecule is disposed within the second polymer host, and wherein the first guest molecule is covalently bonded to at least one other guest molecule. The heart valve may further comprise a sewing cuff made from a second composite, comprising a second polymer host comprising PET fabric, and a second guest molecule comprising hyaluronic acid; wherein the second guest molecule is disposed within the second polymer host, and wherein the second guest molecule is covalently bonded to at least one other second guest molecule.

In other embodiments, this disclosure provides a heart valve, comprising: a ball formed from a first composite comprising: a first polymer host comprising polyoxymethylene (POM), and a first guest molecule comprising hyaluronic acid; wherein the first guest molecule is disposed within the second polymer host, and wherein the first guest molecule is covalently bonded to at least one other guest molecule; and a cage made from a second composite, comprising: a second polymer host, and a second guest molecule comprising hyaluronic acid; wherein the second guest molecule is disposed within the second polymer host, and wherein the second guest molecule is covalently bonded to at least one other second guest molecule.

Unless otherwise defined, all technical and scientific terms used herein have the same meaning as is commonly understood by one of skill in the art to which this invention belongs at the time of filing. If specifically defined, then the definition provided herein takes precedent over any dictionary or extrinsic definition. Further, unless otherwise required by context, singular terms shall include pluralities, and plural terms shall include the singular. Herein, the use of "or" means "and/or" unless stated otherwise. All patents and publications referred to herein are incorporated by reference.

BRIEF DESCRIPTION OF THE DRAWINGS

FIG. 1 shows three basic types of mechanical heart valves: (a) ball and cage valve, (b) tilting disk valve, and (c) bileaflet valve.

FIG. 2 shows three types of bioprosthetic heart valves: (a) stented porcine valve, (b) stented bovine pericardial valve, and (c) stentless porcine valve.

DETAILED DESCRIPTION

Many medical devices contact blood, including heart valves, vascular conduits, vascular grafts, catheters, tools, and stents. It is desirable that blood-contacting surfaces resist blood clotting and thrombogenesis. The compositions and methods presented herein provide such hemocompatibility, and do so with resilience and great stability.

Figure 43:
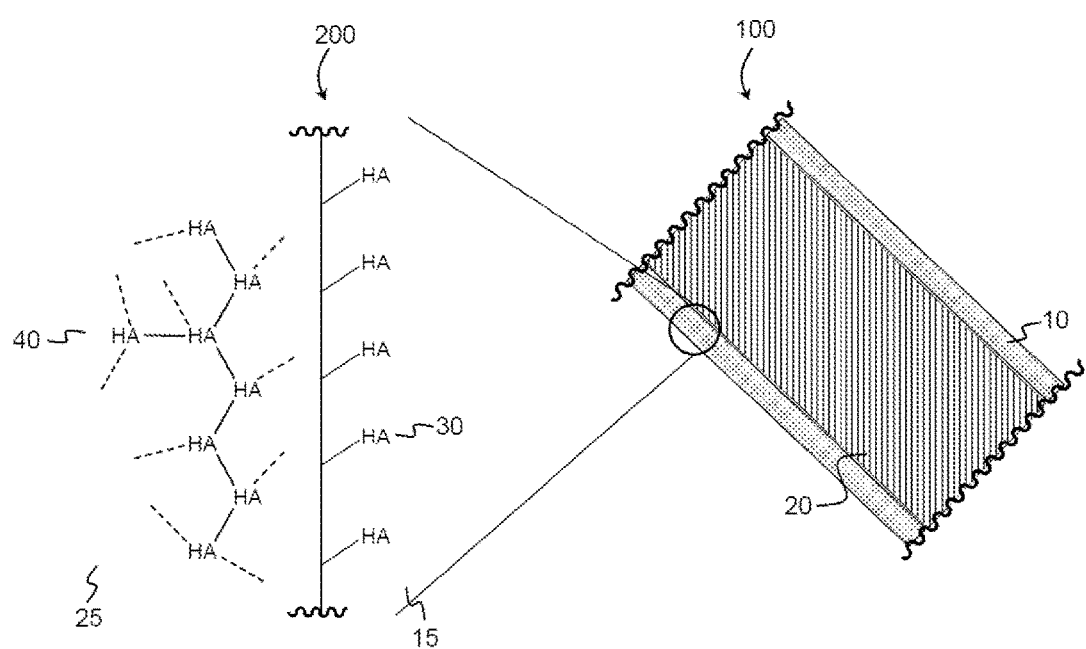
FIG. 43 depicts a cross-section of a medical device, which is coated with a guest molecule and contains a cross-linked guest molecule.

To illustrate this concept, FIG. 43 shows a cross-section 100 of a medical device with surface 10 and substrate 20. Surface 10 is modified with a coating of a guest molecule. Substrate 20 is interpenetrated with a guest molecule. Close-up 200 magnifies a part of cross-section 100. Guest molecule 30 (HA) is covalently bonded to surface 15, forming a coating on surface 15. Beneath the surface, guest molecules are covalently bonded to each other within substrate 25, forming network 40. In this way, the guest molecules 30, 40 are stabilized against unwanted degradation while providing beneficial biological properties, such as resistance to blood clotting and thrombogenesis, or promoting endothelialization. All the while, substrate 20 maintains the mechanical properties that make it useful as a material for constructing medical devices, such as heart valves and vascular stents.

I. Composite

The substrate may comprise a composite. The composite may be an interpenetrating polymer network (IPN), which is an intermingling of protected guest molecule and a polymer host, wherein molecules of the guest have been crosslinked with each other. A composite is a material made from two or more components that are physically blended or mixed together. The components may be covalently bonded to each other or to themselves. In particular, the components may both be polymers. In general, in an IPN, at least one component is synthesized or cross-linked in the presence of the other, although the two components may be bound together. Semi-IPNs fall within the category of IPNs and, thus, composites. The interpenetration many occur at the nanometer scale, the micron scale, or both. "Microcomposite" refers to a composite where the interpenetration of the guest molecule is substantially on the micron scale, but does not preclude interpenetration and crosslinking on the nanometer scale. The term "composite" does not limit the scale on which the polymer host and the guest molecule interact with each other.

The mechanical and physical properties of the composite, such as its percentage of crystallinity, modulus, elongation to failure, and aqueous contact angle, may be substantially similar to the properties of the polymer host. The composite may be amorphous, semi-crystalline, or crystalline. The percentage of crystallinity of the composite may be, for example, about 0% to about 100%, about 5% to about 90%, about 10% to about 65%, such as about 25% to about 40%, about 10% to about 15%, about 15% to about 20%, about 20% to about 25%, about 25% to about 30%, about 30% to about 35%, about 35% to about 40%, about 40% to about 45%, about 45% to about 50%, about 50% to about 55%, about 55% to about 60%, or about 60% to about 65%.

The modulus of the composite may be about 0.1 MPA to about 5200 MPA, for example about 10 MPA to about 900 MPA, about 140 MPA to about 1550 MPA, about 180 MPA to about 500 MPA, or about 1800 MPA to about 5200 MPA. In some embodiments, the modulus of the composite may be about 50 MPA to about 150 MPA, for example about 70 MPA to about 100 MPA, such as about 70 MPA to about 80 MPA, about 80 MPA to about 90 MPA, or about 90 MPA to about 100 MPA. In still other embodiments, the modulus of the composite may be about 0.1 MPA to about 10 MPA, for example about 0.2 MPA to about 1 MPA, such as from about 0.2 MPA to about 0.3 MPA, from about 0.3 MPA to about 0.4 MPA, from about 0.4 MPA to about 0.5 MPA, from about 0.5 MPA to about 0.6 MPA, from about 0.6 MPA to about 0.7 MPA, from about 0.7 MPA to about 0.8 MPA, from about 0.8 MPA to about 0.9 MPA, from about 0.9 MPA to about 1.0 MPA. In yet other embodiments, the modulus of the composite may be about 1800 MPA to about 5200 MPA, such as about 1800 MPA to about 2000 MPA, about 2000 MPA to about 2500 MPA, about 2500 MPA to about 3000 MPA, about 3000 MPA to about 3500 MPA, about 3500 MPA to about 4000 MPA, about 4000 MPA to about 4500 MPA, or about 4500 MPA to about 5000 MPA.

The elongation to failure of the composite may be about 50% to about 1500%, for example about 100% to about 1000%, such as about 200% to about 900%, about 450% to about 500%, about 500% to about 550%, about 550% to about 600%, about 600% to about 650%, about 650% to about 700%, about 700% to about 750%, about 750% to about 800%, about 800% to about 850%, or about 850% to about 900%. In some embodiments, the elongation to failure of the composite may be about 1000% to about 1500%, such as about 1000% to about 1100%, about 1100% to about 1200%, about 1200% to about 1300%, about 1300% to about 1400%, or about 1400% to about 1500%.

The aqueous contact angle on the surface of the composite may about 10° to about 90°, for example about 40° to about 80°, such as about 40° to about 45°, about 45° to about 50°, about 40° to about 45°, about 45° to about 50°, about 50° to about 55°, about 55° to about 60°, about 60° to about 65°, about 65° to about 70°, about 70° to about 75°, or about 75° to about 80°.

A. Polymer Host

In the composite, the polymer host may be any hydrophobic polymer with mechanical properties suitable to the material's application. Examples of suitable polymer hosts include, but are not limited to, polyolefins, such as polyethylene (PE), ultrahigh molecular weight polyethylene (UHMWPE), low-density polyethylene (LDPE), linear low-density polyethylene (LLDPE); polyurethane, polycaprolactone (PCL), polydimethylsiloxane (PDMS), polymethylmethacrylate (PMMA); polyoxymethylene (POM), such as Delrin™; polyesters, such as polyethylene terephthalate (PET) or Dacron™; or polytetrafluoroethylene (PTFE), such as Teflon™. Extrusion and sintering processing techniques may make PTFE more porous, forming expanded PTFE (ePTFE), which is not biodegradable.

The polymer host may be a powder, film, fabric (woven or non-woven), or other bulk form. The polymer host may be molded, ram-extruded, blown, a virgin resin, or an expanded foam. Generally, the polymer host may be porous, such as a fabric, electrospun scaffold, or sintered construct. A polymer host may be swollen in an organic solvent.

In some embodiments, the host may be a non-polymeric material, for example a biological material, such as an allograft, xenograft, tissue, submucosa, swine heart value, a vessel graft, or a skin graft. The biological material may be with or without fixation, such as glutaraldehyde fixation. The host may also be a metal foam, such as a tantalum foam.

The polymer host may be amorphous, semi-crystalline, or crystalline. The percentage of crystallinity of the polymer host may be, for example, about 10% to about 65%, such as about 25% to about 40%, about 10% to about 15%, about 15% to about 20%, about 20% to about 25%, about 25% to about 30%, about 30% to about 35%, about 35% to about 40%, about 40% to about 45%, about 45% to about 50%, about 50% to about 55%, about 55% to about 60%, or about 60% to about 65%

The polymer host may be a film with a thickness of about 25 μm to about 100 μm, for example about 25 μm to about 30 μm, about 30 μm to about 35 μm, about 35 μm to about 40 μm, about 40 μm to about 45 μm, about 45 μm to about 50 μm, about 50 μm to about 55 μm, about 55 μm to about 60 μm, about 60 μm to about 65 μm, about 65 μm to about 70 μm, about 70 μm to about 75 μm, about 75 μm to about 80 μm, about 80 μm to about 85 μm, about 85 μm to about 90 μm, about 90 μm to about 95 μm, about 95 μm to about 100 μm. In a particular embodiment, the film is about 50 μm thick.

By way of example, no clinically acceptable polymeric leaflet valves are available beyond those used short-term in artificial hearts. Polyurethanes have been used in these devices because they exhibit acceptable mechanical properties and performance in the short-term, however, they tend to be very vulnerable to many types of biodegradation and have a tendency to calcify and eventually tear and fail which has limited their successful use. Polycarbonate urethane valves were developed to optimize hemodynamics with the goal to increase durability, but the material does not prevent calcification. A material originally developed for vascular grafts, 2% polyhedral oligomeric silsesquioxane-polycarbonate-urea urethane (POSS-PCD), shows good mechanical properties due to the addition of the POSS. However, both the PCD and the POSS-PCD are hydrophobic, with water contact angles over 100 degrees. Both valves exhibit calcification during in vitro performance.

ePTFE grafts are commonly used in bypass procedures of the lower limbs where arteries are 7-9 mm in diameter. Additionally, ePTFE grafts have been used for hemodialysis access in patients with renal failure. ePTFE grafts do not develop an endothelial cell layer, potentially leading to thrombus formation. However, the patency of ePTFE grafts in femoropopliteal grafts was determined to be about 45%, whereas the patency of autologous vein grafts was about 77%. ePTFE grafts are generally preferred for peripheral artery bypass in the UK, but many studies have not shown a difference in long-term patency between ePTFE and PET grafts.

B. Guest Molecule

A main reason for long-term failure of blood-contacting devices is thrombus formation at an early stage followed by excessive tissue ingrowth at a later stage. An effective way to prevent thrombus formation and enhance vascular graft performance is to encourage the endothelial cells (ECs) to re-grow over the blood-contacting device. This process where a thin layer of tissue lining forms over the device surface is called endothelialization. The process of endothelialization is critical to enhance the biocompatibility as well as the anti-thrombogenecity of the device after implantation. ECs release factors that control the thrombogenesis, fibrinolysis and platelet activation/inhibition. A key to endothelial cell functionality is their proliferation on vascular graft surfaces.

A guest molecule may provide these beneficial biological properties, including resistance to thrombogenesis and enhanced endothelialization. The guest molecule may comprise a compound selected from the group consisting of polyions, polysaccharides including glycosaminoglycans (GAGs); salts of glycosaminoglycans, nucleic acids, polyvinylpyrrolidones, peptides, polypeptides, proteins, lipoproteins, polyamides, polyamines, polyhydroxy polymers, polycarboxy polymers, phosphorylated derivatives of carbohydrates, sulfonated derivatives of carbohydrates, interleukin-2, interferon, and phosphorothioate oligomers, with or without amino acids, as well as other hydrophilic polymers. Polyhydroxy polymers include, for example, polyvinyl alcohol and polyethylene glycol. Polycarboxy polymers include, for example, carboxymethylcellulose, alginic acid, sodium alginate, and calcium alginate.

In some embodiments, the guest molecule may be any glycosaminoglycan (GAG). GAGs include any of a group of linear polysaccharides with various disaccharide repeating units and usually occurring in proteoglycans, including chondroitin sulfate, dermatan sulfate, heparan sulfate, and heparin, keratan sulfates, and hyaluronic acid. GAGs may be high molecular weight, low molecular weight, or oligomeric. GAGs or mucopolysaccharides are long unbranched polysaccharides consisting of a repeating disaccharide unit. The repeating unit consists of a hexose (six-carbon sugar) or a hexuronic acid, linked to a hexosamine (six-carbon sugar containing nitrogen). In a particular embodiment, the GAG is a chondroitin sulfate or a hyaluronan, such as hyaluronic acid.

Hyaluronan ("hyaluronic acid" or "HA") is a naturally occurring polysaccharide found in tissues and body fluids of vertebrates and in some bacteria. It is a linear polymer with high molecular weight linear polysaccharide containing alternating N-acetyl-D-glucosamine and D-glucuronic acid residues, with relatively high concentrations in the vitreous humor of eye, the umbilical cord, synovial joint fluid, rooster combs, and in native heart valve leaflets, particularly those regions of the valve subject to compression. A carboxyl group (—COOH) is attached to each disaccharide unit of hyaluronic acid. When in solution at physiological pH, hyaluronic acid is ionized, resulting in negatively charged —COO. The negatively charged flexible chains take on an expanded conformation and entangle with each other at very low concentrations, acting as a stiff random coil. In solutions with higher concentration of hyaluronic acid, stiff random coils entangle, forming viscoelastic solutions retaining flow without gelling.

Hyaluronan solutions are viscous at low shear rates, but elastic at high shear rates. Hyaluronic acid's molecular structure leads to its viscoelastic property, hydrophilicity, and lubricity. Use of HA in a composite is more durable than heparin surface treatments and coatings. HA is easily produced commercially via fermentation and its availability in high molecular weights results in composites with large, relatively mobile HA molecules at the surface which should enhance antithrombogenicity and permit efficient, cost-effective commercial scale-up. HA is also available in oligomeric forms, which permits tuning to different biological effects than the higher molecular weight species.

HA is known to bind to three different receptors on ECs: CD44, hyaluronan-mediated motility receptor (RHAMM), and toll-like receptor 4 (TLR4). CD44 is a cell-surface glycoprotein involved in cell-cell interactions, cell adhesion and migration. RHAMM normally is localized inside the cell and may be involved in transport channels or proteins, flippase activity, and exocytosis. Intracellularly, RHAMM is associated with microtubules and plays a role in the regulation of mitosis. Extracellularly, RHAMM is associated with CD44, and upon binding to HA, activates intracellular signaling pathways. TLR4 plays a fundamental role in pathogen recognition and activation of innate immunity, recognizing pathogen-associated molecular patterns expressed on infectious agents, and mediating the production of cytokines necessary to develop effective immunity. ECs show enhanced expression of CD44 and TLR4 under inflamed conditions. The interaction of CD44 receptor with HA has been shown to enhance the production of VEGF and thus promotes cell proliferation. The chain length of HA molecules may significantly affect its interaction with these receptors on ECs. Longer chain HA molecules will most likely have ligands for these receptors which are not as accessible as those on shorter chain HA molecules. HA may also regulate embryonic development, tissue organization, wound healing and angiogenesis.

Salt complexes of hyaluronic acid may be used in forming the composite. Examples of suitable cations include, but are not limited to, alkyltrimethylammonium chloride, alkylamine hydrochloride, alkylpyridinium chloride, alkyldimethylbenzyl ammonium chloride, alkyltrimethylammonium bromide, alkylamine hydrobromide, alkylpyridinium bromide, and alkyldimethylbenzyl ammonium bromide. Optionally, the HA is temporarily protected with a protecting group.

HA may be present in the composite from about 0.001% to about 15% by weight, or 0.2% to about 1.5% by weight. In some embodiments, the HA concentration is from about 0.2% to about 10% by weight, such as about 5% to about 10% by weight, about 0.5% to about 3.5% by weight, about 0.5% to about 1.0% by weight, about 1.0% to about 1.5% by weight, about 1.5% to about 2.0% by weight, about 2.0% to about 2.5% by weight, about 2.5% to about 3.0% by weight, about 3.0% to about 3.5% by weight, about 3.5% to about 4.0% by weight, about 4.0% to about 4.5% by weight, about 4.5% to about 5.0% by weight, about 5.5% to about 6.0% by weight, about 7.0% to about 7.5% by weight, about 7.5% to about 8.0% by weight, about 8.0% to about 8.5% by weight, about 8.5% to about 9.0% by weight, about 9.0% to about 9.5% by weight, or about 9.5% to about 10.0% by weight. In other embodiments, the HA concentration in the composite may be about 0.2%, about 0.3%, about 0.4%, about 0.5%, about 0.6%, about 0.7%, about 0.8%, about 0.9%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, or about 3.5%.

C. Crosslinking Agents

The guest molecules are crosslinked to each other within the polymer host. To achieve crosslinkage, crosslinking agents are used, such as aliphatic polyisocyanates include, for example, bis(4 isocyanatocyclohexyl) methane ($H_{12}$MDI) such as available from Bayer Corp., Pittsburgh, Pa. under the trade designation Desmodur™ W; isophorone diisocyanate (IPDI) such as commercially available from Huels America, Piscataway, N.J.; hexamethylene diisocyanate (HDI) such as commercially available from Aldrich Chemical Co., Milwaukee, Wis.; trimethylhexamethylene diisocyanate such as commercially available from Degussa, Corp., Dusseldorf, Germany under the trade designation Vestanate™ TMDI; and m-tetramethylxylene diisocyanate (TMXDI) such as commercially available from Aldrich Chemical Co., Milwaukee, Wis. Although typically less preferred, aromatic isocyanates such as diphenylmethane diisocyanate (MDI) such as commercially available from Bayer Corp., Pittsburgh, Pa. under the trade designation Mondur™ M; toluene 2,4-diisocyanate (TDI) such as commercially available from Aldrich Chemical Co., Milwaukee, Wis., and 1,4-phenylene diisocyanate are also useful.

Polyisocyanates include derivatives of the above-listed monomeric isocyanates. These derivatives include, but are not limited to, polyisocyanates containing biuret groups, such as the biuret adduct of hexamethylene diisocyanate (HDI) available from Bayer Corp. under the trade designation Desmodur™ N-100, polyisocyanates based on HDI containing isocyanurate groups, such as that available from Bayer Corp. under trade designation Desmodur™ N-3300, as well as polyisocyanates containing urethane groups, uretdione groups, carbodiimide groups, allophonate groups, and the like. These derivatives are preferred as they are polymeric, exhibit very low vapor pressures and are substantially free of isocyanate monomer. Other polyisocyanates that may be used are available from Bayer Polymers LLC of Pittsburgh, Pa. under the trade designations Desmodur™ TPLS2294 and Desmodur™ N 3600.

In a particular embodiment, the GAG may be crosslinked at the carboxylic acid groups and/or hydroxyl groups using poly(ethylene glycol)diglycidyl ether. Desmodur™ N-3200, a biuret isocyanate derived from hexamethylene diisocyanate, crosslinks hyaluronic acid at the hydroxyl groups, rather than the carboxylic acid groups, preserving hyaluronic acid's lubricity.

Different sized GAGs, such as cross-linked HA molecules, may induce different signaling mechanisms in ECs to promote their adhesion and proliferation. The molecular weight ranges for the cross-linked guest molecules may be varied based on cross-linking conditions and the desired biological effect. In some embodiments, the guest molecule may have a large molecular weight, for example from about 10 kDa to about 1 MDa, such as from about 10 kDa to about 50 kDa, from about 50 kDa to about 100 kDa, from about 100 kDa to about 200 kDa, from about 100 kDa to about 200 kDa, from about 100 kDa to about 200 kDa, from about 200 kDa to about 300 kDa, from about 300 kDa to about 400 kDa, from about 400 kDa to about 500 kDa, from about 600 kDa to about 700 kDa, from about 800 kDa to about 900 kDa, or from about 900 kDa to about 1,000 kDa (1 MDa). In other embodiments, the guest molecule may have a molecular weight from about 1 kDa to about 15 kDa, for example from about 1 kDa to about 10 kDa, such as from about 1 kDa to about 2 kDa, from about 2 kDa to about 3 kDa, from about 3 kDa to about 4 kDa, from about 4 kDa to about 5 kDa, from about 5 kDa to about 6 kDa, from about 6 kDa to about 7 kDa, from about 7 kDa to about 8 kDa, from about 8 kDa to about 9 kDa, or from about 9 kDa to about 10 kDa. In yet other embodiments, the guest molecule may be oligomeric, comprising from about 2 to about 15 monomeric units of guest molecules, for example, 6 units or 12 units. In this embodiment, the molecular weight of the oligomeric crosslinked guest molecule is about 0.75 kDa to about 10 kDa, such as for example about 0.75 Da to 1 kDa, from about 1 kDa to about 2 kDa, from about 2 kDa to about 3 kDa, from about 3 kDa to about 4 kDa, from about 4 kDa to about 5 kDa, from about 5 kDa to about 6 kDa, from about 6 kDa to about 7 kDa, from about 7 kDa to about 8 kDa, from about 8 kDa to about 9 kDa, or from about 9 kDa to about 10 kDa.

D. Method of Making the Composite

The host polymer may be soaked in a solution of the protected guest molecule. Depending on the nature of the polymer host, the polymer host may swell as it absorbs the solution and the guest molecule diffuses into the host polymer. The polymer host may also wick the soaking solution, such that the solution fills interstitial spaces within the physical structure of the polymer host. The solution may be prepared from a solvent, such as supercritical carbon dioxide, toluene, decalin, trichlorobenzene, or xylenes, and combinations thereof. In a particular embodiment, the solvent is xylenes Viscosity of the soaking solution may be selected to control the rate of diffusion of the guest molecule in to the polymer host.

In a particular embodiment, sodium hyaluronic acid was complexed with quaternary an ammonium cation, hexadecyltrimethylammonium bromide, followed by silylation with hexamethyldisilazane to produce silyl HA-CTA. Silylating the hyaluronic acid increases the hydrophobicity of the GAG, by replacing the active hydrogens of the hydroxyl groups and amino groups with trimethylsilyl groups. After soaking and crosslinking, the protecting group is removed to free the hydroxyl groups and amino groups of the hyaluronic acid. After deprotection, the polymerized guest molecule is typically hydrophilic.

The soaking step may occur at a temperature of about 25° C. to about 100° C., for example about 45° C. to about 65°

C., such as about 45° C. to about 50° C., about 50° C. to about 55° C., about 55° C. to about 60° C., or about 60° C. to about 65° C.

The soaking step may occur for about 10 minutes to about 90 minutes, such as about 10 minutes to about 15 minutes, about 15 minutes to about 20 minutes, about 20 minutes to about 25 minutes, about 25 minutes to about 30 minutes, about 30 minutes to about 35 minutes, about 35 minutes to about 40 minutes, about 40 minutes to about 45 minutes, about 45 minutes to about 50 minutes, about 50 minutes to about 55 minutes, about 55 minutes to about 60 minutes, about 60 minutes to about 65 minutes, about 65 minutes to about 70 minutes, about 70 minutes to about 75 minutes, about 75 minutes to about 80 minutes, about 80 minutes to about 85 minutes, or about 85 minutes to about 90 minutes. In a particular embodiment, the soaking step takes about 60 minutes.

Any concentration below the guest molecule's solubility limit in the selected solvent may be used. In some embodiments, the concentration of guest molecule in the solution may be about 0.5 mg/mL to about 250 mg/mL, for example about 1.5 mg/mL to about 150 mg/mL, or about 2.5 mg/mL to about 50 mg/mL, such as about 2.5 mg/mL to about 5.0 mg/mL, about 5.0 mg/mL to about 10.0 mg/mL, about 10.0 mg/mL to about 15.0 mg/mL, about 15.0 mg/mL to about 20.0 mg/mL, about 20.0 mg/mL to about 25.0 mg/mL, about 25.0 mg/mL to about 30.0 mg/mL, about 30.0 mg/mL to about 35.0 mg/mL, about 35.0 mg/mL to about 40.0 mg/mL, about 40.0 mg/mL to about 45.0 mg/mL, or about 45.0 mg/mL to about 50.0 mg/mL.

After formation, the polymer host may be thermally molded in the presence of the protected guest molecule then cross-linking simultaneously. A diffusion profile of the composite, with its gradual concentration of guest from the outer surface a depth, d, provides structural integrity of the surface and its associated structure by removing the sharp change in modulus inherent in superficially coating or grafting a surface according to known techniques. Crosslinking to finally produce the composite may be done chemically, thermally, or photochemically.

E. Surface Modification

Surfaces may be modified to improve their performance and biocompatibility, such as their hemocompatibility. Glycosylated surfaces may mimic the biochemical activity of the glycocalyx of the blood vessel lumen, which presents heparin-like GAGs. GAGs, particularly heparin, improve hemocompatibility of surfaces. Numerous synthetic plastics and metals that have been modified with heparin show improved hemocompatibility. Hyaluronan and chondroitin sulfate are GAGs used as coatings to reduce platelet adhesion in small diameter vascular grafts. For example, grafting sulfonated polyethylene oxide to the surface of polyurethane reduces calcification and thromboembolism. Increasing hydrophilicity of glutaraldehyde-fixed bioprosthetic tissue valves may decrease calcification and thromboembolism.

Formula (I) represents an unprotected hyaluronic acid.

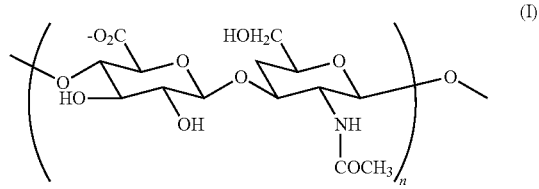

(I)

Possible counterions, generically referred to as "QN+", include, but are not limited to, cetyltrimethylammonium bromide (Formula II) and cetylpyridinium chloride (Formula III). Reaction with the QN+ produces the hyaluronan salt complex $HA^{2-}QN^+$ (Formula IV), which may be protected by reaction with a trimethylsilylation agent, such as chlorotrimethylsilane or hexamethyldisilazane, to yield a trimethylsilane-protected (TMS-protected) hyaluronan salt complex (Formula V). By protecting $HA^{2-}QN^+$ complexes, hydrophilic groups are replaced with silylated functional groups; the hydrogens on the hydroxyl groups and on the amine are replaced with the TMS groups.

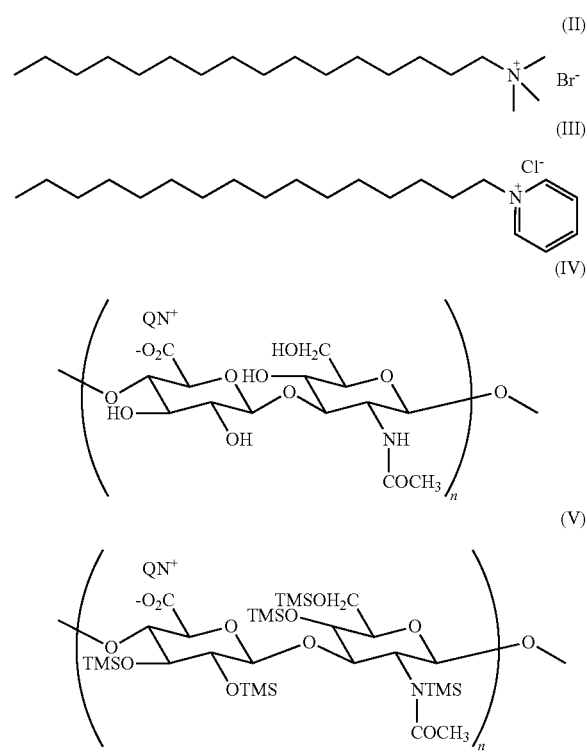

II. Devices

A composite may be used to manufacture devices used in or contacting the body of a mammal, for example inside a human body. In some embodiments, the composite-containing device contacts blood. In other embodiments, the composite may be used to produce heart valves. In yet other embodiments, the composite may be used to produce vascular grafts, such as small-diameter vascular grafts.

A. Heart Valves and Vascular Grafts

Valvular heart disease can be the result of either congenital or developed defects, including rheumatic fever, endocarditis, calcific degeneration, or congenital anomalies. The two largest problems associated with valvular disease are regurgitation and stenosis. In the former case, the valve does not close completely, and some of the pumped blood flows backwards back into the left ventricle. In the latter case, the opening through which blood can pass becomes narrowed due to the leaflets either becoming rigid or fused together. Both of these valvular diseases result in blood accumulation in the chamber, and the heart must work harder to supply the body. This increased workload leads to the thickening of the heart muscle and dilatation, which can result in congestive heart failure. Once the heart valve no longer maintains its normal functionality, drugs can be used to relieve the symptoms but not reverse and disease. Valve replacement surgery is recommended when damage to the valve is considered to be significant enough to pose a life threatening risk.

Complete replacement of damaged and diseased heart valves by prostheses is routine. Factors used to determine which valve is most suited to a patient include the patient's age, comorbidities, need for associated procedures, availability of a given replacement, patient agreement, and surgeon expertise. Current commercially available valves are divided into two primary classes, mechanical and bioprosthetic, each with its associated advantages and disadvantages.

(1) Mechanical Heart Valves

Due to their high durability and longevity, mechanical valves are preferred for individuals under the age of 65. Current designs implanted include the tilting disc design (FIG. 1B), the bileaflet design (FIG. 2C), and to a lesser extent, the ball and cage design (FIG. 1A). The low profile of the bileaflet mechanical valves allows them to be implanted into smaller hearts without obstruction of other structures such as the mitral valve or coronaries. Bileaflet valve have good hemodynamics with low transvalvular pressure gradient is and minimal regurgitation. They are durable, showing a low rate of mechanical failure. The tilting disc valves are the second most commonly implanted mechanical valves. Like the bileaflet valves, the tilting disc valves have shown to be durable, but the hemodynamics of the tilting disk valves is not ideal with lower effective orifice areas and turbulent flow around the disk. The caged ball valve does not have as favorable hemodynamics as the bileaflet and tilting disc valves, but it is still sometimes used when surgeons require a valve that is easy to handle under difficult surgical circumstances. One common problem for all the mechanical valve designs is the resulting partial obstruction of blood flow, leading to non-physiological hemodynamic characteristics, which contribute to thrombosis, embolism, and bleeding complications, often resulting to morbidity and mortality. Consequently, patients receiving mechanical valves are subjected to life-long anticoagulation therapy. Lifetime anticoagulation therapy has many problems associated with it often resulting in either under or over anticoagulation, and complication associated with hemorrhaging.

(2) Bioprothestic Heart Valves

The two main bioprosthetics heart valves are either homografts (from human cadavers) or xenografts, such as glutaraldehyde-fixed procine aortic valves and glutaraldehyde-fixed bovine pericardium (FIG. 2). The homografts are the least frequently used due to a shortage in number and size and their difficulty to insert. The stented porcine (FIG. 2A) and bovine pericardium (FIG. 2B) valves are the most commonly implanted. Both valves have issues with durability with an approximate lifespan of 10-15 years. The trileaflet design reproduces the central flow characteristics of the natural valve and is less thrombogenic than mechanical valves. Thus, long-term anticoagulation treatment is not required for most recipients. Bioprosthetic valves have also become a popular choice for younger patients to prevent the need for lifetime anticoagulation therapy at such a young age, but this often means additional surgeries to replace deteriorating bioprosethetic valves at a later age.

Metallic or polymer structures may be used to support the porcine and bovine pericardium valves. This stent allows the valve to be implanted easily, however, this results in a stenotic region caused by partial orifice obstruction. Stentless porcine valves (FIG. 2C) were developed to help combat this obstruction. The stentless valves consist of aortic roots modified with a sewing ring, which is either implanted within the native root or replaces the root with an increase in effective orifice area. Stentless valves are significantly more complicated to implant than the stented version, and conclusive long-term data of durability of these valves is still unknown but assumed to be similar to stented bioprosthetic valves. Porcine valves are much more restrictive on design due to the valve anatomy. Stented pericardial valves can be fabricated in to much more complex designs. Pericardial valves are fabricated from glutaraldehyde-fixed sheets of bovine pericardium that can be oriented to mimic the natural valve in both form and function. The pericardial valves tend to have more desirable hemodynamics than the porcine valves as a result of their improved effective orifice area and leaflet dynamics during forward flow; however, the traditional designs have been made to exhibit significantly higher stresses during diastole when they are under tension.

The main problem with xenogenic prostheses is tissue failure, which usually is onset within 10 years of implantation. This degradation of the valve is as a result of mechanical damage, calcification, or a combination of both, and has been linked to the glutaraldehyde fixation and the stent-valve interaction. Glutaraldehyde treatment effectively cross-links the tissue and reduces its antigenicity while preventing proteolytic degradation. As a result, the tissue loses its mechanical compliance causing an increase in leaflet stress concentrations, accelerating fatigue of the tissue. The presence of calcium deposits on the leaflets can result in stenosis and leaflet tearing.

The composite of the present disclosure may be used in any component of a heart valve. For example, the composite may be used in a heart valve leaflet, a sewing ring, sewing cuff, a tilting disc, stent, suture ring, or annulus. One of skill in the art would understand how to modify the design of the valve based on the nature of the composite, for example the shape of the leaflet, including its three-dimensional curvature, thickness, uniformity, stent post asymmetry, and profile height. Other design modifications may include the absence of sutures to install leaflets into the heart valve stent. Stents may be formed from the composite, and the whole HV may be molded in a single piece or manufactured by three-dimensional printing.

In some other embodiments, this disclosure provides a heart valve using a tilting disc mechanism. The tilting disk may be formed from a first composite comprising: a first polymer host, such as ultra-high molecular weight polyethylene (UHMWPE), and a first guest molecule comprising hyaluronic acid; wherein the first guest molecule is disposed within the second polymer host, and wherein the first guest molecule is covalently bonded to at least one other guest molecule. The heart valve may also comprise a suture ring made from a second composite, comprising: a second polymer host comprising PET fabric, and a second guest molecule comprising hyaluronic acid; wherein the second guest molecule is disposed within the second polymer host, and wherein the second guest molecule is covalently bonded to at least one other second guest molecule.

In other embodiments, this disclosure provides a heart valve using a ball-in-cage mechanism. The ball may be formed from a first composite comprising: a first polymer host, such as polyoxymethylene (POM), and a first guest molecule comprising hyaluronic acid; wherein the first guest molecule is disposed within the second polymer host, and wherein the first guest molecule is covalently bonded to at least one other guest molecule. The heart valve may further comprise a cage made from a second composite. The second polymer host may be selected as to have the desired physical or mechanical properties. The second guest molecule may comprise hyaluronic acid; wherein the second guest molecule is disposed within the second polymer host, and wherein the second guest molecule is covalently bonded to at least one other second guest molecule.

(3) Vascular Grafts

The two synthetic grafts most commonly used for small diameter bypass procedures for vessels less than 6 mm are PET and ePTFE. Polyurethane materials may also be used in peripheral bypass procedures due to their mechanical property matching to natural vessels. PET and ePTFE grafts often fail due to early thrombosis or late intimal hyperplasia, are more stiff and have a different elastic modulus than natural arteries.

PET is used to treat large diameter vascular grafts but has low patency as a small diameter vascular graft, particularly for lower limb bypass procedures. Untreated PET grafts do not develop an endothelial cell layer on the lumen when implanted, leading to platelet adhesion, fibrin layer formation, and potentially subsequent thrombosis.

ePTFE grafts are commonly used in bypass procedures of the lower limbs where arteries are 7-9 mm in diameter. Additionally, ePTFE grafts have been used for hemodialysis access in patients with renal failure. ePTFE grafts do not develop an endothelial cell layer, either, potentially leading to thrombus formation. Patency of ePTFE grafts in femoropopliteal grafts was determined to be 45%, whereas the patency of autologous vein grafts was 77%. ePTFE grafts may be used for peripheral artery bypass, but most studies have not shown a difference in long-term patency between ePTFE and PET grafts.

Polyurethane may be used in small diameter vascular grafts because mechanical properties can be tailored to match those of native blood vessels. Particularly, polyurethane is more compliant than ePTFE. Polyurethane has been used in hemodialysis, and may be modified with NO-releasing peptides to inhibit platelet activation. Polyurethane materials may be susceptible to degradation in vivo and subsequent aneurismal degeneration.

Poor long-term performance may be low compliance and a lack of functional endothelial cell coverage. Intimal hyperplasia is characterized by migration of smooth muscle cells from the media to the intima. After migration, smooth muscle cells synthesize matrix proteins and other extracellular material. This can cause the blood vessel to become stenosed. A mismatch between compliance of synthetic and natural vessels may contribute to intimal hyperplasia formation at the downstream anastomosis. Patency has been correlated to compliance. Viscoelastic properties are important at low flow rates, such as in the peripheral arteries below the knees. Intimal hyperplasia may develop when blood flow is disrupted and vessel walls are injured. A compliance mismatch may alter the haemodynamics at the anastomosis. Specifically, a compliance mismatch at the anastomosis can increase shear stress under flow conditions, reducing perfusion and potentially leading to rupture. Synthetic grafts may become less compliant upon implantation. Post-implantation stiffening should be considered when matching mechanical properties.

A layer of endothelial cells on the surface of the graft in contact with blood may reduce thrombosis and increase the patency of synthetic vascular grafts. Surface treatments used improve cell retention include attachment of RGD peptides, matrix proteins (fibronectin), growth factors (fibroblast growth factor or endothelial cell growth factor), or a combination of coatings. Endothelial cell coverage is important because it may limit inflammation. Anti-coagulant phenotype endothelial cells produce vasoprotective factors. They also inhibit the production of factors that cause inflammation. One such factor, inducible nitric oxide (iNOS), forms NO and decreases the adhesion of platelets. Another factor, tissue factor (TF), is a procoagulant protein, which, in combination with fVIIa, activates FX and leads to the production of thrombin. Tissue plasminogen activator (tPA) plays a role in plasminogen activation, fibrinolysis, and fibrin clot degradation. Vascular cell adhesion molecule 1 (VCAM-1) supports white blood cell adhesion, including monocytes and lymphocytes. A lack of functional endothelial cell coverage on the lumen surface of a graft leads to thrombosis and subsequent occlusion of the vessel.

Grafts that have surface thrombogenicity and limited biocompatibility at the graft/vessel interface lead to low patency rates. The smaller the graft diameter, the higher the rate of graft occlusion. Several factors may contribute to graft thrombosis, including graft surface properties, graft hemodynamics, blood flow, surgical technique, patient thrombotic profile, and the degree of neointimal formation and endothelialization. Thrombogenesis causes occlusion and decreases blood flow through veins and arteries, possibly causing failure or vessel narrowing, such as stenosis and intimal hyperplasia.

B. Other Devices

In some embodiments, the composite may be used in vascular grafts, including venous grafts and arterial grafts. The grafts may be formed from any polymer host, such as PET, PE, PP, or PTFE, especially ePTFE, or the graft made from allograft tissue or decelluralized xenograft tissue.

As discussed above in Section I(A)(3), composites may be used to form small-diameter vascular grafts. Currently, in limited situations, autografts or allografts may be used, but are unsuitable in most applications. Thus, there is a long-felt and unmet need for the easily produced, high-performing small-diameter vascular grafts made from the composites provided herein, especially grafts which do not suffer from narrowing such as stenosis or intimal hyperplasia.

In other embodiments, the composite may be used in, for example, an intravascular catheter, blood-contacting sensor, stent, annulus, an insulator for electrical leads, an extracorporeal blood-loop circuit; implantable cardiac assist devices for prolonged circulatory support, such a left ventricular assist device (LVAD); a blood-contacting cardiomyopathy treatment, such polyethylene braids, for example an artificial cord, tether, or suture inside a heart; peripherally inserted central catheter (PICC) line, fistula plug, membrane, blood bag; blood processing, transportation and storage equipment and materials; Luer connector, suture, aneurysm patch, conduit, coil, roller (peristaltic) pump, patent foramen ovale (PFO), reconstruction patch, transapical device, angioplasty tools, cannulae, and annuloplasty rings.

The insulator for electrical leads may be present in, for example, a pacemaker or defibrillator. The blood oxygenator may be part of a heart-lung machine, perfusion unit, or hemodialysis machine. Stents may include a coronary artery stent or vascular stent, as well as other angioplasty devices and tools used for stent delivery, such as balloons. Substrates may be for any in vitro diagnostic tool or assay, for example, tissue culture plate, 3D tissue cultures, microfluidics, or a lab-on chip device.

III. Definitions

As used herein, the terms "about" and "approximately" designate that a value is within a statistically meaningful range. Such a range can be typically within 20%, more typically still within 10%, and even more typically within 5% of a given value or range. The allowable variation encompassed by the terms "about" and "approximately" depends on the particular system under study and can be readily appreciated by one of ordinary skill in the art.

As used herein, the term "w/w" designates the phrase "by weight" and is used to describe the concentration of a particular substance in a mixture or solution.

As used herein, the term "ml/kg" designates milliliters of composition per kilogram of formula weight.

As used herein, the term "monomer" refers to any chemical compound that is capable of forming a covalent bond with itself or a chemically different compound in a repetitive manner. The repetitive bond formation between monomers may lead to a linear, branched, super-branched, or three-dimensional product. Furthermore, monomers may themselves comprise repetitive building blocks, and when polymerized the polymers formed from such monomers are then termed "block polymers". Monomers may belong to various chemical classes of molecules including organic, organometallic or inorganic molecules. The molecular weight of monomers may vary greatly between about 40 Dalton and 20000 Dalton. However, especially when monomers comprise repetitive building blocks, monomers may have even higher molecular weights. Monomers may also include additional reactive groups.

Contemplated polymers may also comprise a wide range of functional or structural moieties, including aromatic systems, and halogenated groups. Furthermore, appropriate polymers may have many configurations, including a homopolymer, and a heteropolymer. Moreover, alternative polymers may have various forms, such as linear, branched, super-branched, or three-dimensional. The molecular weight of contemplated polymers spans a wide range, typically between 400 Daltons and 400,000 Daltons, and may be greater than 1,000,000 Daltons or more, in some embodiments.

"Wettability" refers to the ability of a liquid, such as water, to spread on a solid surface. "Hydrophilic" and "hygrophilic" refer to an intrinsic or average chemical property of a surface or bulk solid to allow a polar liquid, such as water, to spread on the surface, with typical water contact angles from about 0° to about 90°. "Hydrophobic" refers to an intrinsic or average chemical property of a surface or bulk solid that prevents a polar liquid, such as water, from spreading on the surface, with typical water contact angles from about 90° to about 180°, such as from about 100° to about 150°. When the surface roughness enhances or reduces the hydrophilic or hydrophobic properties of a surface or bulk solid, the effect is "parahydrophilic" or "parahydrophobic," respectively. For very rough surfaces, the enhancement or reduction in hydrophilic or hydrophobic properties of the surface or bulk solid may be very great; the effect is referred to as "superhydrophilic" or "superhydrophobic," respectively. Surface roughness is usually defined on the microscopic or molecular scales. For further definition of wettability and surface classifications, please refer to Marmur, "Hydro-hygro-oleo-omni-phobic? Terminology of wettability classification," *Soft Matter*, 8:6867 (2012), which is incorporated herein by reference in its entirety.

The compounds described herein have asymmetric centers. Compounds of the present disclosure containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "allyl," as used herein not only refers to compound containing the simple allyl group ($CH_2$=CH—$CH_2$—), but also to compounds that contain substituted allyl groups or allyl groups forming part of a ring system.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting a particular moiety, wherein the protecting group may be removed, subsequent to the reaction for which the protection is employed, without disturbing the remainder of the molecule. Where the moiety is an oxygen atom (and hence, forming a protected hydroxy), exemplary protecting groups include ethers (e.g., allyl, triphenylmethyl (trityl or Tr), p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. When the moiety is an nitrogen atom (and hence, forming a protecting amine) exemplary protecting groups include benzyl, p-methoxyphenyl (PMP), 3,4-dimethoxybenxyl (PMB)), n-silyl groups, esters (e.g., benzoate (Bz), carbonyl (e.g. p-methoxybenzyl carbonyl (Moz), tert-butyloxycarbonyl (BOC), 9-fluorenylmethyloxycarbonyl (FMOC)), acetyl, carbamates, n-silyl groups and the like. A variety of protecting groups and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro and thio.

When introducing elements of the present disclosure or the exemplary embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the disclosure in detail, it will be apparent that modifications and variations are possible without departing from the scope of the disclosure defined in the appended claims.

EXAMPLES

Example 1: Swelling of the Host Polymer

To form hyaluronic acid (HA) in a linear low-density polyethylene (LLDPE) polyethylene terephthalate (PET), or expanded polytetrafluoroethylene (ePTFE) microcomposite, the degree of swelling and swelling kinetics in a solvent of interest were analyzed. A study was performed to understand the above parameters for the swelling of the LLDPE in a range of solvent temperatures in order to identify the swelling parameters to be used in the microcomposite synthesis.

LLDPE samples were blow-molded from known resins by Flex-Pack Engineering, Inc. (Uniontown, Ohio) with known melt indexes, densities, and crystallinities. Samples had a specified thickness of 0.002" (0.0508 mm) without additional fillers or surface treatment. The first type of LLDPE used was film molded from Dowlex™ 2344 resin with a melt index of 0.7 g/10 min, a density of 0.933 g/cm$^3$ and a crystallinity of 42.26±1.35%. The second type of LLDPE used study was film molded from Dowlex™ 2056 resin with a melt index of 1.0 g/10 min, a density of 0.920 g/cm$^3$ and a crystallinity of 28.71±2.14%. The third type of LLDPE used was film molded from Dowlex™ 2036G resin with a melt index of 2.5 g/10 min, a density of 0.935 g/cm$^3$ and a crystallinity of 45.21±1.66%. Crystallinity of the films was calculated using differential scanning calorimetry (DSC). The samples were cut into squares of about 3 cm by about 3 cm.

BARD Peripheral Vascular OEM Products (Tempe, Ariz.) supplied the PET samples made from Style 6010 thin polyester tubular woven (uncrimped) specimens with a nominal diameter of 22 mm and wall thickness of 0.010"±0.001". All PET fabrics were woven without additional surface treatment. The resulting PET fabric had a density of 1.78 g/cm$^3$ and a crystallinity of 38.28±0.54%, as calculated by DSC. Samples were cut into squares of about 3 cm by about 3 cm. Xylenes showed the greatest degree of swelling, possibly due to the closeness of the solvent's Hildebrand solubility parameter.

Two systems were used to test swelling. The first system was an open-cup, consisting of a 50-mL beaker covered with a watch glass in a controlled-temperature oil bath. The second system was a 250-mL round-bottom flask fitted with a 24/40 standard taper ground glass joint and a serum stopper. The ground joint was fitted with a 100-mm West condenser capped with a rubber septum. The sealed round-bottom flask was lowered into a heated oil bath with a temperature probe. No differentiation is made between the two swelling methods. Both methods were used in experiments and yielded similar results.

Samples were weighed before submersion in solvent. After samples were allowed to swell for a desired amount of time, dried of surface solvent and weighed. Reported data are the average of the three samples±the standard deviation. When the averaged masses of the samples reached equilibrium, the temperature of the solvent was increases and the weighing procedure repeated until equilibrium was again reached. The temperature of the solvent was increased until the LLDPE film degraded.

The following equation was used to calculate the percent change in volume of the sample (dVNo %):

$$\frac{dV}{V_0} = \frac{W_t - W_0/\rho_{solvent}}{W_0/\rho_{polymer}}$$

where $W_t$ is the weight of the sample at time t, $W_0$ is the weight of the sample at time $t_0$, $\rho_{solvent}$ is the density of the solvent, and $\rho_{polymer}$ the density of the polymer.

Changes in crystallinity and tensile properties guided selection of the polymer host and swelling parameters to achieve the selected volumetric expansion without compromising the material's mechanical properties. The % $\chi_c$ was measured by a TA Instruments DSC 2920 in a dry nitrogen atmosphere per ASTM D3418-03. LLDPE samples were heated from 24° C. to 180° C. at a rate of 10° C./minute and held at equilibrium for one minute. PET samples were heated from 24° C. to 275° C. at a rate of 10° C./minute, and held at equilibrium for one minute. The heat of formation ($H_f$) was determined to be 288 J/g for 100% crystalline PE and 113 J/g for 100% crystalline PET. The % $\chi_c$ of the sample was calculated by dividing the $H_f$ of the sample by 288 J/g or 113 J/g based on base polymer and multiplying by 100. Sample control and treatment groups that were characterized, including LLDPE virgin film, PET virgin fabric, LLDPE and PET sham controls, and all LLDPE-T and PET-T samples.

Figure 3:
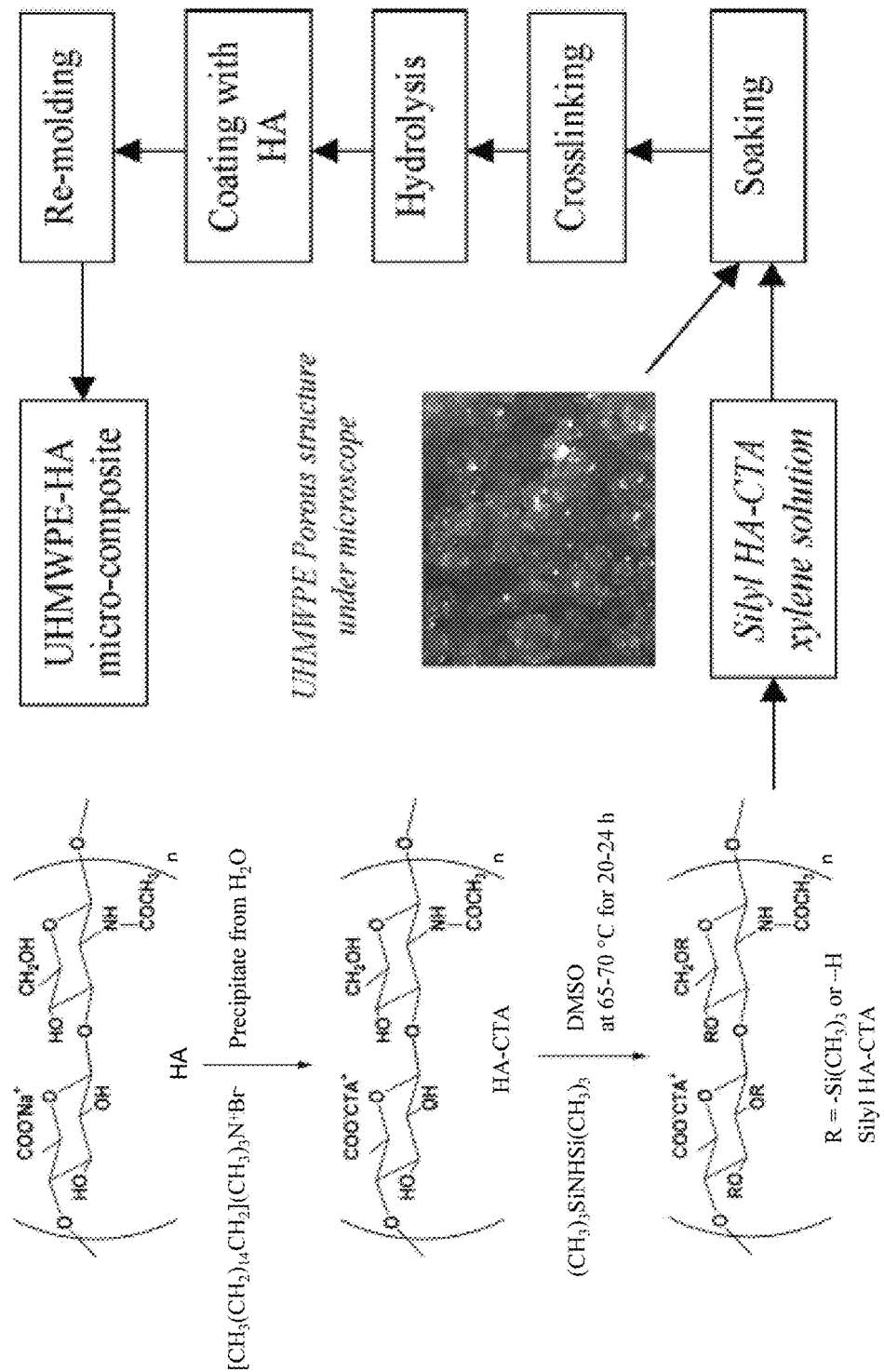
FIG. 3 represents a method used to make Biopoly®.
Figure 4:
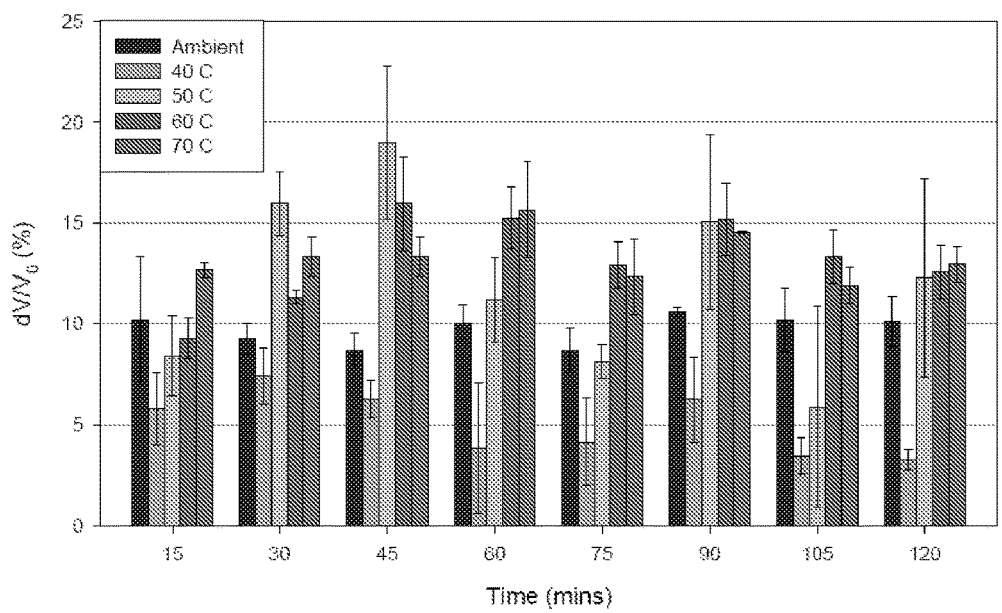
FIG. 4 shows the percentage volume change of commercial Dowlex™ 2344 LLDPE film in xylenes at various temperatures.
Figure 5:
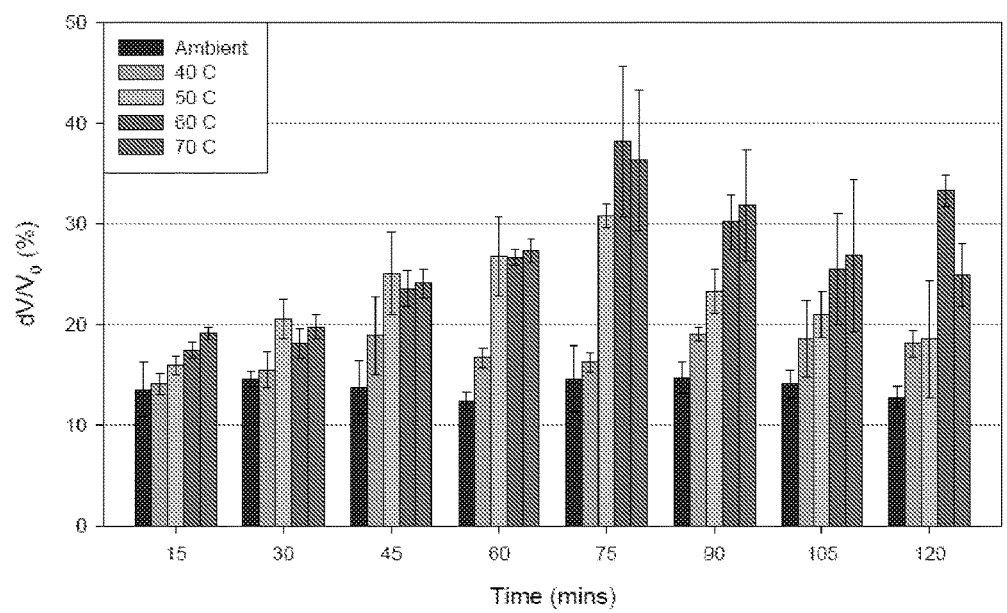
FIG. 5 shows the percentage volume change of commercial Dowlex™ 2056 LLDPE film in xylenes at various temperatures.
Figure 6:
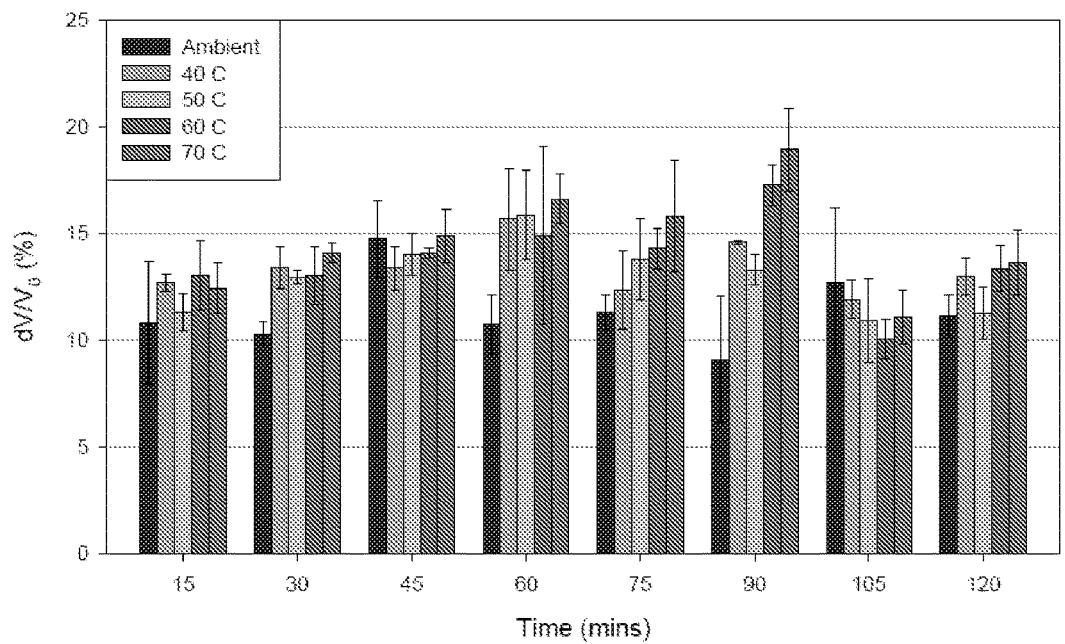
FIG. 6 shows the percentage volume change of commercial Dowlex™ 2036G LLDPE film in xylenes at various temperatures.

Representative data of the percent volume change (dVNo %) of the three commercial LLDPE films in xylenes versus time at different temperatures are shown in FIGS. 4, 5, and 6 for the Dowlex™ 2344, 2056, and 2036G, respectively. Data in these figures resulted from the open-cup swelling method except for the 70° C. data, which resulted from the round-bottom flask method.

Figure 7:
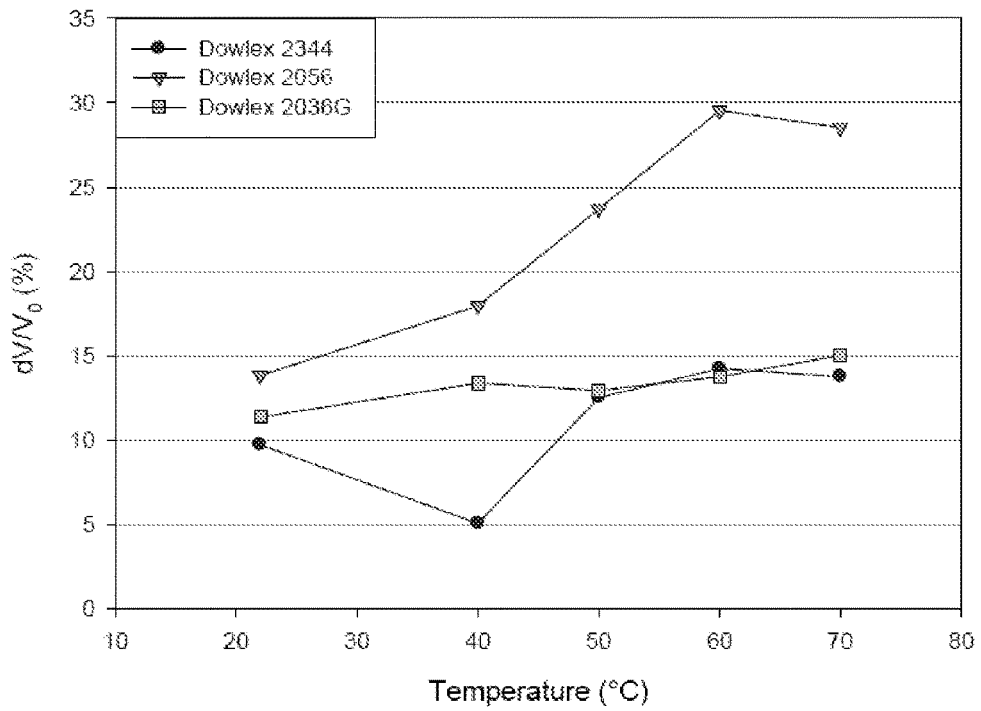
FIG. 7 shows the percentage volume change of commercial Dowlex™ 2036G LLDPE film in xylenes at various temperatures.
Figure 8:
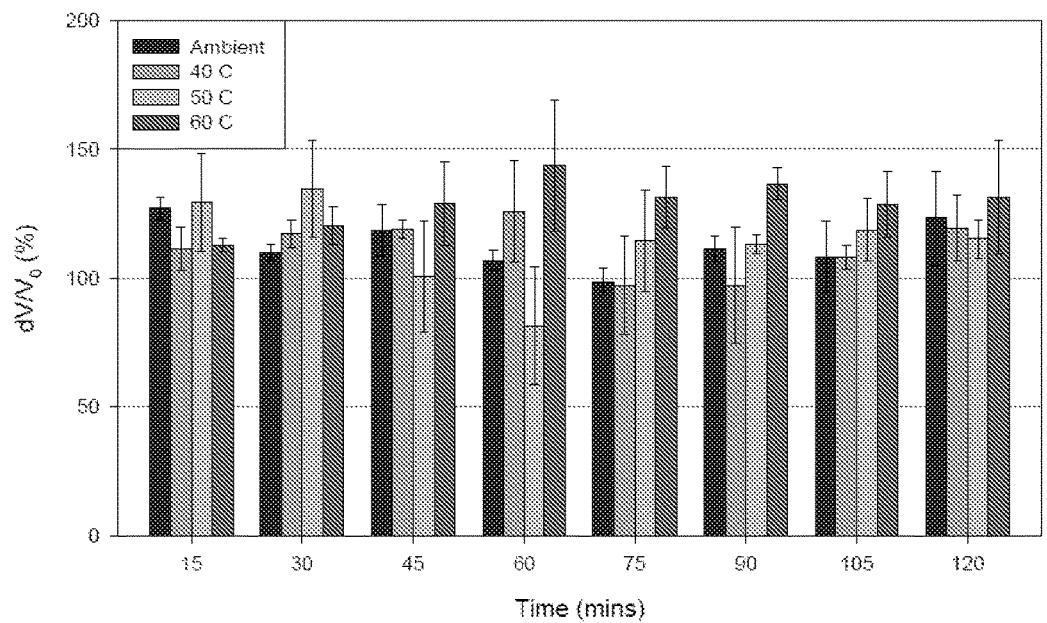
FIG. 8 shows the percentage volume change of commercial PET fabric in xylenes at various temperatures.

FIG. 7 represents the percentage volume change (dVNo %) of the Dowlex™ LLDPE films in xylenes versus temperature. Focusing on the degree of swelling of the LLDPE films in xylenes vs. temperature, there appears to be a non-linearity for Dowlex™ 2056 starting around 60° C. It is believed that the swelling to this point has taken place mainly in the amorphous regions of the film. Beyond this point, the crystalline regions prevent the film from swelling further prior to melting of the crystalline regions. The Dowlex™ 2036G continues to be linear due to its higher melt flow rate, preventing a rapid expansion of the material in the solvent. If only the amorphous regions of the LLDPE are swelled it would be expected that the lower crystallinity Dowlex™ 2056 material would swell to a greater extent. Representative data of the percent volume change (dVNo %) of the PET fabric in xylenes versus time at different temperatures are shown in FIG. 8. Data in this figure result from the open-cup swelling method. Temperature increases were halted at 60° C. due to satisfactory swelling at lower temperatures and no significant differences in swelling with previous temperature increases. Also, temperatures greater than 60° C. may lead to HA degradation.

Figure 9:
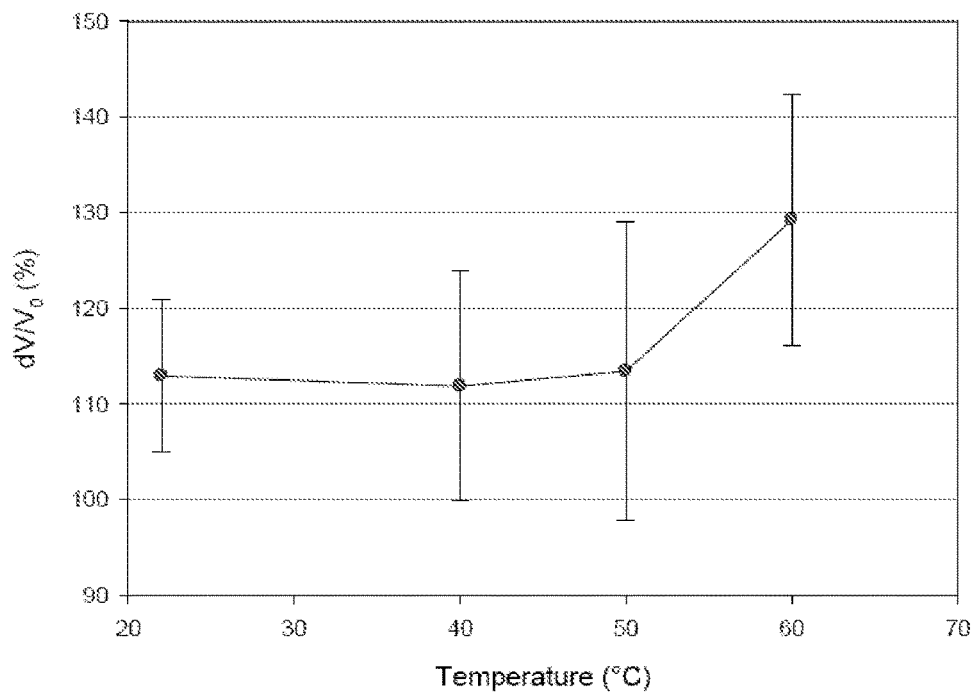
FIG. 9 shows the percentage volume change of PET fabric in xylenes at various temperatures.

FIG. 9 represents the percentage volume change (dVNo %) of the PET fabric in xylenes versus temperature. The apparent nonlinearity for the PET fabric starting around 60° C. is statistically insignificant at different temperatures. Even though the solubility parameters for xylenes and PET do not predict significant swelling, PET fabric fibers may swell in xylenes at an increased temperature. Lower temperatures do not influence the amount of swelling. The weave of the fabric may wick solvent, occupying the voids between fibers and yarns. At elevated temperatures, in contrast, the fibers swell with the solvents, thus increasing the amount of swelling. At 50° C. and below wicking into the fabric open voids is likely. At 60° C. and above, wicking and swelling both occur, leading to an IPN at fiber level and a microcomposite at fabric level.

Dowlex™ 2344 and 2056 LLDPE samples reached 90% of the equilibrium swelling value at 50° C. in approximately 1 hour. Dowlex™ 2036G reached 100% of its equilibrium value within 1 hour. These values indicate the need of active solvent transport. The PET fabric reached 100% of its equilibrium swelling value at each temperature within 15 minutes of placement into solvent bath. Extended exposure to solvents did not increase the volumetric expansion of the fabric, suggesting that the solvent was only penetration voids between fibers and yarns instead of swelling the PET fibers.

Figure 10:
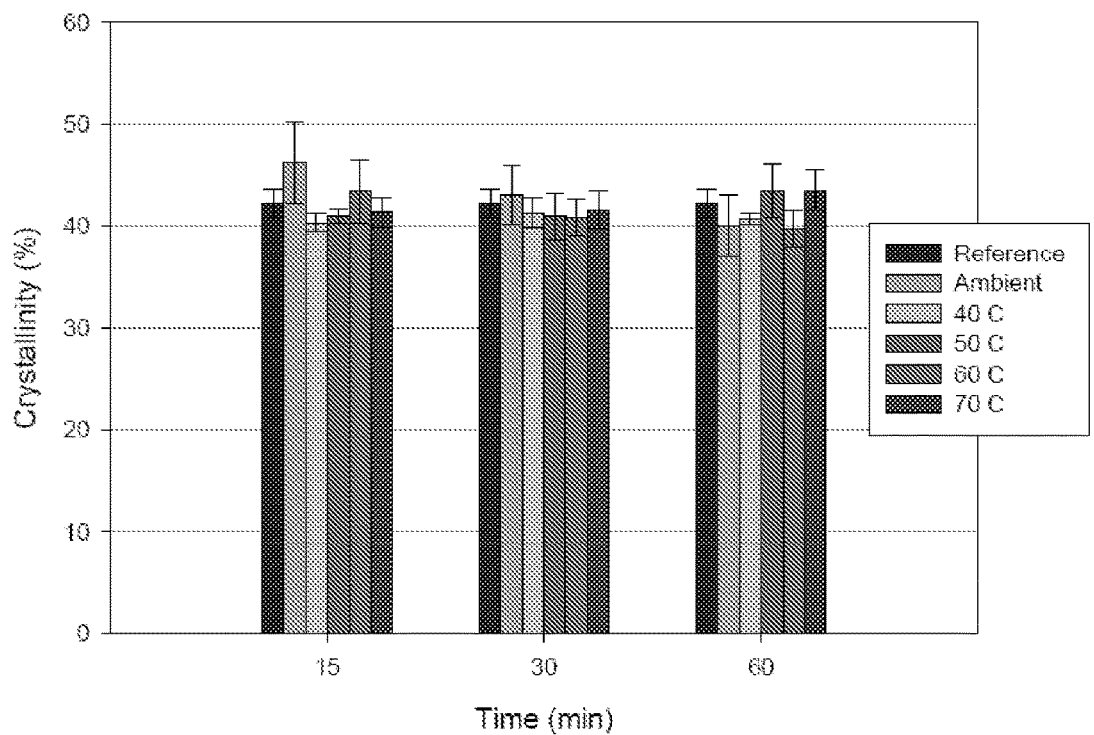
FIG. 10 shows the crystallinity of commercial Dowlex™ 2344 LLDPE following swelling at different temperatures.
Figure 11:
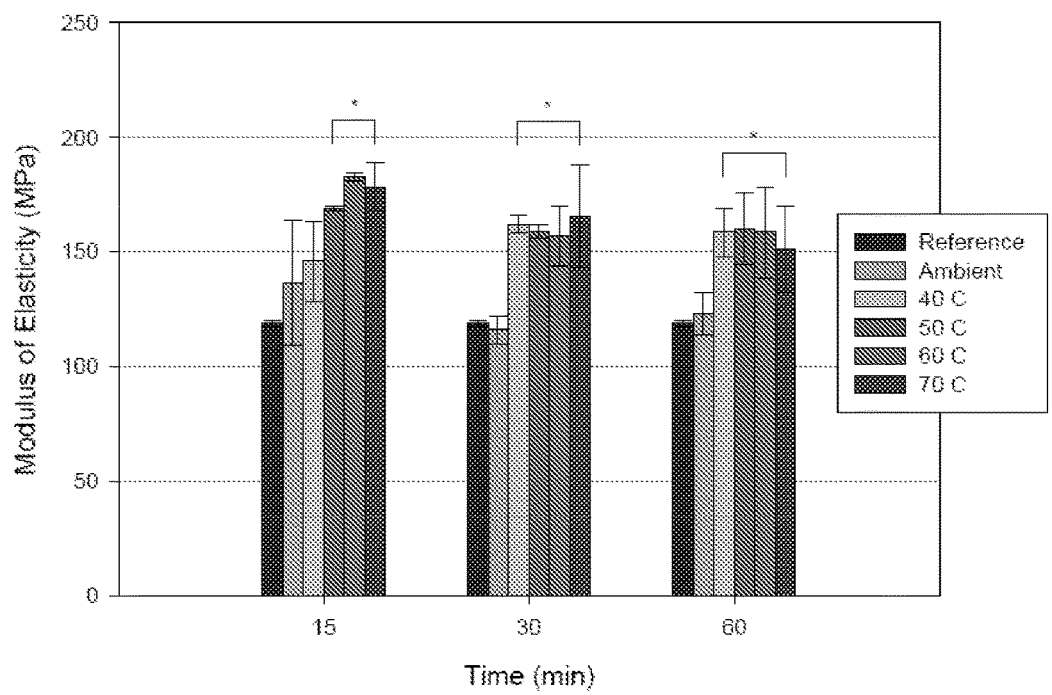
FIG. 11 shows the modulus of elasticity of commercial Dowlex™ 2344 LLDPE following swelling at different temperatures.
Figure 12:
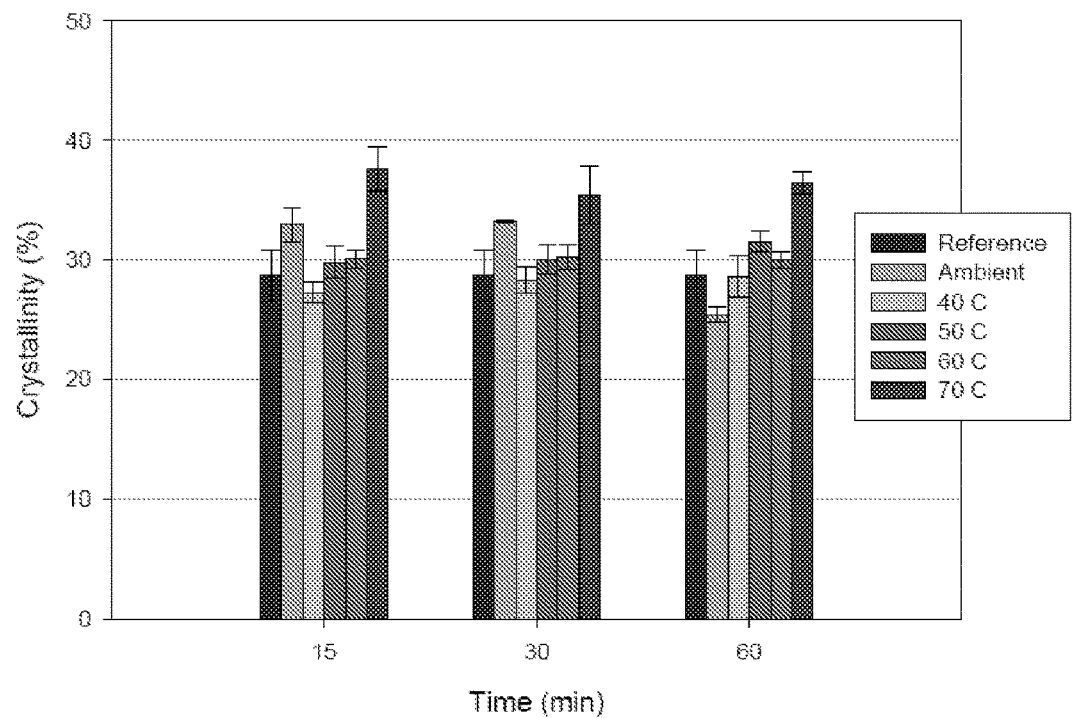
FIG. 12 shows the crystallinity of commercial Dowlex™ 2056 LLDPE following swelling at different temperatures.
Figure 13:
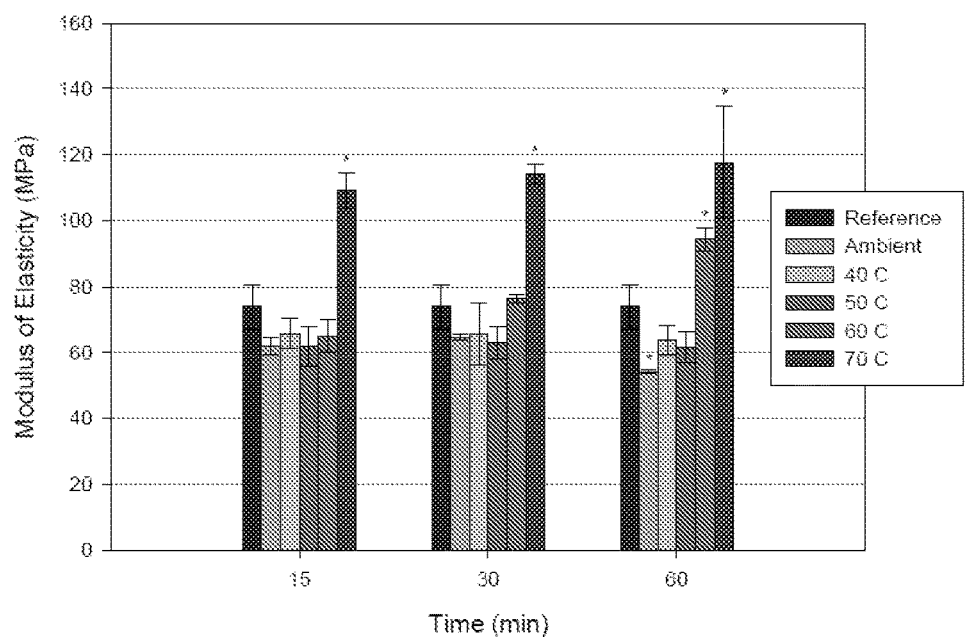
FIG. 13 shows the modulus of elasticity of commercial Dowlex™ 2056 LLDPE following swelling at different temperatures.
Figure 14:
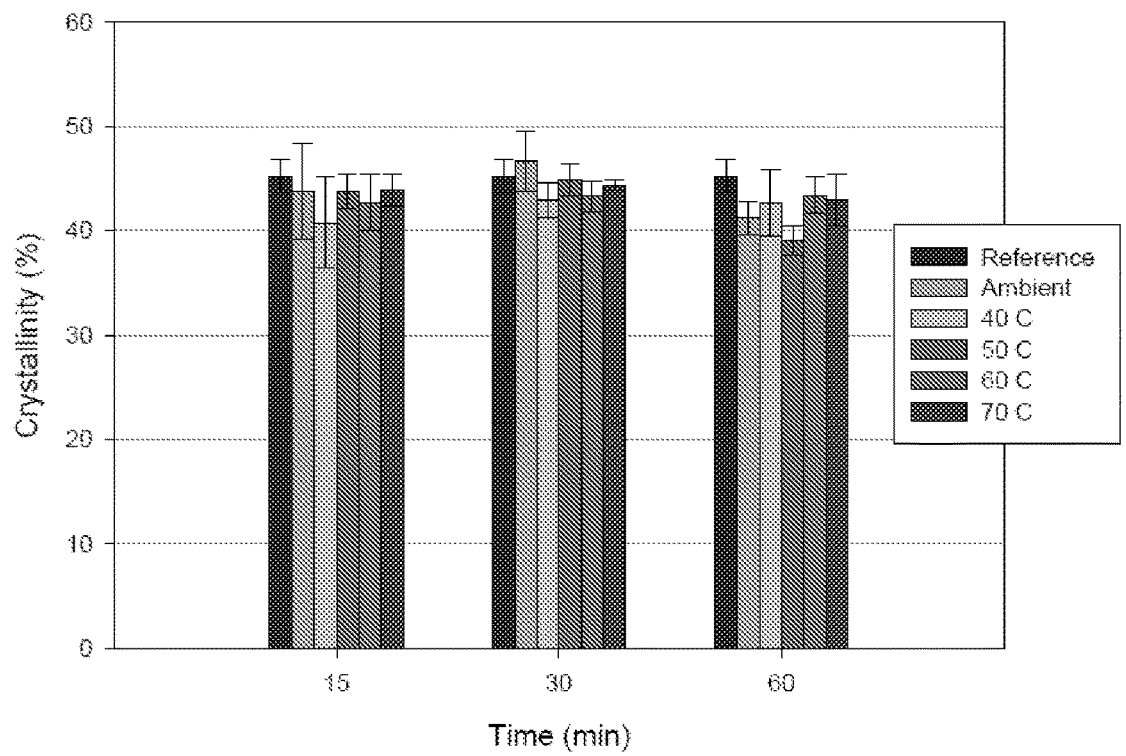
FIG. 14 shows the crystallinity of commercial Dowlex™ 2036G LLDPE following swelling at different temperatures.

With more swelling with use of xylenes and elevated temperatures, crystallinity of the Dowlex™ 2056 was increased while the Dowlex™ 2344 and 2036G were much more thermally stable and did not increase crystallinity. This increase in crystallinity subsequently caused an increase in the modulus and yield strength of the Dowlex™ 2056 as well. Crystallinity increased (FIGS. 10, 12, and 14) and the tensile increased (FIGS. 11, 13, and 15) for Dowlex™ 2344, 2056, and 2036G, respectively.

Figure 16:
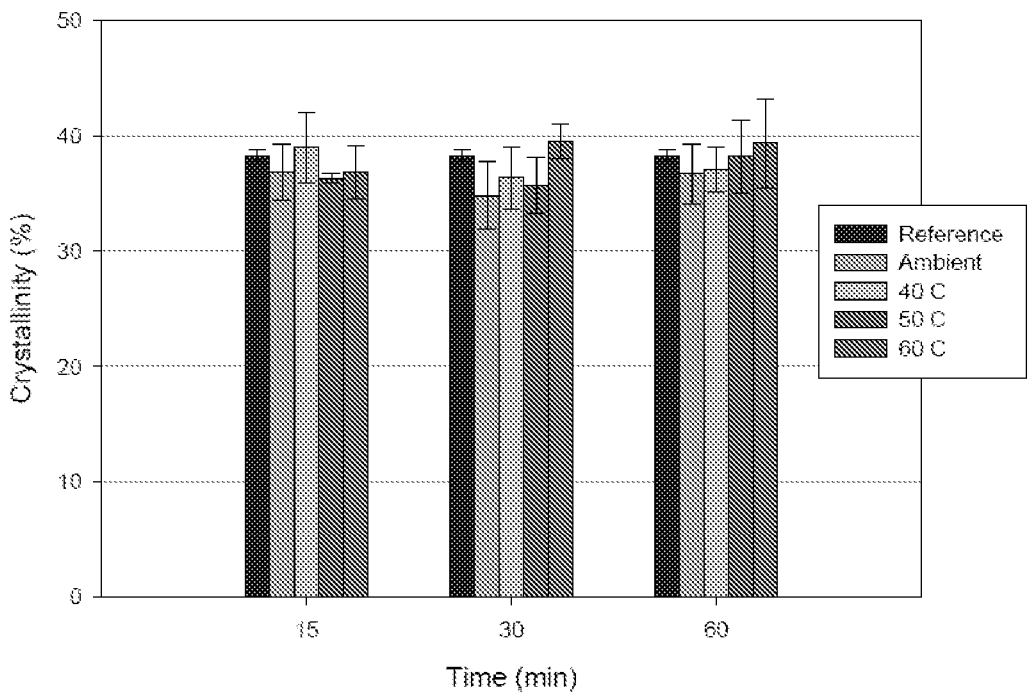
FIG. 16 shows the crystallinity of commercial Dowlex™ 2036G LLDPE following swelling at different temperatures.

Since the solvents only penetrated voids within the PET fabric and did not swell the fibers, drying the PET fabrics removed solvents and returned the fabric to its original state. The crystalline structure remained unchanged during soaking (FIG. 16).

Xylenes provided the greatest degree of swelling in the Dowlex™ 2056 film. The temperature of swelling had the largest increase in degree of swelling for the Dowlex™ 2056 film and provided inconsistent swelling in the other films. For this reason, the Dowlex™ 2056 film was chosen as the LLDPE polymer host in the examples below. The crystallinity changes were largest at the higher temperatures, increasing tensile properties, and particularly tensile modulus. This increases the bending stiffness, which may not be desirable in heart valve leaflets. The percent volume change (dVNo %) at 50° C. was equivalent to that at 60° C. at 45 and 60 minutes without the associated increase in crystallinity and modulus of elasticity. For this reason, 50° C. was chosen for the swelling temperature for the LLDPE-HA microcomposite synthesis in the example below.

Example 2: Synthesis of Silyl-HA-CTA

To produce cetyltrimethylammonium silylhyaluronate (silyl HA-CTA), dimethyl sulfoxide (DMSO) was added to cetyltrimethylammonium hyaluronate (HA-CTA) under dry $N_2$ flow. The solution was stirred at 50° C. until the HA-CTA was completely dissolved. The HA-CTA and DMSO solution temperature was increased to 75° C., and hexamethyldisilazane (HMDS) was added under dry $N_2$ flow. The reaction was carried out for at least about 36 hours. Once stirring ceased, the resultant biphasic solution was separated. The top layer was saved and vacuum dried at 50° C. until no change in weight was observed. The bottom layer was discarded. The dry powder, characterized to be silyl HA-CTA, was washed five times with xylenes. The washed silyl HA-CTA was dried again under vacuum at 50° C. vacuum until no change in weight was observed.

Example 3: Synthesis Composites from LLDPE, PET, and ePTFE

All treated LLDPE BioPoly™ (LLDPE-T) samples were fabricated from blown LLDPE film. All treated PET BioPoly™ (PET-T) samples were fabricated from stretch knit PET, as described in Example 1. The synthesis parameters of LLDPE-T and PET-T samples are shown in Table 1.

TABLE 1

Table of synthesis paramaters

| Sample | Conc. of silyl HA | Conc. of Cross-linker | Hydro-lysis | Dip with HA? | Conc. Of HA? |
|---|---|---|---|---|---|
| LLDPE-T | Silyl HA-CTA 0.5-50 mg/mL 1.5-150 mg/mL 2.5-250 mg/mL | Desmodur ™ 2% | After Treatment | No | n.a |
| LLDPE-T-D | Silyl HA-CTA 0.5-50 mg/mL 1.5-150 mg/mL 2.5-250 mg/mL | Desmodur ™ 2% | Before HA Dip | Yes | 1% |
| PET-T | Silyl HA-CTA 0.5-50 mg/mL 1.5-150 mg/mL 2.5-250 mg/mL | Desmodur ™ 2% | After Treatment | No | n.a |
| PET-T-D | Silyl HA-CTA 0.5-50 mg/mL 1.5-150 mg/mL 2.5-250 mg/mL | Desmodur ™ 2% | Before HA Dip | Yes | 1% |

* n.a. = not applicable

Figure 15:
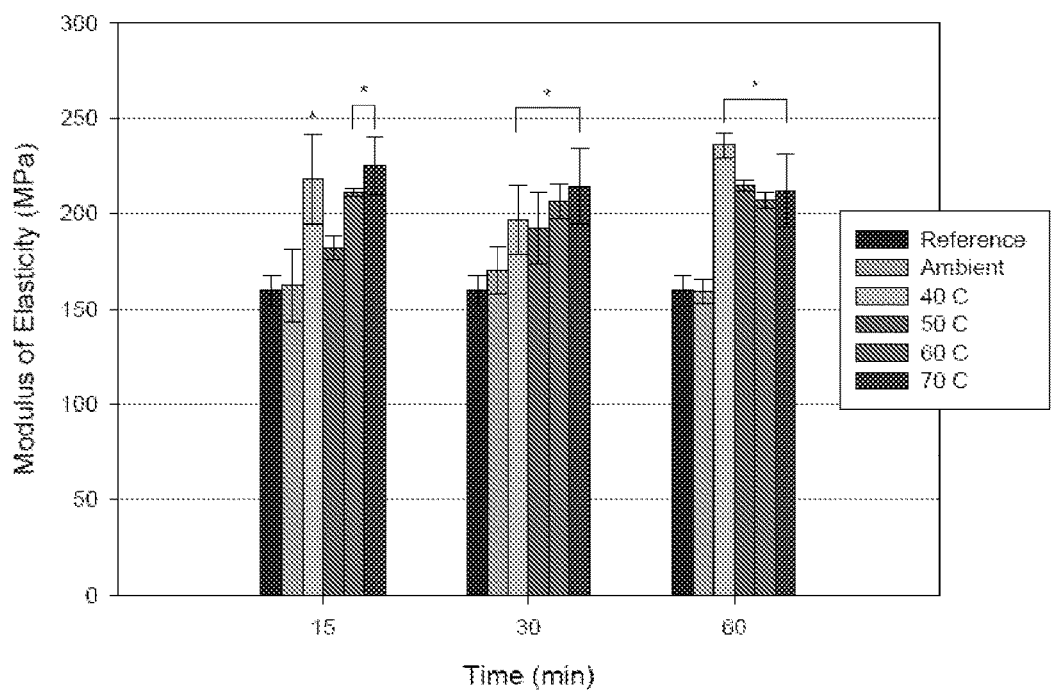
FIG. 15 shows the modulus of elasticity of commercial Dowlex™ 2036G LLDPE following swelling at different temperatures.

The HA treatment processes for LLDPE-T and PET-T differed due to the swelling kinetics (FIG. 15). LLDPE film and PET fabric were soaked in xylenes for 12 hours and vacuum dried another 12 hours. The LLDPE films were then swelled at 50° C. in a silyl-HA-CTA xylenes solution with a varying silyl-HA concentration, ranging from 0.5 to 2.5% (w/v) (to achieve a range of XL HA final bulk weight in the film) for 60 minutes, saturating the entire film sample. The treated LLDPE films were vacuum dried at 50° C. for 3 hours. Following the 12-hour xylenes wash and dry cycle, the PET samples were then soaked in a silyl-HA-CTA xylenes solution with a varying silyl-HA concentration, ranging from 0.5 to 2.5% (w/v), at ambient temperature for 15 minutes, saturating the entire fabric sample. The treated PET fabric samples were vacuum dried at 50° C. for 3 hours. The treated LLDPE films and PET fabric were hydrolyzed in by the same procedure. Following hydrolysis, LLDPE and PET samples requiring a final HA dip were dipped in a 1% (w/v) aqueous HA solution; the samples were submerged for several minutes to create an HA film on the surface. The dip-coated sample was vacuum dried at 50° C. The LLDPE and PET hydrolyzed, treated samples were dipped in a 2% (v/v) poly(hexamethylene diisocyanate) xylenes solution and vacuum dried for 3 hours at 50° C., washed in acetone for 15 minutes, and vacuum dried at room temperature.

The treated LLDPE films were then swelled at 50° C. in a 2% (v/v) poly(hexamethylene diisocyanate) xylenes solution for 60 minutes, and the crosslinker was cured in a vacuum oven at 50° C. for 3 hours. The treated PET fabric samples were then soaked in a 2% (v/v) poly(hexamethylene diisocyanate) xylenes solution for 15 minutes at ambient temperature, and the crosslinker was cured in a vacuum oven at 50° C. for 3 hours. The treated samples were then washed with acetone to remove excess poly(hexamethylene diisocyanate) and vacuum dried at room temperature.

Hydrolysis was conducted in 45° C. 0.2 M NaCl solution (1:1 $H_2O$/ethanol) in an ultrasonic bath for 60 minutes. After one hour, the process was repeated twice more with fresh ethanolic sodium chloride, and once with aqueous sodium chloride. The treated film and fabric samples were soaked in a 3:2 $H_2O$ ethanol (v/v) for two hours, followed by sonication in water for 30 minutes. The hydrolyzed treated samples were removed from the bath, washed with water, soaked in acetone for 1 hour, dried under vacuum at 50° C. A summary of the hydrolysis procedure is shown in Table 2.

TABLE 2

Hydrolysis procedure for silyl HA-CTA

| Step | Time (hours) | Bath Composition | Sonication Time (hours) |
|---|---|---|---|
| 1 | 1 | 0.2M NaCl (1:1 $H_2O$/ethanol) | 1 |
| 2 | 1 | 0.2M NaCl (1:1 $H_2O$/ethanol) | 1 |
| 3 | 1 | 0.2M NaCl (1:1 $H_2O$/ethanol) | 1 |
| 4 | 1 | 0.2M NaCl aqueous | 1 |
| 5 | 2 | $H_2O$/ethanol (3:2) | n.a. |
| 6 | 0.5 | Water | 0.5 |
| 7 | 1 | Acetone | n.a |
| Total time | 7.5 | | |

* n.a. = not applicable

% $\chi_c$

The % $\chi_c$ was measured with a TA Instruments DSC 2920 under dry $N_2$ per ASTM D3418-03. Samples were heated from 24° C. to 180° C. at a rate of 10° C./minute, and held at equilibrium for one minute. The $H_f$ was determined to be 288 J/g for 100% crystalline PE, and 113 J/g for 100% crystalline PET. The % $\chi_c$ of the sample was calculated by dividing the $H_f$ of the sample by 288 J/g or 113 J/g based on base polymer and multiplying by 100. The sample control and treatment groups that were characterized include LLDPE virgin film, PET virgin fabric, LLDPE and PET sham controls, and all LLDPE-T|PET-T samples. All reported average values and standard deviation for % $\chi_c$ were calculated from a sample size of three per group.

The degradation temperatures ($T_d$) and composition of the samples were determined using a TA Instruments thermal gravimetric analyzer (TGA) 2950 at a heating rate of 10° C./minute in helium. Masses of individual specimens ranged from 5-15 mg. Sample control and treatment groups that were characterized: LLDPE virgin film, PET virgin fabric, LLDPE and PET sham controls, and all LLDPE-T/PET-T samples. All reported average values and standard deviations for compositions and Td were calculated from a sample size of three per group.

For tensile testing, ASTM D882-10 standard tensile specimens of film thickness were stamped out of treated LLDPE samples. An electromechanical Tinius Olsen UTM axial test system (Horsham, Pa.) was used in conjunction with Test Navigator software from Tinius Olsen to perform all tensile tests; a uniaxial (tension/compression) 1000 N load cell (Model HIK-S) was used. Five tensile bars were stamped out of each sample. Two tensile bars were used for the modulus test for each treatment group, while three tensile bars were used for the measurement of yield strength, tensile strength and elongation to failure for each treatment group. Samples were pulled at a crosshead speed of 500 mm/minute. These strain rates follow the ASTM standard, which states that the time to failure of a polymeric sample must fall within a certain time limit. This can be adjusted for different materials by changing the strain rate. Elongation data was calculated from crosshead data. The change in gage length was divided by the original gage length of the sample, which is specified in the standard.

For bending stiffness, the ASTM D1388-08 testing standard was used to determine the bending modulus of the PET samples. Bending specimens of fabric thickness were stamped out of treated PET samples and a Shirley Stiffness Tester (Model M003B) was used. One sample of each treatment group was used to measure bending stiffness at both ends, on opposite faces, for a total of four measurements per sample group. The samples were conditioned to the standard atmosphere for at least 24 hours, or until the mass of the specimen did not change by more than 0.25% in 2-hour intervals. All samples were tested (tensile, bending) in a hydrated condition. Tensile was also tested dry to determine any changes in tensile properties due to hydration which there were none. Specimens were slid at a uniform rate until the bending length is determined. This was used to calculate the flexural rigidity G (mg/cm):

$$G = 0.10 MC^3$$

where M is the mass per unit area (g/m$^2$), and C is the bending length (cm).

The bending modulus K (kg/cm$^2$) is given by the following formula:

$$K = \frac{12G * 10^{-6}}{t^3}$$

where G is the flexural rigidity (mg/cm), and t is the fabric thickness (cm).

Statistical analysis was performed using SigmaStat software (Systat Software Inc.; Richmond, Calif.). A single-factor ANOVA test with a 95% confidence interval was performed. The Holm-Sidak method was used for multiple comparisons when sample population standard deviations and population sample sizes were similar. Population means, which had unequal variances, were analyzed using non-paired t-tests ($\alpha=0.5$). Average values and standard deviation for all treatment group populations were calculated. Crosslinked HA weight percentages (where applicable) for all LLDPE and PET composites are summarized in Tables 3 and 4.

TABLE 3

Crosslinked hyaluronic acid composition of treated LLDPE samples

| Treatment Group | Bulk Weight % XL HA | Surface Weight % XL HA |
| --- | --- | --- |
| LLDPE-T-0.5 | 0.51 | n.a.* |
| LLDPE-T-1.5 | 1.32 | n.a |

TABLE 3-continued

Crosslinked hyaluronic acid composition of treated LLDPE samples

| Treatment Group | Bulk Weight % XL HA | Surface Weight % XL HA |
| --- | --- | --- |
| LLDPE-T-2.5 | 1.00 | n.a |
| LLDPE-T-0.5-D | 0.54 | 0.035 |
| LLDPE-T-1.5-D | 1.47 | 1.146 |
| LLDPE-T-2.5-D | 1.05 | 0.043 |

*not applicable

TABLE 4

Crosslinked hyaluronic acid composition of treated PET samples

| Treatment Group | Bulk Weight % XL HA | Surface Weight % XL HA |
| --- | --- | --- |
| PET-T-0.5 | 0.24 | n.a.* |
| PET-T-1.5 | 0.97 | n.a |
| PET-T-2.5 | 1.23 | n.a |
| PET-T-0.5-D | 1.26 | 1.02 |
| PET-T-1.5-D | 2.00 | 1.02 |
| PET-T-2.5-D | 3.51 | 2.28 |

*not applicable

The reported values were determined from weight loss/gain calculations measured throughout the treatment processes and confirmed using TGA. PET samples comprised of high weight percentages of crosslinked HA exhibited an increased bending stiffness when dry. This effect, however, was removed once the sample was placed in solution, allowing the HA to swell and become lubricious.

The percent crystallinity of treatment groups LLDPE-T and PET-T versus controls are listed in Tables 5 and 6.

TABLE 5

Crystallinity of LLDPE controls and HA-treated samples (average ± standard deviation)

| Treatment Group | % X$_c$ |
| --- | --- |
| LLDPE-Ref | 28.14 ± 2.36 |
| LLDPE-T-0.5 | 32.97 ± 1.07 |
| LLDPE-T-0.5-Dip | 31.54 ± 1.88 |
| LLDPE-T-1.5 | 30.13 ± 1.88 |
| LLDPE-T-1.5-Dip | 31.74 ± 3.01 |
| LLDPE-T-2.5 | 32.66 ± 2.31 |
| LLDPE-T-2.5-Dip | 31.86 ± 1.59 |

TABLE 6

Crystallinity of PET controls and HA-treated samples (average ± standard deviation)

| Treatment Group | % X$_c$ |
| --- | --- |
| PET-Ref | 38.28 ± 0.54 |
| PET-T-0.5 | 38.98 ± 3.09 |
| PET-T-0.5-Dip | 36.28 ± 0.42 |
| PET-T-1.5 | 34.30 ± 0.13 |
| PET-T-1.5-Dip | 33.51 ± 3.91 |
| PET-T-2.5 | 39.44 ± 1.51 |
| PET-T-2.5-Dip | 39.36 ± 3.85 |

The crystallinity of the LLDPE film was not significantly altered during the treatment compared to the reference. The thermal processing of LLDPE film was maintained by the selected swelling parameters. The lack of swelling of the individual fibers of PET within the fabric reduced changes in crystallinity for the fabric. Since the silyl-HA-CTA solution only penetrated voids within the structure, drying the PET samples after swelling removed trace solvents. Thus, the crystalline structure remained generally unchanged during the swelling process.

Figure 17:
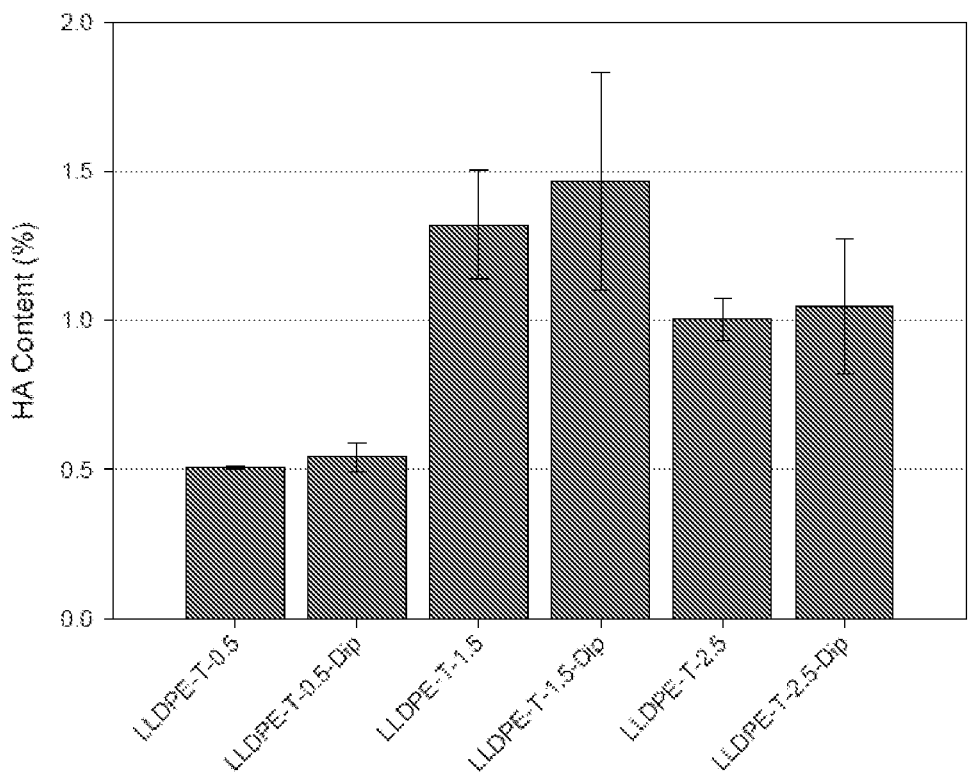
FIG. 17 shows the HA content (by weight %) for treated LLDPE samples.
Figure 18:
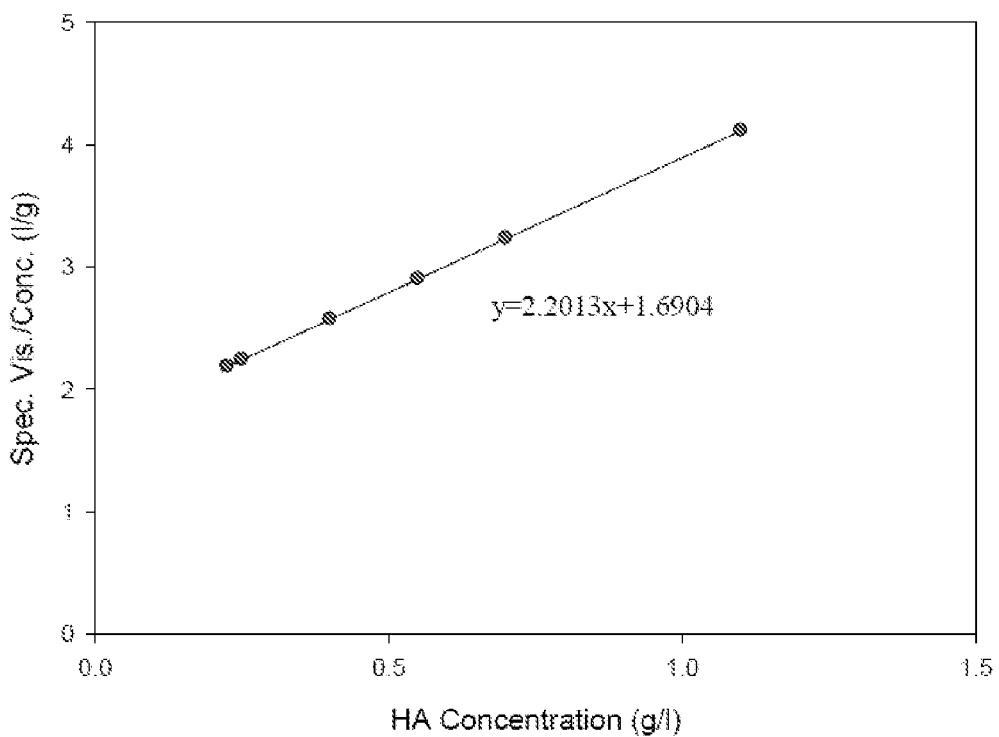
FIG. 18 shows the viscosity of HA solution.
Figure 19:
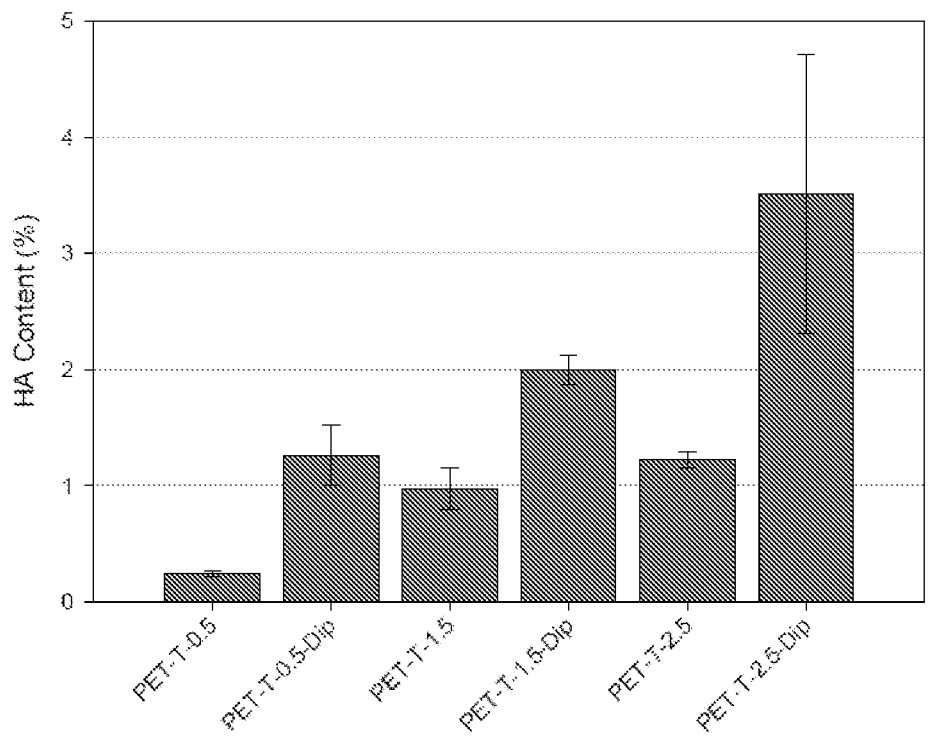
FIG. 19 shows the HA Content (by weight %) for treated PET samples.
Figure 20:
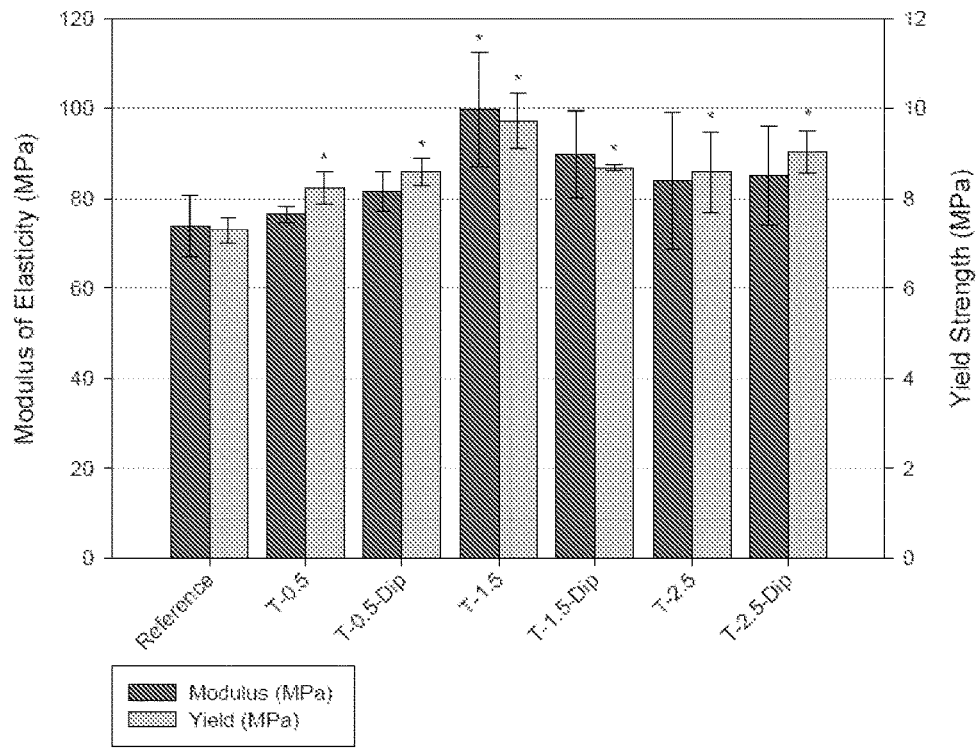
FIG. 20 shows the modulus of elasticity and yield strength of reference LLDPE film and treated LLDPE samples using treatment parameters listed in Table 1.

Multiple microcomposites with differing quantities of HA were successfully synthesized with a range from 0.5 to 1.5% HA for LLDPE samples (FIG. 17) and from 0.25 to 3.5% HA for PET (FIG. 19). An increase in HA concentration was seen from LLDPE-T-0.5 to LLDPE-T-1.5, due to the increased swelling solution concentration. This increase was not observed when increasing from LLDPE-T-1.5 to LLDPE-T-2.5. HA concentration in the microcomposite decreased by ~33%. With the higher concentration of silyl-HA-CTA in xylenes during swelling, specific viscosity increased linearly (FIG. 18) and permitted diffusion only into the outer polymer structure. In other words, higher HA concentration increased solution viscosity, reducing polymer swelling because of limited infusion of the solution into the LLDPE.

The incorporated HA was concentrated at the surface, potentially providing superior hemocompatibility qualities in that region. Additional post-treatment dip coating of HA did not significantly increase the samples' HA concentrations. Samples with the highest HA content based on the non-dipped samples may gain the highest amount of HA through a successful surface dip of HA. With a higher bulk concentration of HA, the additional dip would have more attached HA to link to.

The dipped samples examined were removed from the aqueous HA solution and hung horizontally in a vacuum oven. Droplets of the HA solution collected at the bottoms the film and dripped off, consequently preventing a uniform application of HA to the surface. Alternatively, the film samples are left in a Petri dish of the aqueous HA solution placed in a vacuum oven at 50° C. until the water evaporates, leaving a uniform coating of HA. Other methods of application include spin-coating and spray-coating the HA solution onto the microcomposite samples.

Expected increases in HA concentration were seen with increasing concentration of the swelling solution. The increased viscosity of the solution, which affected the LLDPE samples, was not seen in the PET samples due to the fact that they are not swelling in the solvent, but rather are wicking the solution into the open weave of the fabric. Unlike the LLDPE samples, post-treatment dip coating significantly increased the HA concentration in the PET samples. Dip coating fully penetrated the fabric structure and allowed easy of control uniformity. Therefore, the additional HA applied is not concentrated only at the surface, as in the LLDPE samples.

Figure 21:
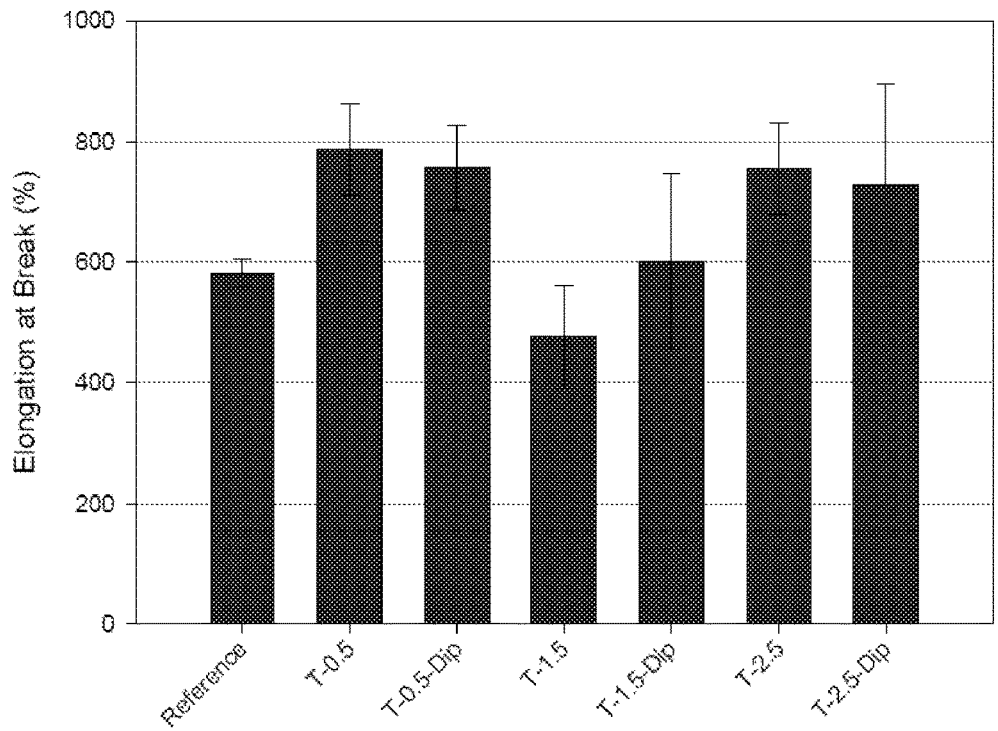
FIG. 21 shows the elongation to failure of reference LLDPE film and treated LLDPE samples using treatment parameters listed in Table 1.
Figure 22:
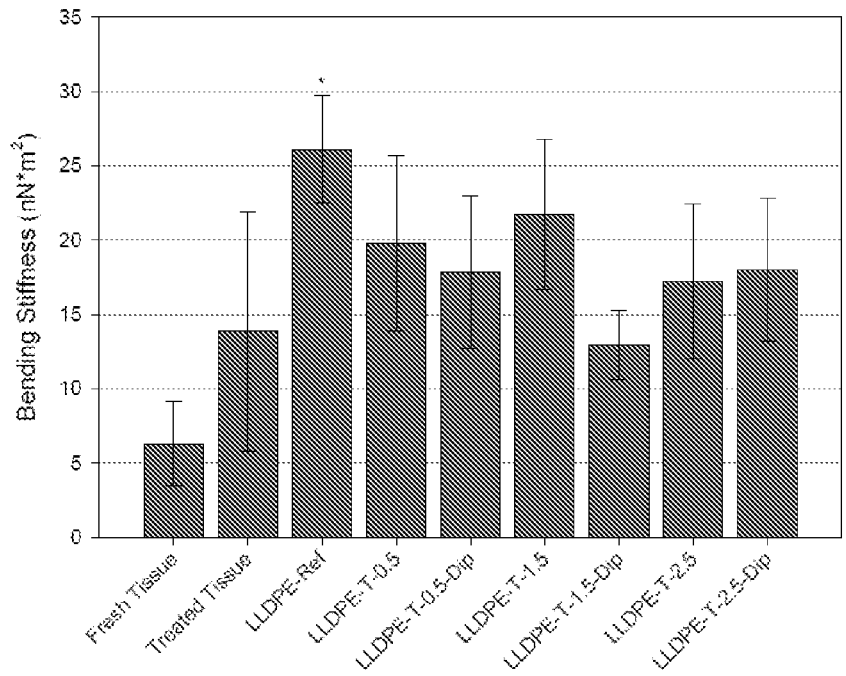
FIG. 22 shows the bending stiffness values for reference tissue and all treated and untreated LLDPE samples using treatment parameters listed in Table 1.

Samples were pulled at a strain rate of 500 mm/minute (FIGS. 21 and 22, and Table 7). Percent elongation values were calculated from crosshead displacement. Small increases in yield strength were observed among all treatment groups did not warrant concern for cardiovascular applications. The modulus is the property of most concern with the LLDPE film. Only the T-1.5 treatment group had a significantly (p≤0.05) higher modulus (99.71 MPa) compared to Reference film (73.82 MPa). Other sample groups did not vary significantly from each other. These small increases are associated with the small, but not significant increases in crystallinity (Table 5).

Elongation to failure did not significantly change in the treated LLDPE films compared to reference films. The variation in the elongation was increased with the treatment process. All films still exhibited elongations to failure far beyond that needed for satisfactory in vivo performance, and showed no signs of embrittlement due to the treatment. Table 7 summarizes tensile data and % $\chi_c$ for LLDPE reference film and treated LLDPE samples.

TABLE 7

Mechanical properties and % $X_c$ of control and treated LLDPE samples (average ± standard deviation)

| | Modulus (MPA) | Yield (MPA) | Elongation to Failure (%) | % $X_c$ |
|---|---|---|---|---|
| Reference | 73.82 ± 6.83 | 7.29 ± 0.29 | 582 ± 23 | 28.14 ± 2.36 |
| T-0.5 | 76.49 ± 1.86 | 8.23 ± 0.35* | 787 ± 76 | 32.97 ± 1.07 |
| T-0.5 | 81.56 ± 4.44 | 8.61 ± 0.30* | 757 ± 70 | 31.54 ± 1.12 |
| T-1.5 | 99.71 ± 12.62* | 9.74 ± 0.61* | 476 ± 85 | 30.13 ± 1.88 |
| T-1.5-Dip | 89.92 ± 9.64 | 8.70 ± 0.08* | 601 ± 147 | 31.74 ± 3.01 |
| T-2.5 | 84.05 ± 15.30 | 8.59 ± 0.90* | 755 ± 75 | 32.66 ± 2.31 |
| T-2.5-Dip | 85.12 ± 11.01 | 9.04 ± 0.47* | 728 ± 168 | 31.86 ± 1.59 |

*represent a significant difference (p ≤ 0.05) compared to the reference film

Figure 23:
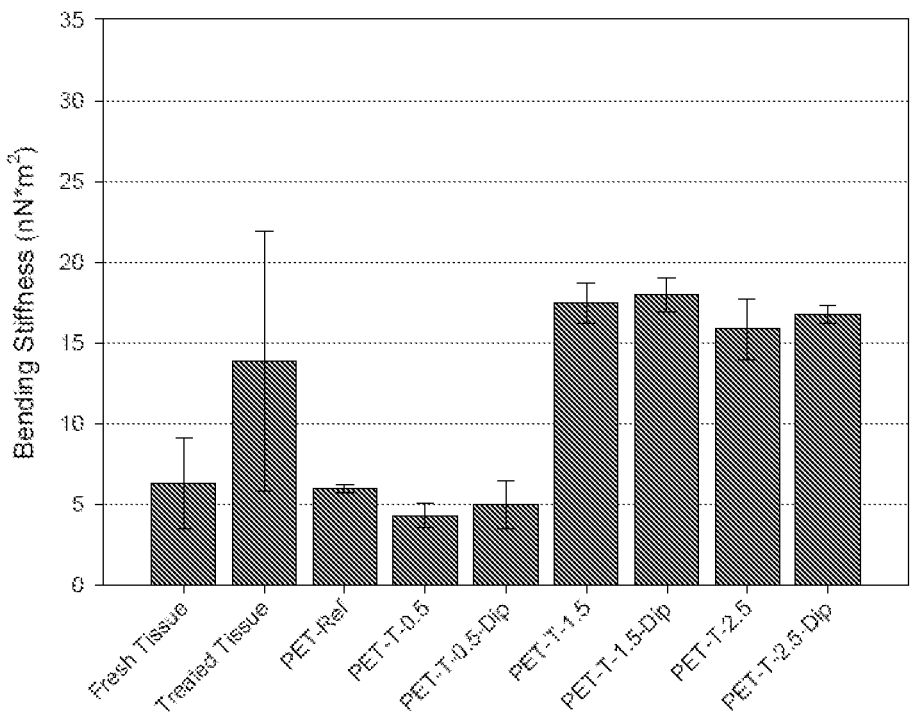
FIG. 23 shows the bending stiffness values for reference tissue and all treated and untreated PET samples using treatment parameters listed in Table 1.

Bending stiffness is the principal property of concern for heart valve applications. The resulting bending stiffness of LLDPE and PET treatment groups versus controls are shown in FIGS. 22 and 23. The comparison is also made to stiffness values for native valve leaflets and glutaraldehyde-fixed xenograft leaflets to confirm that the treated specimens were within physiological ranges. Bending stiffness values were calculated from the bending length and known densities. The bending stiffnesses of the LLDPE samples were within the physiological range of the native tissue and glutaraldehyde-fixed xenograft tissue with the exception of the untreated reference film. No significant differences were seen between the treatment groups, indicating that HA incorporation into the host polymer would have acceptable bending properties with any of the tested HA concentrations for a heart valve application. The bending stiffness of glutaraldehyde-treated tissue can be up to four times greater than fresh tissue. This increased bending stiffness of the treated tissue may ultimately lead to the observed leaflet tearing, calcification, and eventual failure from tissue anisotropy. With isotropic LLDPE, fatigue performance is satisfactory in general for this application and exceeds fatigue strength of polyurethane used in leaflets. Calcification of the material could be avoided with the HA treatment of the LLDPE. Moreover, composite materials may be independently tuned to both bending stiffness and fatigue properties. The polymeric base is not restricted to LLDPE, as used in this example.

The increased bending stiffness of the treated PET fabric containing 1.0% HA is likely correlated to HA linking to the fibers. Expansion of HA with exposure to an aqueous solution helps reduce bending stiffness and alleviate fiber fatigue and frictional stress between fibers. Native valves must function such that the stresses generated within the material are low enough to prevent fatigue failure during the normal lifetime of a healthy valve. One of the factors reducing stresses is its extreme pliability. The microcomposites exhibit pliability that makes them a preferable material for leaflet replacements.

Example 4: Hemocompatibility of LLDPE-HA and PET-HA

When a foreign material comes into contact with blood, plasma proteins rapidly adsorb onto its surface, followed by platelet adhesion and activation. Platelet activation initiates coagulation, resulting in a clot. Generally, hydrophobic surfaces adsorb larger amounts of proteins than hydrophilic surfaces. Therefore, hydrophilic surfaces may increase hemocompatibility. Because, interactions of various blood components initiate at implantation, microcomposites should not cause protein adhesion, platelet aggregation, blood coagulation, or fibrin deposition. Hemocompatibilty may also be related to HA's bioactivity and ionic character.

Absorption and desorption of blood proteins on polymeric materials depend on the surface characteristics, such as hydrophilicity/hydrophobicity. Toluidine blue O (TBO) dye staining and surface contact angle measurements demonstrated presence of HA on the microcomposites. Compared to controls, contact angles of treated LLDPE microcomposites significantly decreased, and the degree of decrease was directly proportional to the HA surface density. The intensity of TBO within the PET samples shows a sharp contrast to the control PET representative of a gradient of HA content.

Static water contact angles were measured for the LLDPE samples produced in Example 3, using the sessile drop method with a Krüss DSA 10 goniometer (Krüss GmbH, Hamburg). Samples were conditioned in deionized water (diH$_2$O) for 24 hours before testing. At room temperature, a diH$_2$O drop with a known volume (3 μL) was automatically dosed onto the sample. The contact angles were determined with circle fitting profile after the video system imaged the H$_2$O drop. The time duration was about two seconds. Two different locations on each sample surface were tested in triplicate. The contact angle was recorded immediately after the droplet of fluid had been placed on the sample surface. Cast HA film, LLDPE-Ref, and all LLDPE-T samples, with and without final HA dip with several HA concentrations, were characterized. PET samples were not tested due to the morphology of the weave producing unreliable results.

Toluidine blue (TBO) was used to identify the integration of HA within the microcomposite. A 0.1% TBO solution with 8 M urea was added dropwise to the surface of samples. After 10 minutes, the TBO solution was rinsed away with H$_2$O, leaving behind bound TBO. Three samples from each treatment group were photographed, including PET-Ref and all PET-T samples, with and without final HA dip with several HA concentrations.

Samples may also be visualized using calcein-AM lysate stain. The calcein-AM lysate is reconstituted with 50 μl of DMSO. Ten μl calcein-AM were mixed in 5 mL phosphate-buffered saline (PBS) to obtain a 2 μM solution. The cell-rich media were aspirated, washed twice in PBS, and moved to well plates. Five hundred μL of stock solution are added to each well and then incubated with the sample for 20 minutes at room temperature. The staining solution was then aspirated from the wells, washed once in PCBE, and images obtained using fluorescence microscope imaging (62 HE BP 474/28, green).

An in vitro study was conducted to establish the biocompatibility of LLDPE-HA and PET-HA microcomposites. Reference and treated LLDPE and PET samples were sterilized with ethanol and ultraviolet irradiation, then placed for 24 hours in sterile 24-well plates containing sterile saline to enable sample hydration. Whole blood was acquired by venipuncture from healthy non-medicated adults, and collected into 6-mL vacuum tubes coated with ethylenediaminetetraacetic acid (EDTA) as ananticoagulant. The first 6 mL was discarded to prevent contamination from tissue thromboplastin activated by the needle puncture. Vacuum tubes were centrifuged at 150 g for 15 min, and plasma was pooled into a fresh tube. Blood was used within 2 hours of collection.

Five μL of whole blood were placed onto each sample. At identified time points (30 min and 60 min), samples were placed into a secondary sterile 24-well plate containing 500 μL diH$_2$O. The well plates were agitated for 30 seconds and rested for a total of 5 minutes. Samples were removed from the water-filled well plates and placed in a dry, sterile well plate to be processed for scanning electron microscopy (SEM).

Two hundred μL of the water/blood mixture from each well was placed into a 96-well plate for examination with a BMG Labtech FLOUstar Omega Plate Reader. An absorbance program was run using the plate reader. The red blood cells not trapped in a thrombus were lysed with distilled water, releasing hemoglobin into the water. The hemoglobin concentration in each well was measuring with the absorbance at 540 nm with 20 flashes per well. Omega MARS Data Analysis Software determined the free hemoglobin based on absorbance. The size of the clot was inferred as being inversely proportional to the absorbance value.

Platelet and leukocyte adhesion were assessed using the calcein-AM live stain (Invitrogen). Following incubation, plasma was aspirated and samples were rinsed twice with PBS to remove non-adherent cells. Samples were transferred to a new, sterile well plate and incubated in darkness in 500 μL of 5-μM calcein-AM solution at room temperature for 20 min. Samples were then rinsed in PBS and imaged using a fluorescence microscope (Zeiss) with filter set 62 HE BP 474/28 (green). Platelet and leukocyte adhesion were determined from resulting fluorescent images using ImageJ software.

Platelet and leukocyte morphology and activation were assessed using SEM. After sample incubation in plasma for two hr, samples were bathed in a primary fixative [6% gluteraldehyde (Sigma), 0.1 M sodium cacodylate (Alfa Aesar), and 0.1 M sucrose (Sigma)] for 45 min, then in a buffer solution (primary fixative without gluteraldehyde) for 2 hr, followed by consecutive 35%, 50%, 70%, and 100% ethanol baths for 10 minutes each. Samples were air dried and stored in a vacuum desiccator prior to preparation for SEM imaging. For SEM, samples were gold-coated (10 nm). Prepared specimens were stored under vacuum before imaging. Images were taken using a JOEL JSM-6500F field emission SEM (Tokyo, Japan). Images of the samples and the HA dipped surfaces were taken at 2000×, 5000×, and 10000× at 10.0 keV or 15.0 keV. One sample per group was selected for SEM analysis. Platelet and leukocyte morphology have been assessed on LLDPE 1% HA without surface dip and a tissue culture polystyrene (TCPS) control.

Aqueous contact angle measurements indicated that carboxylates were present and did affect the surface properties of the HA-treated microcomposites (Table 8).

TABLE 8

Aqueous contact angle measurements of sample verse controls at 10 minutes

| Sample | Aqueous Contact Angle (°) |
|---|---|
| LLDPE-Ref | 86.7 ± 2.3 |
| LLPE-T-0.5 | 62.3 ± 2.6 |
| LLPE-T-0.5-Dip | 39.0 ± 1.1 |
| LLPE-T-1.5 | 42.5 ± 2.7 |
| LLPE-T-1.5-Dip | 43.5 ± 6.7 |
| LLPE-T-2.5 | 54.4 ± 1.0 |
| LLPE-T-2.5-Dip | 39.1 ± 5.9 |

Figure 24:
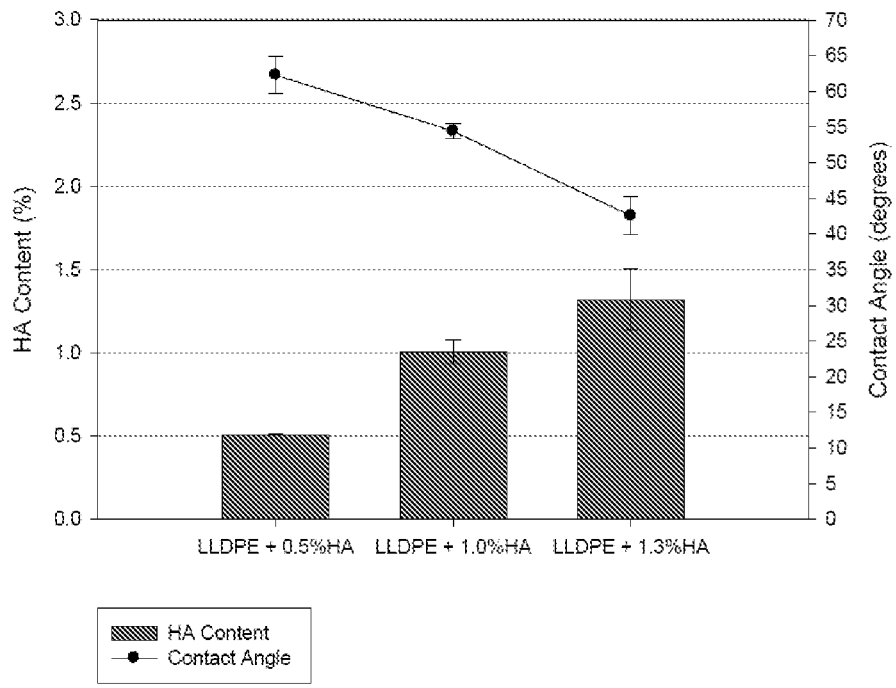
FIG. 24 shows a correlation between the HA content and the contact angle for the treated LLDPE samples that did not receive an additional HA dip.
Figure 25:
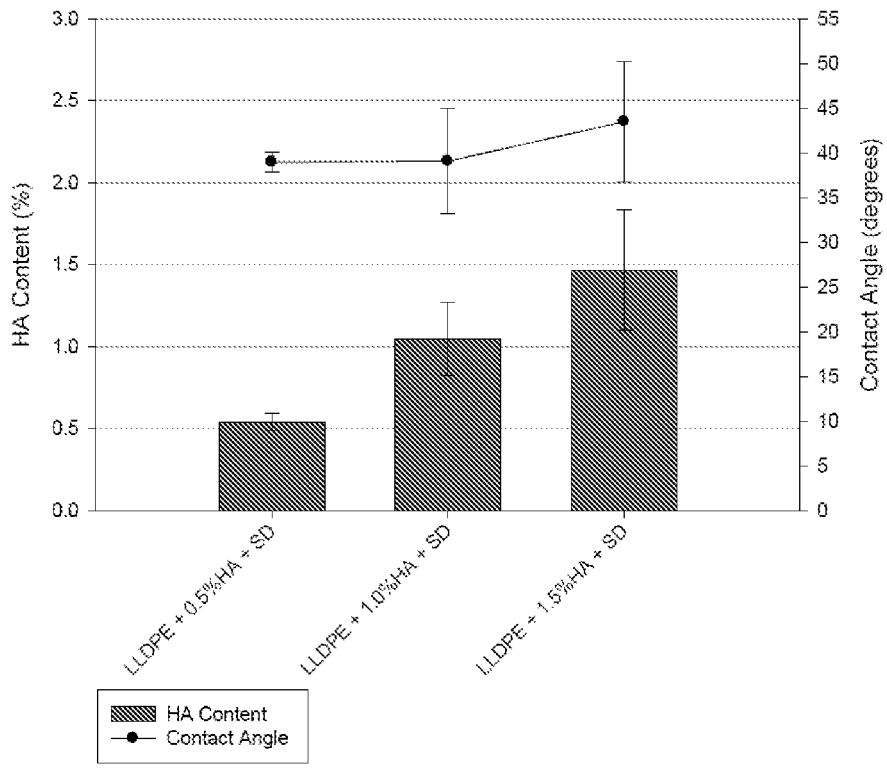
FIG. 25 shows no significant correlation between the bulk HA content and the contact angle for the treated LLDPE samples that did receive an additional HA dip due to the increased HA content at the surface.

The aqueous contact angles of those composites, which had a final HA dip, were significantly different from those that did not receive the additional dip treatment, except the LLDPE-T-1.5 and LLDPE-T-1.5-Dip samples. All samples were hydrophilic. The contact angle of the LLDPE control was very high exhibiting hydrophobic surfaces (FIG. 24). LLDPE-T sample groups exhibited significantly lower contact angles ($p \leq 0.001$) compared to LLDPE samples. With increasing HA surface density, contact angles decreased. Although less HA was in the LLDPE samples treated with the highest swelling solution concentration, those samples had the lowest contact angle with the additional dip treatment.

Samples that received the 1.5% w/v swelling treatment showed no difference with the addition of a post-hydrolysis HA dip treatment. The other two treatments benefited from this dip. Since the T-1.5 samples had the highest bulk HA concentration, the amount of HA in the microcomposite may have equilibrated or marks variances from the dip coating application. The additional % (w/w) XL HA on the surface could be the main contributor to the composite's lubricious properties and further reduction contact angle.

Figure 26:
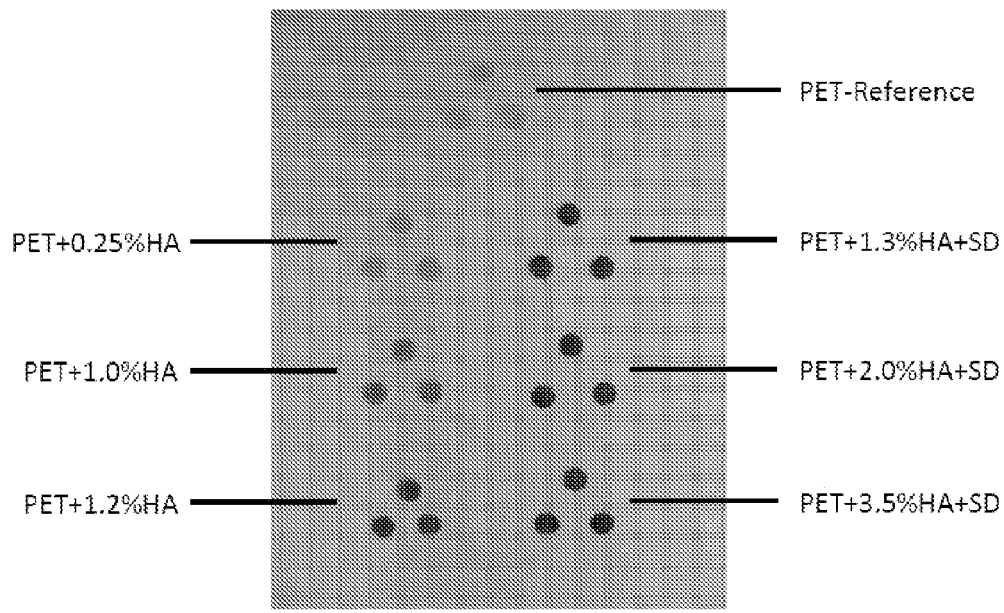
FIG. 26 shows TBO-stained PET fabric samples.

SEM images of treated and control PET samples, which had been stained with TBO, are shown in FIG. 26. The intensity of TBO is linearly proportional to the amount of HA on the surface: brighter blues correspond to higher concentrations of HA.

Figure 27:
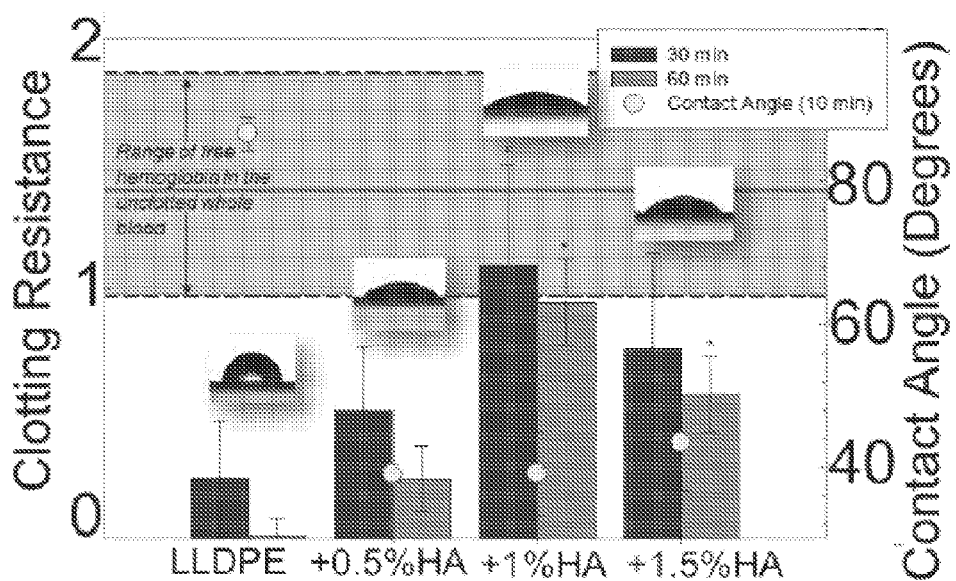
FIG. 27 shows the clotting resistance (free hemoglobin absorbance) for non-dipped samples for the 30-minute and 60-minute time points. The solid horizontal line is the mean, and the dashed lines above and below the solid horizontal line are the ±σ. Contact angles and overlaid images are shown for 10 minutes after drop application. The asterisk indicates significant differences (p<0.05) from the LLDPE-reference.
Figure 28:
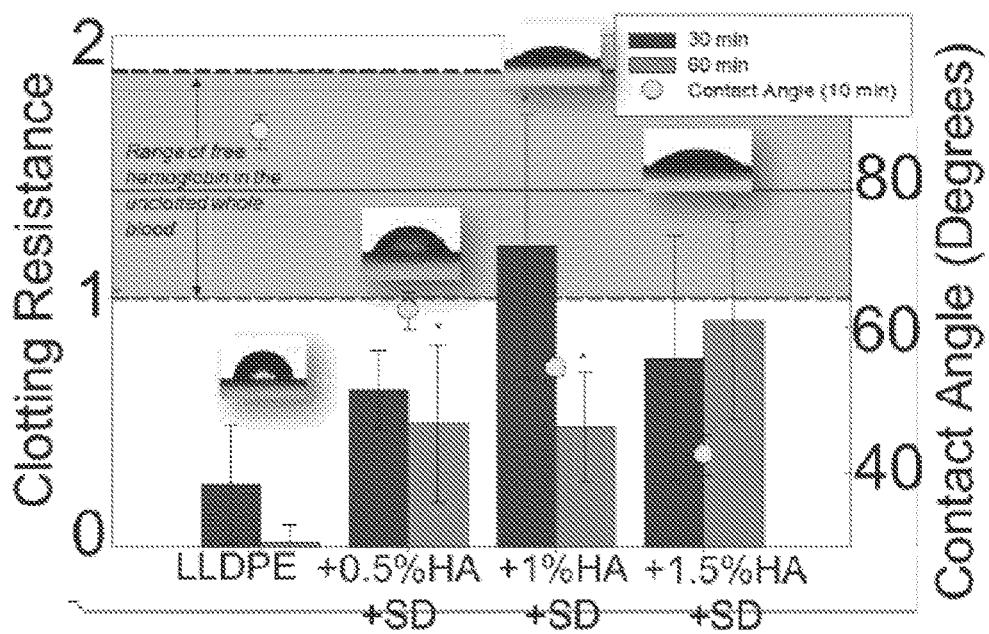
FIG. 28 shows the clotting resistance on left axis (free hemoglobin absorbance) for dipped samples for the 30-minute and 60-minute time points. The solid horizontal line is the mean, and the dashed lines above and below the solid horizontal line are the ±σ. Contact angles (right axis) and overlaid images 10 minutes after drop application. The asterisk indicates significant differences (p<0.05) from the LLDPE-reference.

Property values obtained from surface analyses, such as contact angle measurements, significant contribute to the understanding surface morphology and in vivo biocompatibility. Higher absorbance values correlate with improved thromboresistance of the material (FIGS. 27-30). FIGS. 27 and 28 show the resistances to clotting for LLDPE, with and without additional dip coating. The reference lines indicate the average absorbance for whole blood with zero clotting±one standard deviation. This line was used as a reference to gauge clotting percentages. Starred values (*) represent a significant difference ($p \leq 0.001$) compared to the control, which is the LLDPE-Ref sample.

The reference control was the Dowlex™ 2056 film washed in xylenes and dried before use. Blood incubated with untreated LLDPE completely clotted within 60 minutes. The LLDPE-T-2.5 treatment group had significantly higher ($p \leq 0.001$) resistance to clotting compared to LLDPE-Ref at 30 minutes while the other treatment groups did not have significant reduction in clotting, but did trend toward clotting reduction. In all treatment groups, clotting reduced significantly after 60 minutes compared to the untreated LLDPE-Ref, on which nearly all blood had clotted. The clotting was not significantly different between the treatment groups, suggesting that an equilibrium point for clotting was reached. The LLDPE-T-2.5 sample at 30 minutes was the only sample that did not show a significant amount of clotting ($p \leq 0.001$). SEM also provided similar results, where the degree of clotting did not vary significantly between the treatment groups. The overlaid plot of contact angle demonstrates a correlation between the reduction of contact angle and the increased clotting resistance. At 60 minutes, contact angles correlated well to the hemocompatibility.

Figure 29:
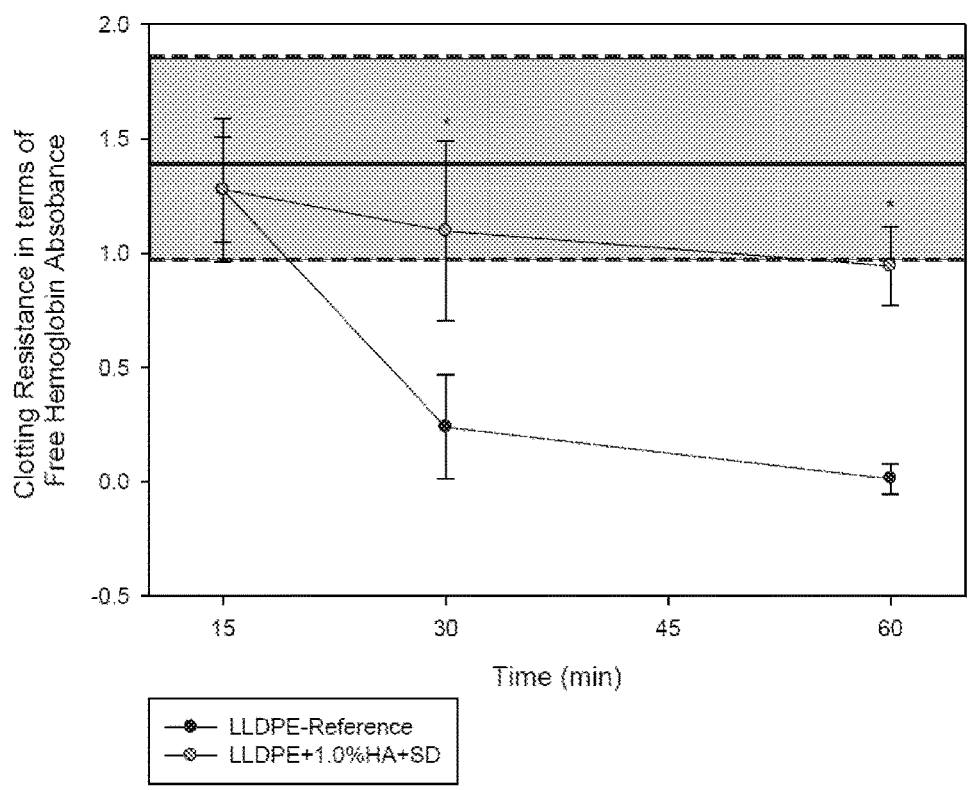
FIG. 29 shows the resulting clotting resistance (in terms of hemoglobin absorbance) versus time for the LLDPE-T-2.5-Dip.

The LLDPE-T-2.5-Dip treatment group had significantly higher ($p \leq 0.001$) resistance to clotting compared to LLDPE-Ref at 30 minutes, while the other treatment groups did not have significant reduction in clotting. In all treatment groups, clotting reduced significantly after 60 minutes compared to the untreated LLDPE-Ref, on which nearly all blood had clotted. The clotting resistance was significantly different between the treatment groups, with significantly less clotting on the LLDPE-T-2.5-Dip samples. Even though these samples did not have the highest HA content in the bulk polymer, the viscous swelling solution may have limited diffusion into the film. The LLDPE-T-2.5-Dip sample was the only sample that did not show a significant amount of clotting (p 0.001) for all time points (FIG. 29). Similar results were also observed using SEM, where the degree of clotting did not vary significantly between treatment groups until 60 minutes, at which point blood incubated with the LLDPE-T-2.5-Dip had a lower degree of clotting than both T-1.5-Dip and T-0.5-Dip treatments ($p \leq 0.05$), and the LLDPE-T-1.5-Dip had a lower degree of clotting than T-0.5-Dip treatments ($p \leq 0.05$). The overlaid plot of contact angle correlates the reduced contact angle with the increased clotting resistance. While the decrease in surface angle does not necessarily correlate directly to the clotting kinetics, it is a good indicator over the untreated LLDPE film. In other words, HA incorporation affects more than just the contact angle.

Figure 30:
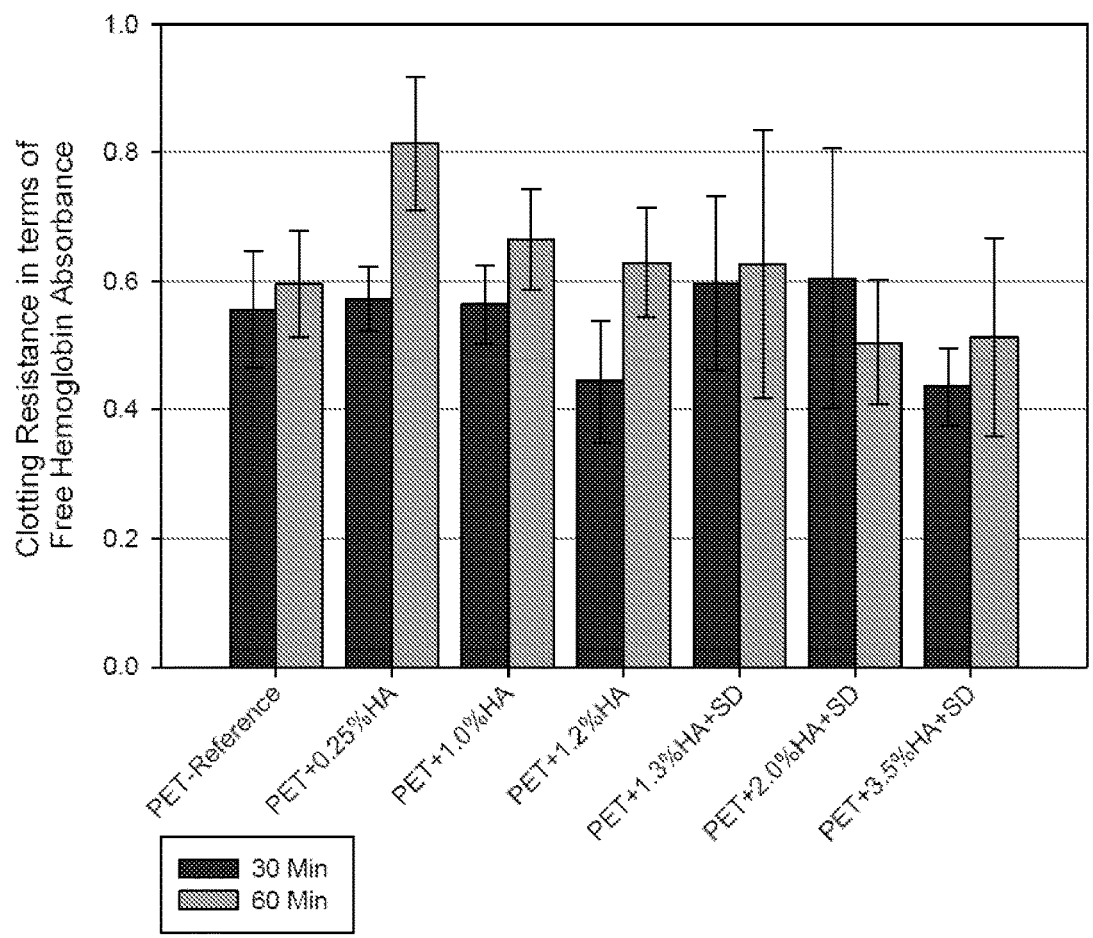
FIG. 30 shows the resulting free hemoglobin concentrations (in terms of absorbance) for PET samples for the 30-minute and 60-minute time points.

For PET fabric whole blood clotting, the reference control was the BARD Style 6010 thin polyester tubular woven (uncrimped) fabric, washed in xylenes, and dried before use. The material's morphology allowed the whole blood to pass through the sample and remain in the first well plate. Thus, the results for whole blood clotting time with the PET fabric were inconclusive (FIG. 30). Qualitative analysis using SEM, however, showed a thromboresistance for the treated fabrics, which increased with increasing HA content. Unlike the LLDPE film, the higher viscosity of the T-2.5 swelling solution did not alter the swelling kinetics of the PET. The high porosity of the fabric allowed for greater penetration and absorption of the swelling solutions.

Scanning electron micrographs of the LLDPE and PET after contact with whole blood for 30 and 60 minutes are presented in FIGS. 31-34. Unmodified LLDPE and PET samples were covered with an accumulation of fibrin and thrombus, while treated LLDPE and PET samples showed almost no sign of cellular matter. The inhibition may be caused by reduction in contact angle at the interface, reducing protein absorption and, consequently, progression of the coagulation cascade.

Figure 31:
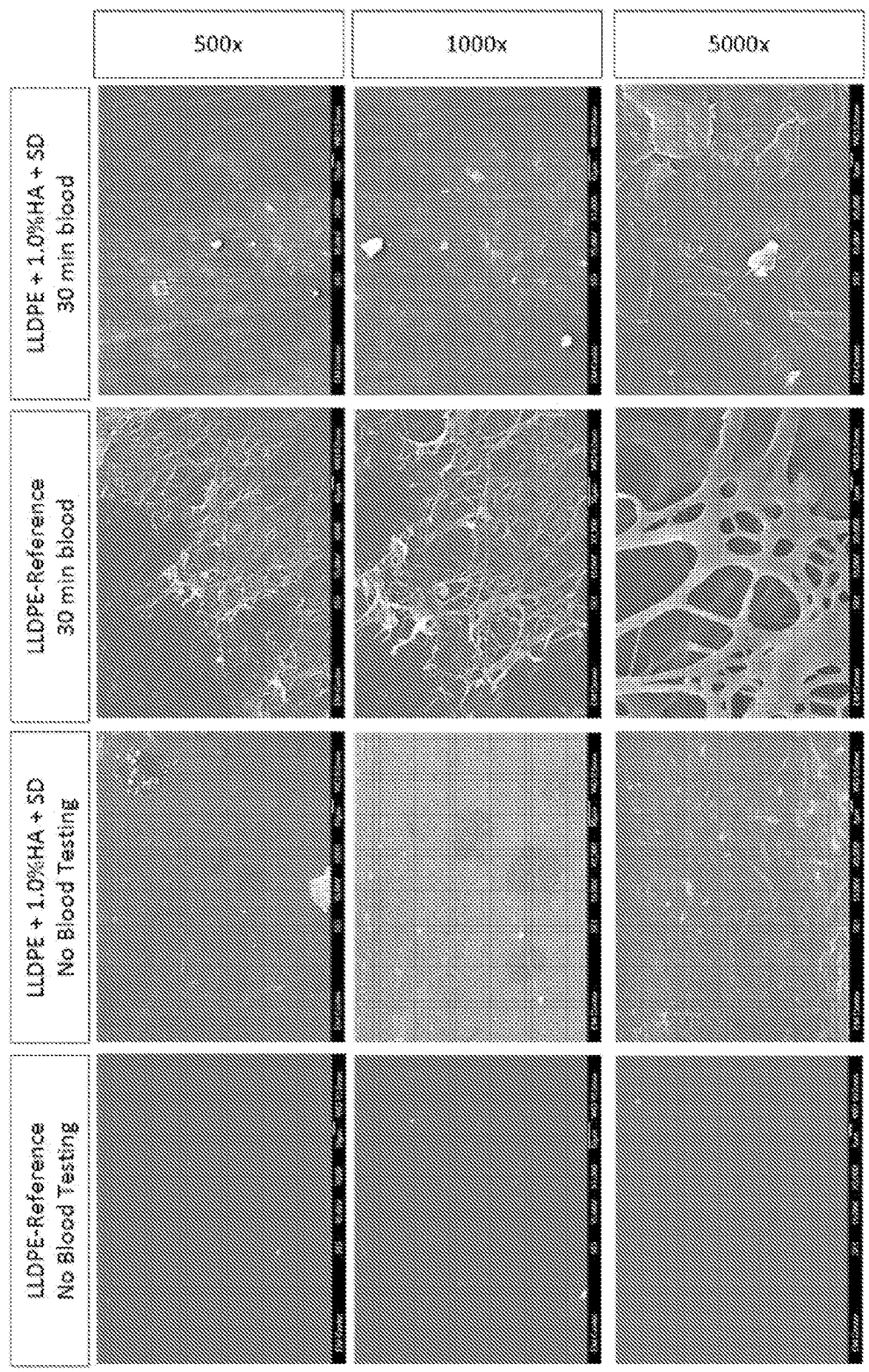
FIG. 31 shows the scanning electron microscopy (SEM) images of LLDPE samples prior to blood clotting compared to the same microcomposite and reference samples following 30-minute whole blood clotting.
Figure 32:
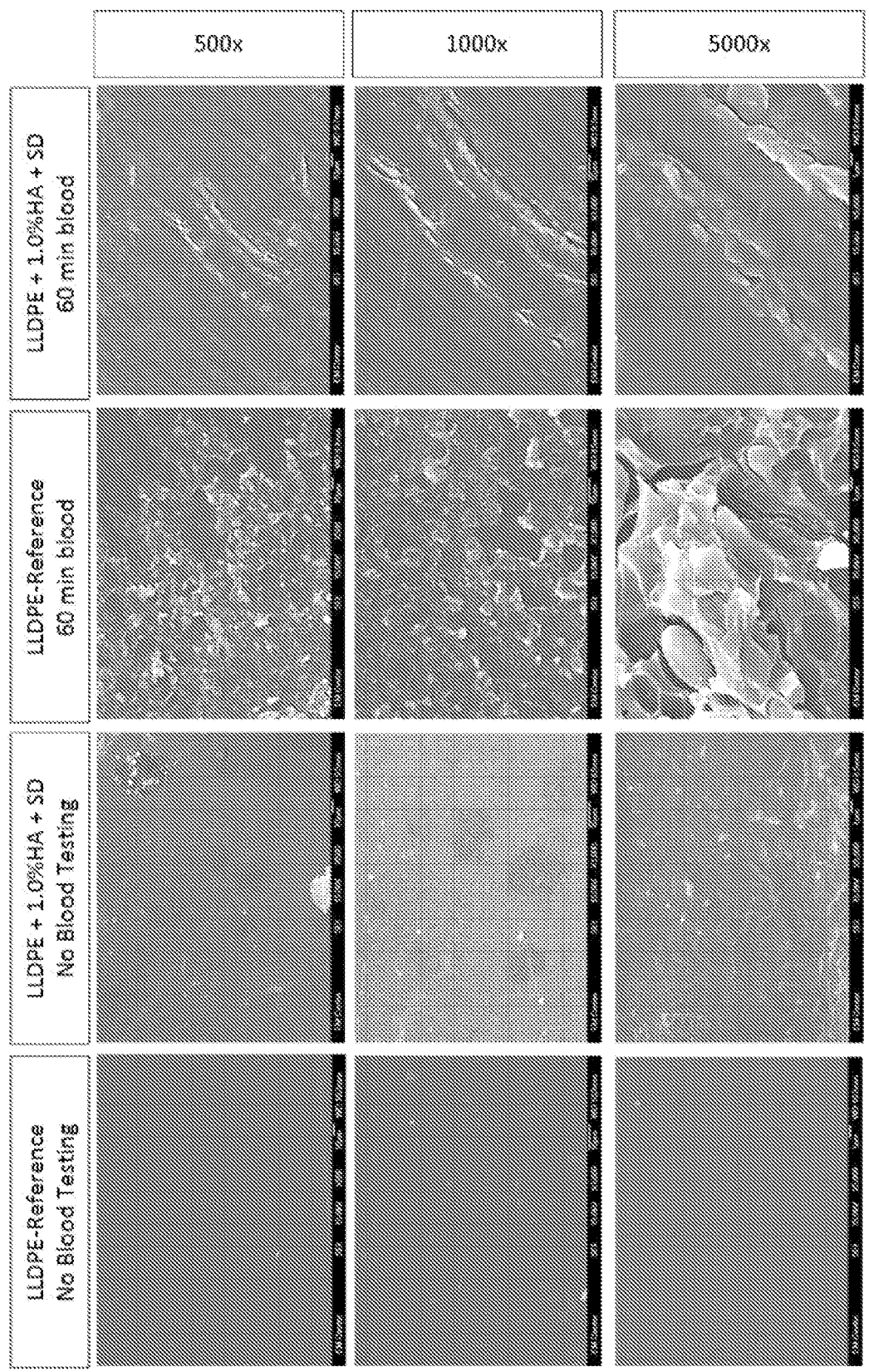
FIG. 32 shows the SEM images of LLDPE samples before blood clotting compared to the same microcomposite and reference samples following 60-minute whole blood clotting.

Fibrin develops on the untreated LLDPE samples within 30 minutes of exposure with whole blood (FIG. 31). After 60 minutes, fibrin attachment progressed to form thrombus on the untreated samples. Fibrin attachment is not seen in the treated LLDPE sample. In the images of the treated sample before blood testing, the HA addition is seen. The surface looks very similar after exposure to whole blood for 30 minutes. Islands of HA are correlated to the non-uniform distribution of surface HA. After 60 minutes, thromboresistance is still seen (FIG. 32). Some cellular attachment is seen in clumps of fibrin; however, these spots were very scattered.

Figure 33:
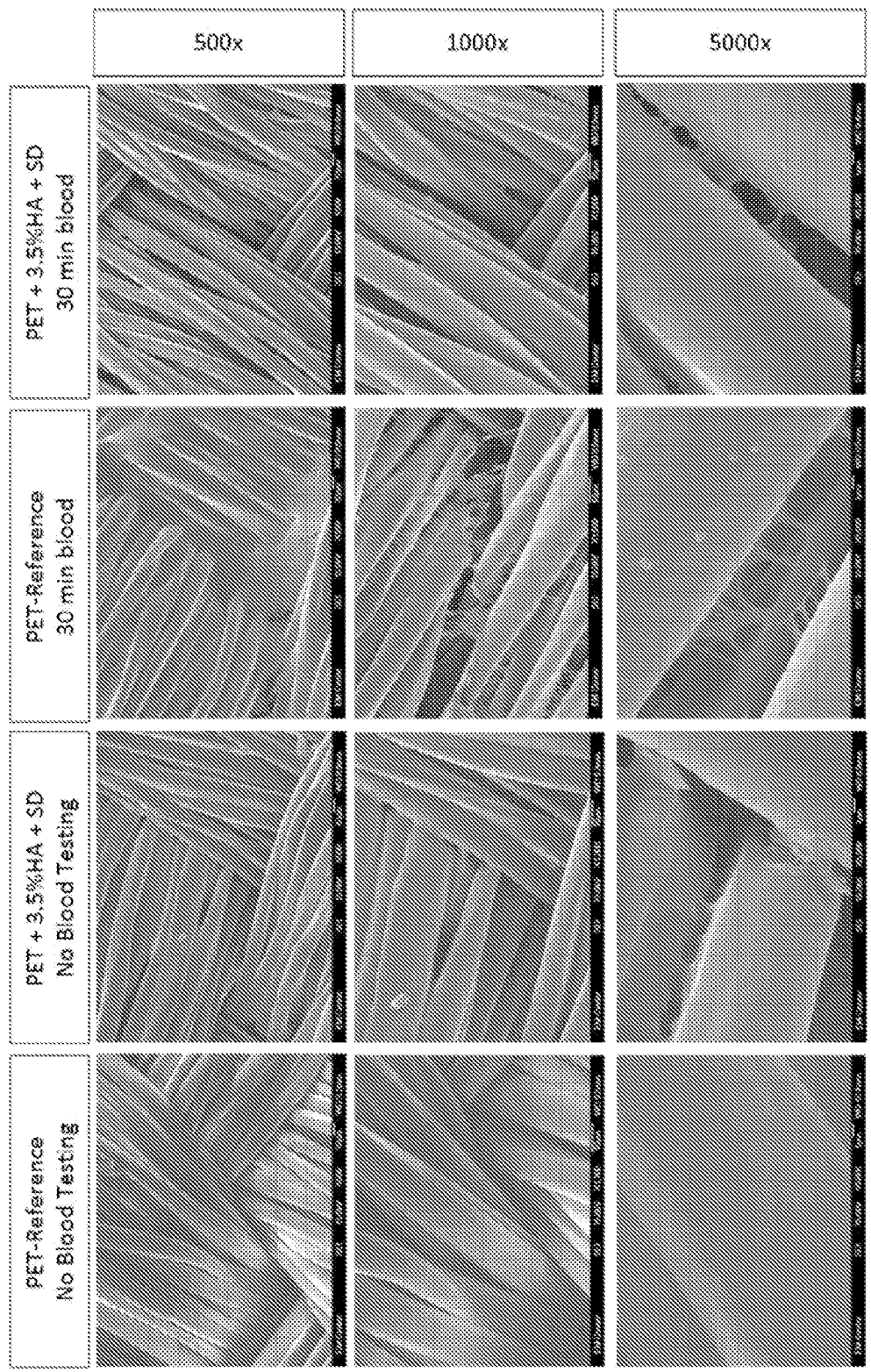
FIG. 33 shows the SEM images of PET samples prior to blood clotting compared to the same microcomposite and reference samples following 30-minute whole blood clotting.
Figure 34:
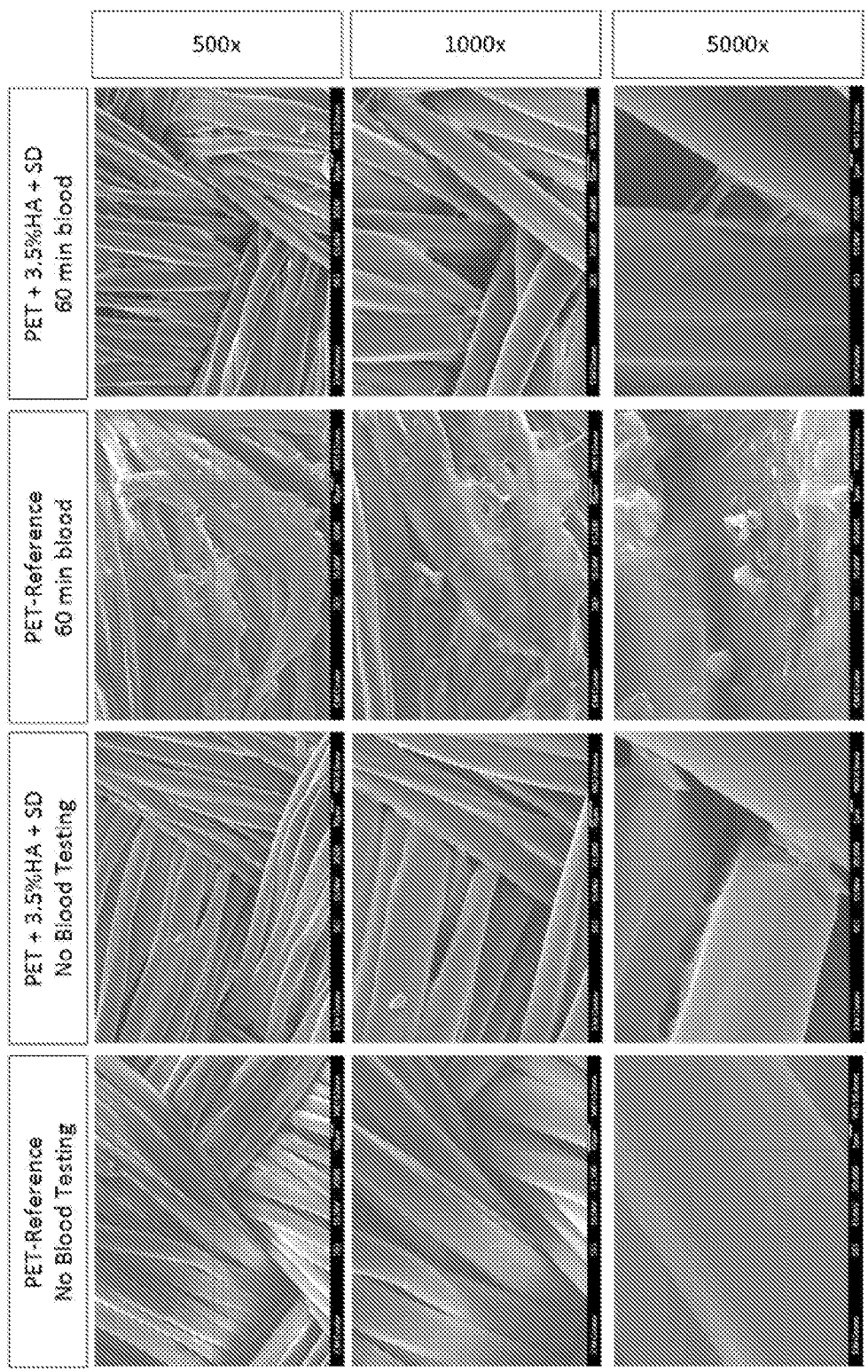
FIG. 34 shows the SEM images of PET samples prior to blood clotting compared to the same microcomposite and reference samples following 60-minute whole blood clotting.

PET fabric had more astounding results from the SEM imaging. The addition of the HA is seen between the fibers (FIGS. 33 and 34). This HA is links some fibers together, explaining the increased bending stiffness of the higher HA content samples. Both the treated and untreated PET samples were permeable to blood, allowing most cells to pass between the fibers. Nonetheless, fibrin attachment still occurs on untreated samples after 30 minutes of blood exposure. In some areas, voids between yarns were almost completely occluded. Fibrin attachment was not seen for the HA treated samples; HA connections between fibers were still visible with no fibrin attachment. After 60 minutes, the untreated samples have significant clotting, covering many fibers and voids. Some fibrin may be seen in the treated PET sample after 60 minutes of exposure to whole blood, but it is significantly less than the untreated samples after only 30 minutes. This reduction in thrombus indicates a good hemocompatibility with the addition of the HA to the structure. SEM images demonstrate the excellent hemocompatibility with whole blood. PET-T-2.5 samples showed the greatest thromboresistance.

Taken together, these data suggest that under the conditions tested, treated PET and LLDPE are less thrombogenic than untreated reference samples. The reduced contact angles of LLDPE following treatment, compared to those of non-treated LLDPE controls, correlate to reduced thrombus formation, shown by increased absorbance and decreased cellular attachment. Sample groups that exhibited lower contact angles generally displayed better in vitro hemocompatibility.

Figure 44:
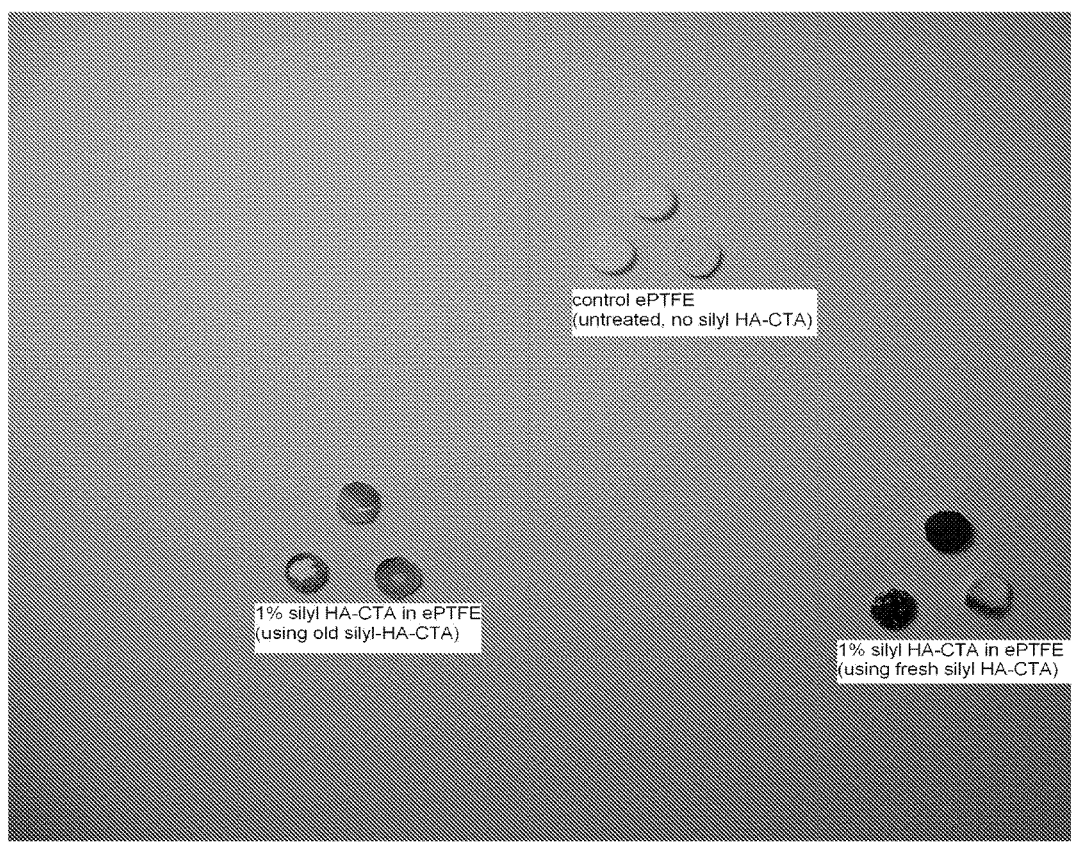
FIG. 44 depicts TBO staining, which indicates that ePTFE wicked up the silyl HA-CTA using the soaking method for 15 minutes, followed by hydrolysis.

Expanded polytetrafluoroethylene (ePTFE) was also treated with silyl HA-CTA using the procedures discussed above. TBO staining indicated that the ePTFE wicked up the silyl HA-CTA using the soaking method for 15 minutes, followed by hydrolysis (FIG. 44).

Example 5: Human Platelet Adhesion Study

Figure 35:
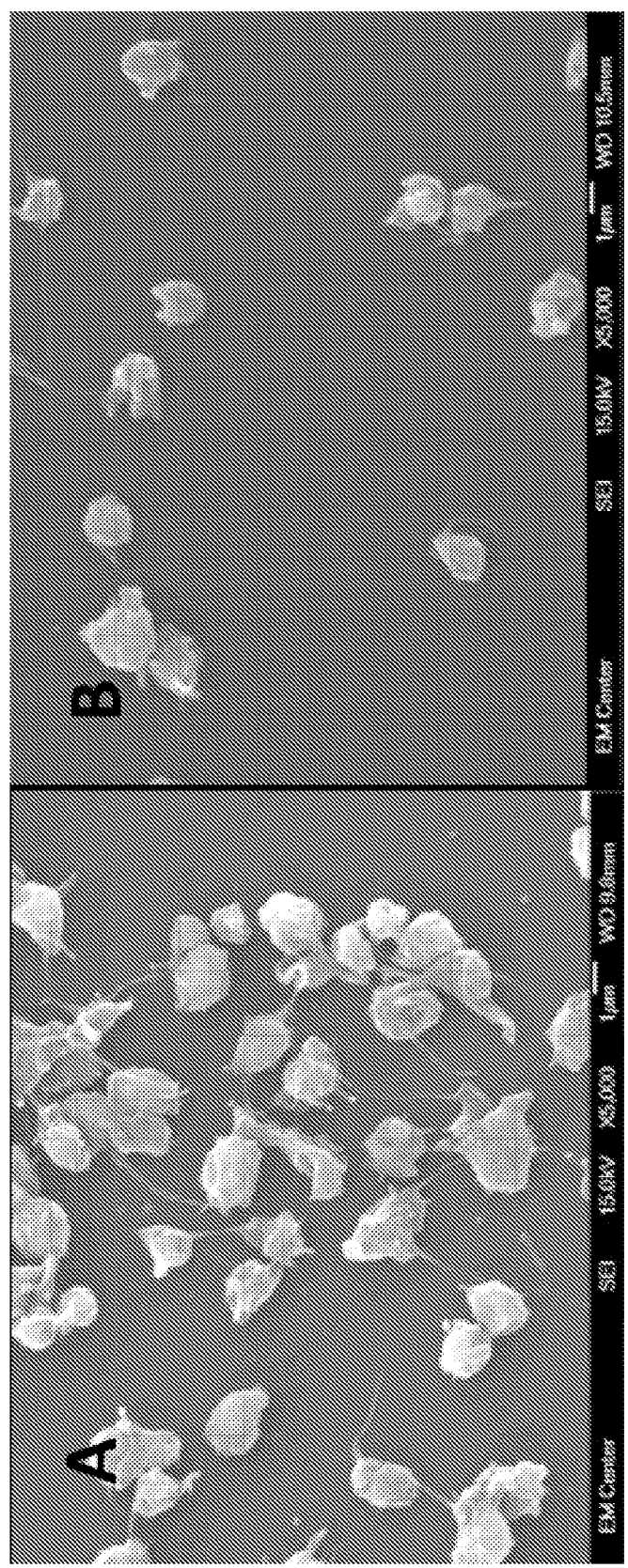
FIG. 35 shows platelet adhesion and activation of LLDPE-reference (A) and LLDPE-T-1.0 (B).

We also investigated human platelet adhesion and activation on LLDPE and LLDPE-T-1.0 after 2 hours of incubation. SEM images shown in FIG. 35 indicate significantly reduced platelet adhesion on the LLDPE+1.0% HA sample. The platelets have dendritic morphology on untreated LLDPE with many platelets showing longer dendrites than those on LLDPE+1.0% HA (FIG. 35).

Figure 36:
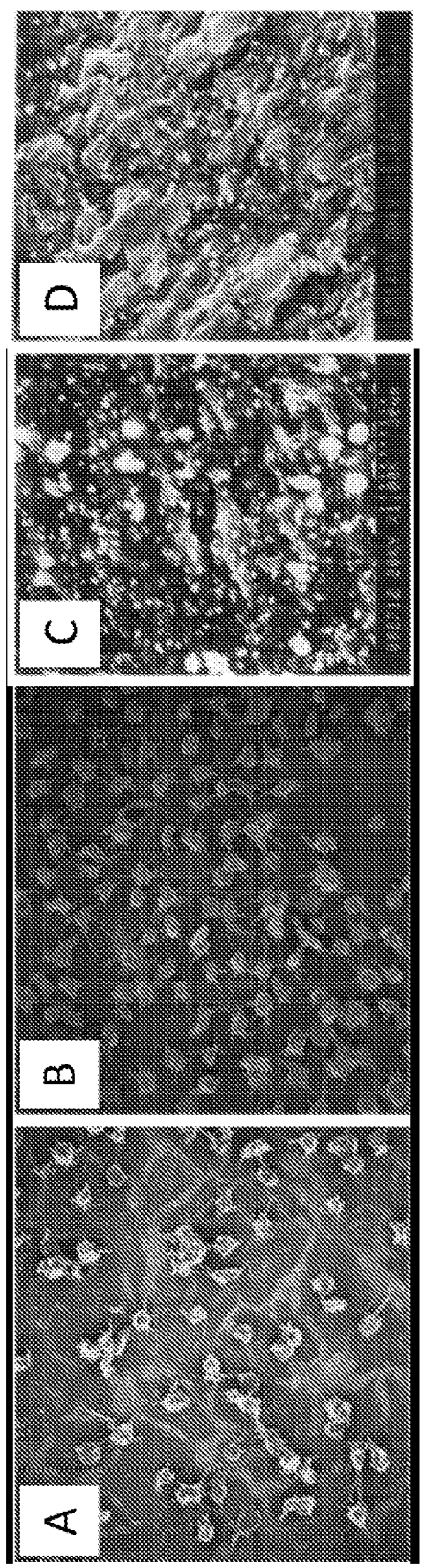
FIG. 36 shows representative platelet data on pyrolytic carbon (A), polyethylene (B), glutaraldehyde-fixed bovine pericardium (GFBP) (C) and, GFPB with heparin (D).

Most hydrophobic synthetic polymers are not very hemocompatible. Furthermore, although bioprosthetic HV leaflets are more hemocompatible than mechanical valve (such as, pyrolytic carbon) leaflets, both materials result in platelet adhesion and activation, as shown in FIG. 36. Composite leaflets may be at least be as hemocompatible as fixed-tissue, bioprosthetic leaflets, if not more so. Despite the different magnifications in FIGS. 35 and 36, FIG. 35B shows that composite elicits almost no platelet adhesion, while the untreated polyethylene does. The polyethylene results (FIG. 36B) are very similar to our untreated polyethylene results (FIG. 35A), and the pyrolytic carbon (FIG. 36A) results in more platelet adhesion than the composite (FIG. 35B). FIG. 36C-D compares platelet adhesion on fixed pericardium and fixed pericardium treated with heparin. None of these materials is as resistant to platelet adhesion as the composite.

Example 6: Hemodynamic Testing of Heart Values Using Composite Leaflets

Figure 38:
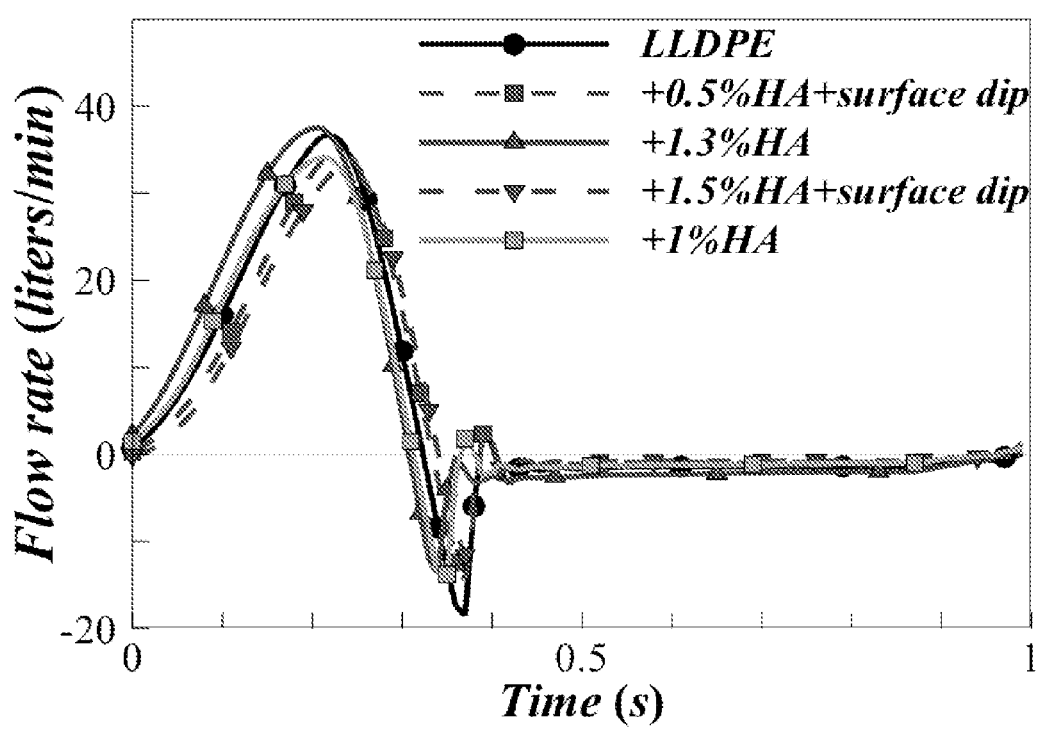
FIG. 38 shows measured flow rate curves for the tested composite HVs under mean aortic pressure of 100 mmHg and cardiac output of 5 liters/min (Left)
Figure 39:
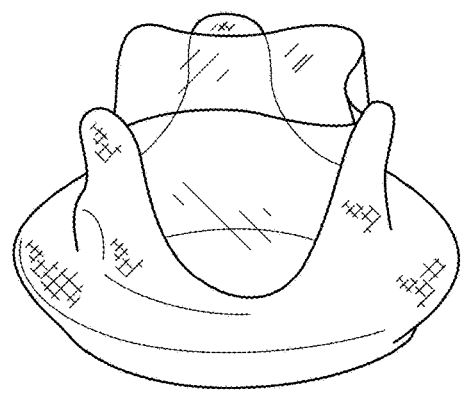
FIG. 39 shows a composite HV ready for in vivo implantation.

A snap-on design was developed with CAD and three-dimensional printing technology (Stratasys Inc.) to rapidly assemble HVs from pre-cut leaflets. The geometry of the stent and the profile height were based on the Carpenter Edwards pericardial valve. Preliminary trileaflet HVs were made from sheets of LLDPE, LLDPE+0.5% HA+surface-dip, LLDPE+1.3% HA, LLDPE+1.5% HA+surface-dip, and LLDPE+1.0% HA. FIG. 38 shows exemplary frames/snapshots from high-speed video studies of these valves in the closed and open configurations under physiological loading in the left heart simulator. FIG. 39 shows ensemble averaged flow rate waveforms. The valve with the least regurgitation (LLDPE+1.5% HA+surface-dip) showed only 4.77±0.42% of the forward flow regurgitating during diastole. The corresponding regurgitate volume was 4.6±0.4 mL/beat, which is slightly above the range for stented bioprostheses but well below that of mechanical valves. For all the valves measured the effective orifice area (EOA) was in the range 2.34±0.52 cm$^2$ for the same valve size. A composite valve prosthesis was manufactured that could be use in the animal studies. FIG. 39 shows the valve prosthesis with sewing cuff using the Autogenics model (vandeWal H, Bennink G, Haanschoten M C, Meijboom E J., "Autologous tissue cardiac valve: Implantation in children." Journal of Thoracic and Cardiovascular Surgery, 112:846-848 (1996), which is incorporated herein by reference in its entirety).

TABLE 9

Comparison of composite heart valve to mechanical and bioprosthetic valves

| | composite Valve | Mechanical Valve | Bioprosthetic Valve |
|---|---|---|---|
| Valve Characteristic | | | |
| Natural Fluid Dynamics | Yes | No | Yes |
| Durable | Yes | Yes | No |
| Antithrombogenic materials | Yes | No | Yes |
| No long-term calcification | Yes | Yes | No |
| Clinical Program | | | |
| No need for strong anticoagulation | Yes | No | Yes |
| Younger patients | Yes | Yes | No |
| Transcatheter feasible | Yes | No | Yes |
| Manufacturing | | | |
| Composition control and uniformity | Yes | Yes | No |
| Easily shaped, low cost, automated | Yes | No | No |

Example 7: LPN HV Assembly: Parameters, Valve Stent Profile, and Perimeter Geometry The overall aspect ratio of the valve prosthesis, which is defined as the ratio of the height of stent post to the inner diameter of the valve annulus, governs the stent profile. This parameter may control the amount of leaflet area available for coaptation. Too small a profile for leaflets made from flat sheets may lead to increased regurgitation. Valves of size 25 mm with an aspect ratio 0.5, 0.65, and 0.8 are made and tested. This parameter also helps identify optimal geometry to avoid "pin-wheeling" known to induce additional structural stresses within the leaflets and impact long-term durability. The leaflet perimeter shape is studied by comparing closing dynamics and regurgitation levels for flat edged leaflets to circular edged leaflets. This guides improvement in leaflet coaptation and reduce regurgitation. The axial length of the leaflet at the tip is adjusted to be higher than the length at the commissures at the time of cutting leaflets. There levels of differences, 0 mm, 2 mm, and 4 mm, are studied. The higher the difference, the more leaflet area is available for coaptation at the center.

Example 8: LPN HV Hemodynamics, Kinematics Characterization, and Durability

Figure 40:
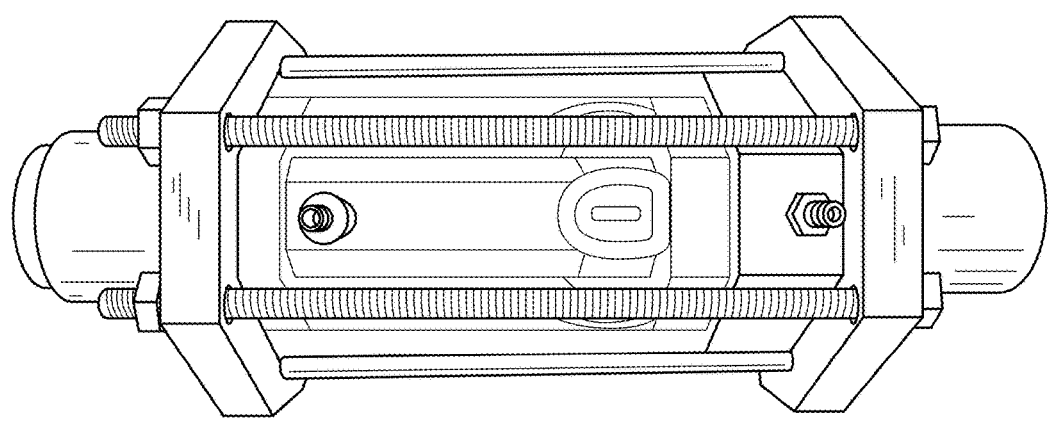
FIG. 40 shows an optically clear straight aorta model with three sinuses.
Figure 41:
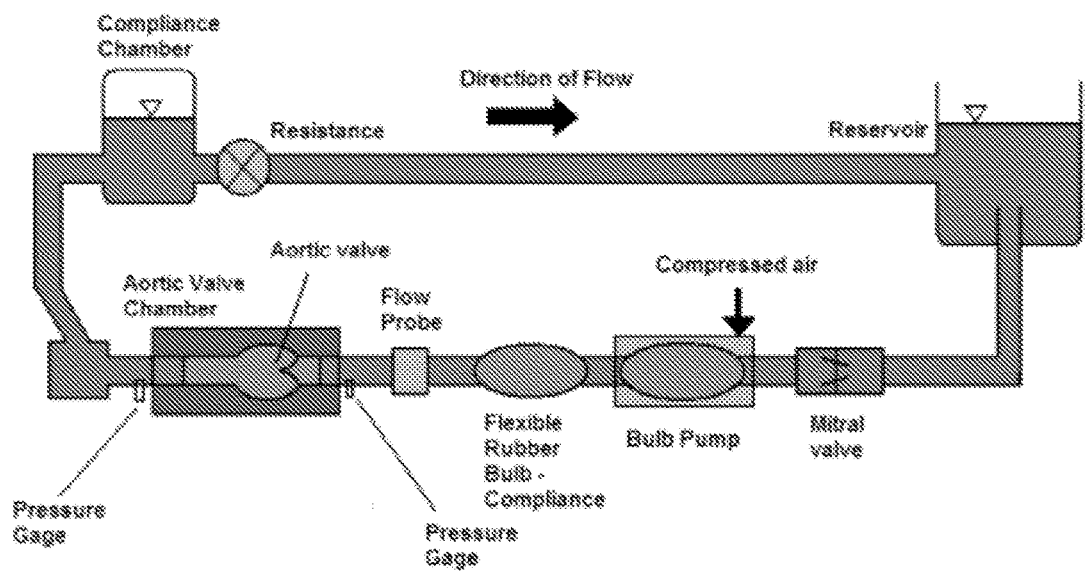
FIG. 41 shows a schematic of the physiological left heart simulator for in-vitro hemodynamic testing, time-resolved particle image velocimetry, and valve kinematics measurements.

Hemodynamics and kinematics of the different configurations of composite HVs (defined in Example 7) are compared to that of a clinical quality 25 mm St. Jude Bileaflet Mechanical HV (donated by St. Jude Medical) and the Carpentier-Edwards Pericardial Tissue HV (obtained through the Veterinary Hospital). These measurements are performed using the dynamic in vitro left heart simulator system (FIG. 41). The valves are placed in a specialized straight three-sinus aorta model for highly controlled comparison while permitting full optical access. The aorta model is shown in FIG. 40 with the three sinuses designed based on the art. Viscosity and refractive-index matched water-glycerin-NaI Blood analog are used as the flow loop fluid for composite HVs and mechanical HV. Saline will be used as the working fluid for THV (to preserve tissue mechanical properties). The flow loop is tuned to physiological and pathophysio-logical conditions described in the section "matrix of experiments" below. For each condition, the flow field downstream is measured using TRPIV in addition to bulk hemodynamic performance parameters (EOA, pressure gradient, and regurgitant fraction), high-speed videos of marked leaflets are collected.

A. Valve Kinematics Measurements

Figure 37:
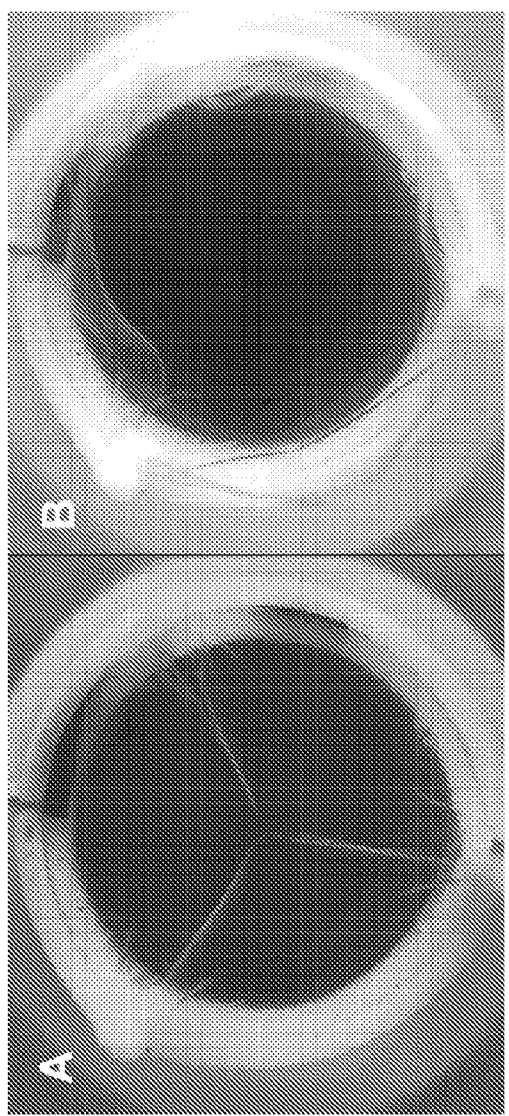
FIG. 37 shows a single frame of high-speed (1000 fps) leaflet kinematics study of composite HV in the aortic position during diastole (A) and systole (B).

Valve leaflet motion is mapped in detail using high-speed video (LaVision Inc.). Leaflet opening and closing times are compared between composite HVs, mechanical HV, and bioprosthetic HV, and to data of numerous other clinical prosthetic valves. Example frames from the high-speed video are shown at FIG. 37. Using a marking dye (Thermoelectron Corporation, Pittsburgh, Pa.), a regular array of markers are placed on the leaflet surface. These markers are tracked over the cardiac cycle for leaflet kinematics and stretch computations. Two views are mapped into the single high-speed camera using mirror arrangements to gain a stereoscopic view of each leaflet. This image acquisition is gated to the acquisition of hemodynamic data through the pulse programmer. At the end of dynamic image acquisition, without draining fluid from the loop, both the ventricular and aortic chambers are exposed to atmospheric pressure and the valve assumed its static, zero-transvalvular pressure configuration. Images of the valve leaflets in this state are captured, and the corresponding leaflet geometry are used as the zero-pressure reference configuration for stretch computation. The arrays of markers at the region of interest are tracked using a custom Matlab program from 2D images from both cameras. Direct Linear Transformation converts these 2D coordinates of the markers to 3D coordinates through the resolution of the relative angle between the two views. To calibrate for the angle between the stereoscopic views, a 5-mm metal cube is inserted into the chamber at the location of the leaflets, and images of the cube are captured from both views. Coordinates of the seven visible vertices of the cube are used to compute view angle and position. Shell-based 2D isoparametric finite element shape functions are used to fit leaflet surface geometry described by the 3D coordinates of markers. These shape functions may be used to compute the dynamic principal stretches. The unstretched reference state is taken as the state when the flow loop is stopped and pressure in both the ventricular and atrial chambers are equilibrated.

B. Valve Hemodynamic Performance

All standard prosthetic valve hemodynamic measures, such as effective orifice area (EOA), regurgitant volume fractions, mean and peak pressure gradient, valve opening and closing times, define the bulk hemodynamic performance endpoints for the above conditions. These parameters are evaluated on each of the valves tested, for a minimum N=50 (cycles) each C. Flow Field Measurements Detailed measurements of the turbulent velocity field are acquired in the immediate vicinity of the valves (both upstream and downstream). TRPIV methods include the use of the PIV system (LaVision, Germany) for data acquisition and processing. The flow loop fluid is seeded with 1-20 microns melamine resin particles coated with Rhodamine-B. The Neodymium-doped Yttrium Lithium Fluoride (Nd:YLF) Single Cavity Diode Pumped Solid State High Repetition Rate Laser (Photonics Industries, Bohemia, N.Y.) is used with a combination of lenses to illuminate a 0.2 mm thick measurement plane through the valve holder. A double frame complementary metal-oxide-semiconductor (CMOS) camera (Photronix, Inc) is positioned orthogonally to the laser sheet to gain a good field of view of the particle-laden flow distal to the leaflets. To correct image distortion due to camera angle and chamber geometry, a calibration grid is inserted into the field of view region, and DaVis (Lavision, Inc) image calibration algorithm is applied to images of the grid. Measurements are acquired across a stack of PIV slices spanning the valve model with slice spacing of 3 mm. For each slice an ensemble of approximately phase locked 500 measurements are captured at a given cardiac phase to enable statistical characterization of the flow field and capture cycle-to-cycle variations in the flow. Simultaneous ventricular and atrial pressure measurements are made for at least 500 phases of the cardiac cycle.

Figure 42:
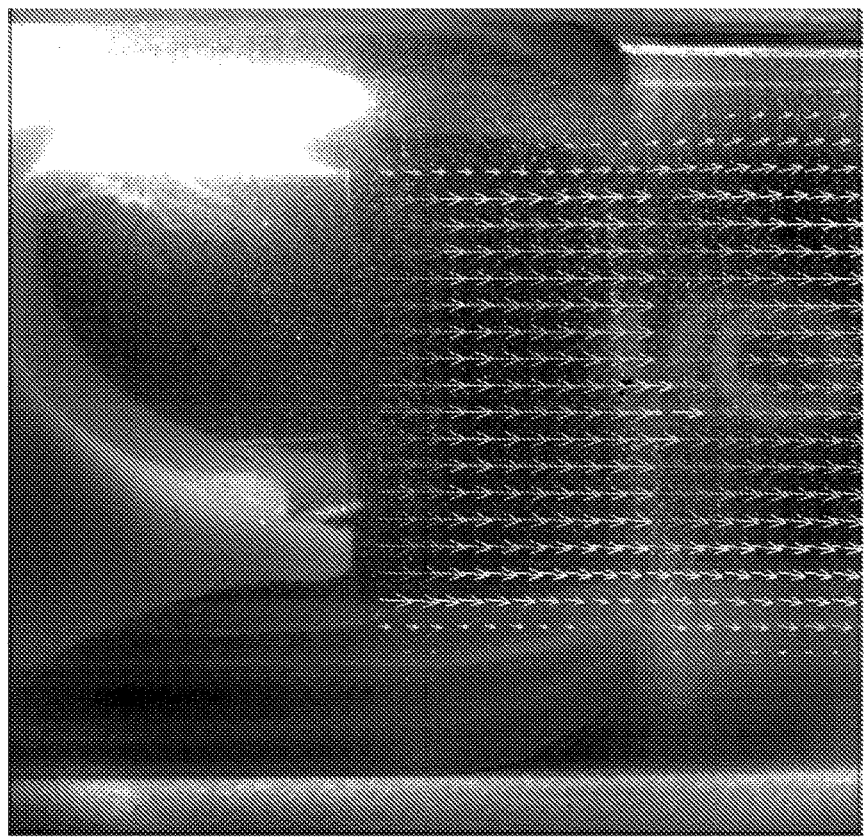
FIG. 42 shows an example of measured turbulent velocity field downstream of the composite HV using TRPIV.

The results yield viscous and turbulent shear stress estimates in the vicinity of the valve. FIG. 42 shows a snapshot of the particle image velocimetry raw image overlaid with the computed turbulent velocity field along the center plane during peak forward flow through the composite HV. The PIV measurements are gated with the pulse programmer of the flow loop, and programmed to record 500 phases over the cardiac cycle. Detailed characterization of the data, which includes viscous and turbulent stresses, are performed with protocols known in the art.

D. Fatigue Measurements

Test valves are placed in a HV fatigue tester and subjected to testing under left heart conditions, as detailed above, at a pulse rate of 30 Hz to cycle levels of 0, $8\times10^4$, $4\times10^5$, $2\times10^6$, $10\times10^6$, and $50\times10^6$ cycles. Two valves run at each accelerated testing level, resulting in six leaflets per accelerated testing level. These levels are chosen to plot fatigue data described below on log base 5 plots and project damage to 1 billion cycles. After each fatigue test, bulk hemodynamic properties are reevaluated under conditions detailed above. Structural damage is assessed macroscopically and microscopically. Tensile testing quantifies the reduction in strength. The amount of HA remaining in the bulk of the leaflets is quantified using TGA, and the remaining surface density (nmol/cm$^2$) of HA is quantified using TBO staining. Scanning electron microscopy is used to examine the leaflets for any signs of fatigue damage.

E. Matrix of Experiments

PIV and Kinematics measurements are conducted for the following variations:

(1) Stroke volume (50 mL, 70 mL, and 90 mL): These three stroke volumes determine the overall cardiac output for a given heart rate. They also determine the flow Reynolds number (as high as 6000) and dictate the systolic pressures.

(2) Heart rate (normal=60 bpm and high=120 bpm): Heart rate governs the Womersley number of the flow and dictates the extent to which unsteady flow develops. The systolic duration fraction is one-third for 60 bpm and one-half for 100 bpm. High Womersley numbers produce high shear rates at the aorta wall and significant phase lag between the near leaflet flows and the flow in the core of the lumen. Two different heart rates are therefore be tested, corresponding to normal (60 bpm) and tachycardia (120 bpm) conditions.

(3) Mean Aortic Pressure (normotensive=100 mmHg, hypertensive=130 mmHg, severe hypertensive=160 mmHg): Hypertension may significantly alter leaflet kinematics and, therefore, the leaflet strain distributions. Normotensive, hypertensive, and severe hypertensive conditions are achieved by adjusting the downstream resistance and compliance of the flow loop.

4. Statistical Analysis and experimental repetitions: For each parameter combination, eight repeated measurements are conducted on a total of n=3 HVs each. Shear stresses, flow fields and stretch are displayed as the mean and standard deviation of the trend over the cardiac cycle. Average stretch over diastole and over systole, and the stretch rates during closing and opening phases are displayed as the mean and standard deviation.

Example 9: Further LLDPE-HA Compositions

The 1.5% and 2.5% silylHA swelling treatment groups are repeated with a new treatment group of 2.0% silylHA. Contact angles are measured on all samples. TGA and weight change measure the bulk HA concentration. Surface density (nmol/cm$^2$) of HA is quantified using TBO staining. Cross sections of the TBO stained samples are examined with optical microscopy to determine if the HA concentration is uniform throughout the cross section, elucidating whether swelling in the more concentrated viscous HA solutions results in more HA near the surfaces even though the overall amount of bulk HA is less than that achieved with the lower viscosity, lower concentration swelling solutions. If significant differences are found between the bulk amount of HA (or the surface density of HA) in the three different treatment groups, the 1.75% and 2.25% treatments will also be made. Half the samples from these bulk treatment groups are put through the improved surface dipping protocol. The % HA gain are estimated by weight gain and measured with TGA, and the HA surface density and cross-sectional distribution quantified with TBO staining and microscopy. Contact angle measurements are made on all samples. All samples show contact angles well below 60° and in some cases below 40°. All treatment conditions which result in samples with statistically significant different bulk HA %, surface HA % or HA surface density and exhibit contact angles are put through hemocompatibility testing. Correlations and interactions are observed between those results and the aqueous contact angles, bulk % HA, the surface % HA, and/or the surface density of HA for all treatment groups.

Example 10: Ex Vivo Hemocompatibility

Which of the samples have the best in vitro hemocompatibility before proceeding to the in vivo animal studies is determined. The exposure of materials to blood introduces serious and ongoing concerns regarding poor blood-biomaterial interactions, such as undesired protein adsorption, platelet adhesion/activation, leukocyte recruitment and further immune response, potentially leading to thrombus and clinical failure. A minimum sample size of n=9 is used in each test described below. Plain LLDPE, glutaraldehyde-fixed bioprosthetic tissue like that used in bioprosthetic HVs, and pyrolytic carbon surfaces similar to that used in mechanical HVs, are used as controls. The following tests evaluate the effect of these various material compositions on whole blood, platelets, leukocytes, and monocytes/macrophages. The effect is evaluated for these various material compositions on endothelial cells (ECs) under static and dynamic conditions.

A. Evaluate Blood Serum Protein Adsorption on Leaflet Materials.

Whole human blood is centrifuged to separate plasma from the red blood cells. The leaflet materials are incubated with plasma for 2 hours. Fibrinogen, albumin, and immunoglobulin-G adsorption on leaflet materials is evaluated using an ELISA to understand how serum proteins interact with the surfaces.

B. Evaluate Whole Blood Clotting Kinetics on Leaflet Materials.

To evaluate the clotting properties of leaflet materials, their interaction with whole blood is investigated. Whole human blood is dropped on leaflet materials and allowed to clot for up to 60 min. The free hemoglobin concentration is measured at 10-min intervals. Leaflet materials are imaged via SEM to visualize the fibrin clot formation.

C. Evaluate the Effect of Leaflet Materials on Platelet and Leukocyte Interaction.

Whole blood plasma contains four main components: platelets, leukocytes, complement, and coagulation, which may play an important role in implant failure in vivo. Thus, thrombogenicity of leaflet materials after 2 hours of incubation in whole blood plasma are evaluated. Indirect immunofluorescence staining determines the cellular expression through the presence of specific marker proteins for platelets (P-selectin), leukocytes (CD45), monocytes/macrophages (CD14), and neutrophils (CD16). The platelet-leukocyte morphology is investigated using SEM imaging to visualize the platelet-leukocyte interaction. Complement activation is assessed using an ELISA to evaluate the degree of SC5b-9 complement activation. Contact activation is assessed to evaluate the degree of plasma kallikrein present on the substrate-exposed plasma using an acid stop method. PF-4 expression is assessed using ELISA to evaluate the degree of platelet activation.

D. Evaluate the Effect of Leaflet Materials on Monocytes and Macrophages.

Whole blood lysate also contains monocytes and is used for these studies. Cell viability is characterized using a 2-(4,5-dimethylthiazol-2-yl)-2,5-diphenyltetraxolium bromide (MTT) assay. Cell adhesion and proliferation is characterized by staining the cytoplasm of adhered cells with 5-chloromethylfluoresciein diacetate (CMFDA) and the nuclei with 4',4-diamidino-2-phenylindole dilactate (DAPI). Cell morphology is investigated using SEM imaging. The cell-released nitric oxide (NO) is detected using a Griess reagent kit. Human inflammatory cytokines/chemokines (TNF, IFN-γ, TGF-β1, MIP-1β, MCP-1, IL-1β, IL-6, IL-8, IL-10 and IL-12p70) is detected using cytometric bead array human plex flex sets. All immunoassays are run together.

E. Evaluate the Effect of Leaflet Materials on EC Adhesion, Proliferation and Differentiation.

Since ECs are involved in the mechanotransduction of the natural HV leaflet, the ability of the leaflet material to endothelialize is investigated. Primary human microvascular ECs isolated from neonatal dermis is used for these studies. EC adhesion and proliferation is investigated using live/dead fluorescence microscopy imaging, MTT assay and SEM. Along with DAPI, the cells are immunostained for actin and vinculin to visualize the changes in their cytoskeleton. The oxidative stress states are investigated under dynamic flow conditions. Endothelial cell monolayers are exposed to static and shear conditions for 24 hours. ELISA is used to determine the differential expression of cytokines such as TNF-α and IL-1β as well as expression of leukocyte adhesion molecules such as VCAM-1, ICAM-1, and E-selectin. Because of the low immunogenicity of HA, EC on the leaflet materials may downregulate stress marker expression. The anti-thrombogenic function of ECs is evaluated by measuring the secretion of anticoagulation factors such as prostacyclin and heparin sulfate using ELISA.

Example 11: Mechanical Properties of Further LLDPE-HA Compositions

Tensile testing is performed, in both the machine direction and transverse direction of the film, on the most hemocompatible materials to confirm anisotropy and no significant change in mechanical properties. If any tensile properties change significantly, testing is repeated on HVs made with leaflets of the new composition to confirm function and durability.

A new composite in accordance with this disclosure may achieve greater than 1.4% HA in the bulk, or greater than an additional 0.05% HA on surface-dipped samples. With a dipping process, homogeneous HA surface densities may occur on all dipped groups. Excellent hemocompatibility of all surfaces with low contact angles at short time points may be achieved, but that those surfaces with the greatest HA surface density exhibit the lowest contact angle and the best hemocompatibility over longer times. Those samples with highest surface concentration of HA may show the largest decrease in fibrinogen adsorption, platelet adhesion/activation, and clotting kinetics.

Inhomogeneous coverage may be avoided with the final HA dipping process. The more uniform surface is used for testing. If neither surface is uniform, the films are dried on a rotisserie where the film is stretched in a frame and then slowly rotated during drying. Inherent in all biological studies is the risk of finding no cell response. Endothelialization may not be achieved; however, leaflet materials should maintain and augment cell function. Hyaluronidase does not degrade the crosslinked, high molecular weight HA on the surface, likely because the crosslinking into the composite limits its molecular mobility, possibly limiting its effect on endothelial cells. Oligomeric (low mW) HA may stimulate the proliferation of ECs in vitro. Thus, if there is little or no difference between our composite leaflet and control materials in EC response, the use of oligomeric HA prepared by hyaluronidase digestion will be explored in the final surface dip with varying amounts of crosslinking, including very light or no crosslinking to see if the oligomeric physically entangled HA coating may be more bioactive to ECs.

Example 12: In Vivo Hemocompatiblity of Composite HV Leaflets

Composite HVs are less thrombogenic and are more calcification resistant than bioprosthetic HVs. Two separate in vivo studies are conducted: (A) a swine study to validate low or minor thrombogenic levels of composite HVs relative to a gold standard bioprosthetic HV, and (B) a juvenile sheep study to validate superior calcification resistance of composite HVs to the gold standard bioprosthetic HV. In both studies, the control valve is the Carpentier Edwards Perimount valve and the test composite HV corresponds to the best composition combined with the best leaflet geometric configuration.

A. Swine Study

The swine model is both anatomically and hemodynamically appropriate for studies of human cardiovascular devices, and the coagulation system closely approximates that of the human neonate. The best composition composite leaflets are assembled into the HV using the Autogenics model, incorporated herein by reference. Valves are sterilized with ethylene oxide. This model provides an in vivo test of the composite materials to demonstrate the lack or need for anticoagulation. The valves are implanted in the pulmonary position in the pig for 8 weeks. Pulmonary position is chosen as the surgery may be performed without full bypass by cannulating the right atrium and pulmonary artery. The pulmonary position is fluid dynamically equivalent to the aortic position except for lower pressures. These lower pressures do not impact fluid shear and material-initiated coagulation. Six pigs are in each treatment group (12 total). The pigs weight about 60 kg and are implanted with a 25-mm valve.

The pig is fasted overnight with water ad libitum. Premedication is performed with Ketamin, midazolam, and morphine. Anesthesia is induced with propofol and then maintained at a surgical level of anesthesia after endotracheal intubation with oxygen and isoflurane. The pig is mechanically ventilated.

The pig is placed in the right lateral recumbency for surgery. A peripheral intravenous line is placed in an ear vein to administer fluid and medication. A left thoracotomy is performed. The pericardium is opened to expose the heart. Heparin (300 U/kg) is administered intravenously. The main pulmonary artery is isolated and purse string sutures placed on the distal part of the pulmonary artery with 4-0 polypropylene, and the right atrium with polypropylene 3-0. The pulmonary artery is cannulated for arterial perfusion using a 24-Fr size cannula, and the right atrium is cannulated for venous return using a 34-Fr two-stage atriocaval cannula. Both cannulae are connected to a standard cardiopulmonary bypass machine with a reservoir without an oxygenator. The pulmonary artery is clamped upstream of the cannula and the pulmonary artery opened. The native pulmonary valve is excised. The test HV (composite or control) is sutured into the annulus with pledgeted 3-0 Ticron™ mattress sutures. A continuous 4-0 polypropylene suture pattern closes the pulmonary artery. After de-airing, the clamps are released and right heart bypass is discontinued. The cannulae are removed. Heparin is reversed with protamine. The chest is closed in layers after inserting a drain. This drain is removed 2 hours postoperatively in all cases.

The pig undergoes transesophageal and transthoracic echocardiographic evaluation after stabilization from the surgical implantation to assess valvular and right ventricular function. Indices of valvular performance include transvalvular flow velocity and pressure gradient (stenosis), color-flow and spectral Doppler analysis for valve regurgitation, M-mode analysis of leaflet motion, and 2-D analysis for presence of thrombus or pannus growth. These are standard cardiac diagnostic procedures routinely conducted at a Veterinary Hospital.

Leaflet function and the presence of thrombus are evaluated echocardiographically at implantation, as well as at 1 and 4 weeks, and before sacrifice at 8 weeks. Several plasma markers elevated upon activation of platelets and coagulation enzymes are measured at these time points. Specifically, consumption of fibrinogen and its cleavage by thrombin are assessed by measurements of plasma clottable fibrinogen and fibrinopeptide A (FPA) levels, respectively. Activation of platelets is judged from the change in circulating platelet count and by plasma levels of releasable platelet α-granule proteins, β-thromboglobulin, and platelet factor 4. Leaflets are photographed for measurements of thrombus free surface and the dimensions of the leaflet are compared with pre-implant dimensions. The % HA in the leaflets are measured using TBO staining and TGA, and SEM is used to examine the leaflets for structural damage.

B. Juvenile Sheep Study

Juvenile sheep are a standard animal model to assess calcification in prosthetic HVs.

The sheep is fasted overnight with water ad libitum. Premedication is performed with ketamine, midazolam, and morphine. Anesthesia is induced with propofol and then maintained at a surgical level of anesthesia after endotracheal intubation with oxygen and isoflurane. The sheep is mechanically ventilated.

The sheep is placed in the right lateral recumbency for surgery. A peripheral intravenous line administers fluid and medication. A left thoracotomy is performed at the second intercoastal space. The pericardium is opened to expose the heart. Heparin (300 U/kg) is administered intravenously. The main pulmonary artery is isolated and purse string sutures placed on the distal part of the pulmonary artery with 4-0 polypropylene, and the right atrium with polypropylene 3-0. The pulmonary artery is cannulated for arterial perfusion using a 24-Fr size cannula and the right atrium is cannulated for venous return using a 34-Fr two-stage atriocaval cannula. Both cannulae are connected to a standard cardiopulmonary bypass machine with a reservoir without an oxygenator. The pulmonary artery are clamped upstream of the cannula and the pulmonary artery opened. The native pulmonary valve will be excised. The test HV (composite or control) will be sutured into the annulus with pledgeted 3-0 Ticron™ mattress sutures. A continuous 4-0 polypropylene suture pattern are used to close the pulmonary artery. After de-airing, the clamps are released and right heart bypass will be discontinued. The cannulae are removed. Heparin is reversed with protamine. The chest is closed in layers after inserting a drain. This drain is removed 2 hours postoperatively in all cases. The sheep is given analgesic, antibiotic, and/or diuretic agents as necessary. Low molecular weight heparin (enoxaparin sodium, 20 mg twice daily) is administered for the first 6 days.

The sheep receives a transthoracic echocardiographic follow up every two weeks. Three of the six implanted valves are explanted at 3 months and the remaining at 6 months. Explanted valves are imaged from both directions and examined grossly with commentary noted. Leaflets are cut out of the explanted valve for Roentgenogram assessment in both directions. The degree of calcification is scored into three categories: 0 for no calcification, 1 for slight calcification, and 2 for severe calcification. Histology is performed with hematoxylin and eosin, Masson's trichrome stain for collagen, an elastic Von Giesson stain, a phosphotungstic-acid-hematoxylin for fibrin, and a Von Kossa calcium staining on one of the three leaflets. Another leaflet undergoes transmission electron microscopy (TEM) analysis. The images are scored for calcification. The last leaflet undergoes quantification of calcification. The leaflet is further cut into three parts: free edge, the commissural area, and basal part. After lyophilization, the sample is pulverized and desiccated, followed by dilution in 20% hydrochloric acid. Calcium content, expressed as microgram per milligram of dry weight, is evaluated using absorption spectrometry.

Valve sizing is a potential problem for testing any prosthetic valve in a live animal. The pig/sheep are pre-evaluated for annulus size. If thrombus is noted at end of week 1, the pigs are placed on a daily aspirin regime (1 mg/kg/day). If aspirin does not sufficiently control thrombus, anti-platelet therapy is used, failing which low dose anticoagulation therapy is used. Once the appropriate anticoagulation therapy is determined, the sheep study continues.

Composite HVs show no or little signs of thrombus in sheep, demonstrating at the minimum equivalence to bioprosthetic HVs. Very little calcification occurs in juvenile sheep demonstrating superiority to bioprosthetic HVs. composite HVs also do not mechanically degrade or have fatigue damage in the study.

Results are analyzed using SigmaStat software version 11.2. Statistical comparisons of parametric data are made using the Student's T test for two-treatment comparisons, ANOVA for multiple treatment comparisons, and Newman-Keuls post hoc analysis with the Holm-Sidak adjustment when sample population variances are similar. The Shapiro-Wilk normality test is performed on all treatments. Significance is assessed at $p<0.05$.

What is claimed is:

1. A composite, comprising:
   a polymer host selected from the group consisting of low-density polyethylene (LDPE), linear low-density polyethylene (LLDPE), polyethylene terephthalate (PET), polytetrafluoroethylene (PTFE), polypropylene (PP), polyurethane, polycaprolactone (PCL), polydimethylsiloxane (PDMS), polymethylmethacrylate (PMMA), and polyoxymethylene (POM); and
   a guest molecule comprising hyaluronic acid;
   wherein the guest molecule is disposed within the polymer host, and
   wherein the guest molecule is covalently bonded to at least one other guest molecule forming cross-linked guest molecules, such that the cross-linked guest molecules interpenetrate the polymer host molecule at a nanometer scale.

2. The composite of claim 1, wherein the polymer host is a film with a thickness of 25 μm to 100 μm.

3. The composite of claim 2, wherein the film has a thickness of 50 μm.

4. The composite of claim 1, wherein the concentration of guest molecule in the composite is greater at the surface of the polymer host than at the core of the polymer host.

5. The composite of claim 1, wherein the aqueous contact angle at the surface of the composite is 10° to 90°.

6. The composite of claim 5, wherein the aqueous contact angle at the surface of the composite is 40° to 80°.

7. The composite of claim 1, wherein the average molecular weight of the guest molecule is 0.75 kDa to 1,000 kDa.

8. The composite of claim 7, wherein the average molecular weight is 1 kDa to 10 kDa.

9. A blood-contacting device formed from a composite comprising:
   a polymer host selected from the group consisting of low-density polyethylene (LDPE), linear low-density polyethylene (LLDPE), polyethylene terephthalate (PET), polytetrafluoroethylene (PTFE), polypropylene (PP), polyurethane, polycaprolactone (PCL), polydimethylsiloxane (PDMS), polymethylmethacrylate (PMMA), and polyoxymethylene (POM); and
   a guest molecule comprising hyaluronic acid;
   wherein the guest molecule is disposed within the polymer host, and
   wherein the guest molecule is covalently bonded to at least one other guest molecule forming cross-linked guest molecules, such that the cross-linked guest molecules interpenetrate the polymer host molecule at a nanometer scale.

10. The device of claim 9, wherein the device is a heart valve, comprising a flow control member selected from the group consisting of a leaflet, a tilting disk, and a ball-in-cage mechanism.

11. The device of claim 9, wherein the composite, upon contact with blood, substantially reduces thrombogenesis and/or substantially improves endothelialization compared to the polymer host without a guest molecule disposed therein.

12. The heart valve of claim 10, wherein the flow control member is a leaflet formed from the composite, and the polymer host is selected from the group consisting of low-density polyethylene (LDPE) film, linear low-density polyethylene (LLDPE) film, and polyethylene terephthalate (PET) fabric.

13. The heart valve of claim 12, further comprising a suture ring or sewing cuff made from a second composite, the second composite comprising:
   a second polymer host comprising PET fabric and
   a second guest molecule comprising hyaluronic acid,
   wherein the second guest molecule is disposed within the second polymer host, and
   wherein the second guest molecule is covalently bonded to at least one other second guest molecule forming cross-linked guest molecules, such that the cross-linked second guest molecules interpenetrate the second polymer host molecule at a nanometer scale.

14. The device of claim 9, wherein the device is a small-diameter vascular graft formed from the composite, and the polymer host comprises expanded polytetrafluoroethylene (ePTFE).

15. The heart valve of claim 10,
   the heart valve further comprising a suture ring made from the composite, the polymer host comprising PET fabric and
   wherein the flow control member is a tilting disk formed from a second composite comprising:
      a second polymer host comprising ultra-high molecular weight polyethylene (UHMWPE), and
      a second guest molecule comprising hyaluronic acid;
      wherein the second guest molecule is disposed within the second polymer host, and
      wherein the second guest molecule is covalently bonded to at least one other second guest molecule forming cross-linked guest molecules, such that the cross-linked second guest molecules interpenetrate the second polymer host molecule at a nanometer scale.

16. The device of claim 9, wherein the device is a suture ring or sewing cuff made from the composite, and the polymer host comprises PET fabric.

* * * * *

UNITED STATES PATENT AND TRADEMARK OFFICE
CERTIFICATE OF CORRECTION

PATENT NO. : 10,071,186 B2
APPLICATION NO. : 14/381332
DATED : September 11, 2018
INVENTOR(S) : Susan P. James et al.

It is certified that error appears in the above-identified patent and that said Letters Patent is hereby corrected as shown below:

In the Specification

In Column 1, after Line 15, insert the following:
--GOVERNMENT LICENSE RIGHTS
This invention was made with government support under grants R03 EB014255 and R01 HL119824 awarded by National Institutes of Health. The government has certain rights in the invention.--

Signed and Sealed this
Nineteenth Day of March, 2019

Andrei Iancu
*Director of the United States Patent and Trademark Office*